(12) United States Patent
Hartmann et al.

(10) Patent No.: US 7,933,012 B2
(45) Date of Patent: Apr. 26, 2011

(54) MICROFLUIDIC CHIP APPARATUSES, SYSTEMS AND METHODS HAVING FLUIDIC AND FIBER OPTIC INTERCONNECTIONS

(75) Inventors: Daniel M. Hartmann, East Lansing, MI (US); Joshua T. Nevill, El Cerrito, CA (US); Pang-Jen Craig Kung, Cary, NC (US); Kenneth I. Pettigrew, Sutherland, VA (US); Brian Herbert Warrington, Hertfordshire (GB); Hugh C. Crenshaw, Durham, NC (US)

(73) Assignee: AB Sciex LLC MA (US)

( * ) Notice: Subject to any disclaimer, the term of this patent is extended or adjusted under 35 U.S.C. 154(b) by 716 days.

(21) Appl. No.: 11/719,527

(22) PCT Filed: Aug. 10, 2006

(86) PCT No.: PCT/US2006/031164
§ 371 (c)(1),
(2), (4) Date: May 16, 2007

(87) PCT Pub. No.: WO2007/021815
PCT Pub. Date: Feb. 22, 2007

(65) Prior Publication Data
US 2009/0147253 A1 Jun. 11, 2009

Related U.S. Application Data

(60) Provisional application No. 60/707,246, filed on Aug. 11, 2005.

(51) Int. Cl.
*G01N 1/10* (2006.01)
(52) U.S. Cl. .................................................. 356/246
(58) Field of Classification Search ........... 356/244–246
See application file for complete search history.

(56) References Cited

U.S. PATENT DOCUMENTS

| | | | | |
|---|---|---|---|---|
| 5,338,435 | A * | 8/1994 | Betts et al. | 204/406 |
| 5,405,510 | A * | 4/1995 | Betts et al. | 205/782 |
| 5,473,721 | A | 12/1995 | Myers et al. | |
| 5,655,395 | A | 8/1997 | Merchel | |
| 6,103,344 | A | 8/2000 | Ota et al. | |
| 6,290,791 | B1 * | 9/2001 | Shaw et al. | 156/64 |
| 6,600,558 | B2 | 7/2003 | Ueno et al. | |

OTHER PUBLICATIONS

PCT/US06/31164 Written Opinon of the International Searching Authority dated Dec. 21, 2007.
PCT/US06/31164 International Preliminary Report of Patentability dated Mar. 26, 2009.

(Continued)

*Primary Examiner* — Michael P Stafira

(57) ABSTRACT

According to one embodiment, apparatuses and methods are provided for connecting a light-guiding conduit to a microfluidic channel. First and second substrates with first surfaces can be provided, wherein the first surfaces of the first and second substrates form a microfluidic channel and a connection channel when the first surfaces are positioned together, and wherein the connection channel extends from an edge of the first surface of the first or second substrate to the microfluidic channel. The apparatus and method can also include bonding the first surfaces of the first and second substrates to form the microfluidic channel and the connection channel. A light-guiding conduit can be inserted into the connection channel such that the light-guiding conduit connects to the microfluidic channel and filling an area between the light-guiding conduit and the connection channel for forming a liquid-tight seal between the light-guiding conduit and the connection channel.

27 Claims, 35 Drawing Sheets

OTHER PUBLICATIONS

Bings, N.H. et al., "Microfluidic Devices Connected to Fused-Silica Capillaries with Minimal Dead Volume," Anal. Chem., 1999, vol. 71, pp. 3292-3296.

Galambos, P. et al., "Precision Alignment Packaging for Microsystems With Multiple Fluid Connections," Proceedings of 2001 Amer. Soc. Mech. Eng., Nov. 11-16, 2001, 8 pages.

* cited by examiner

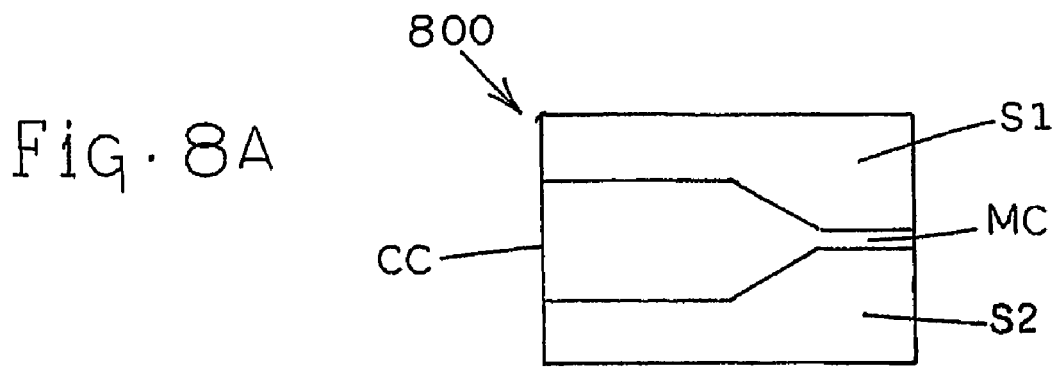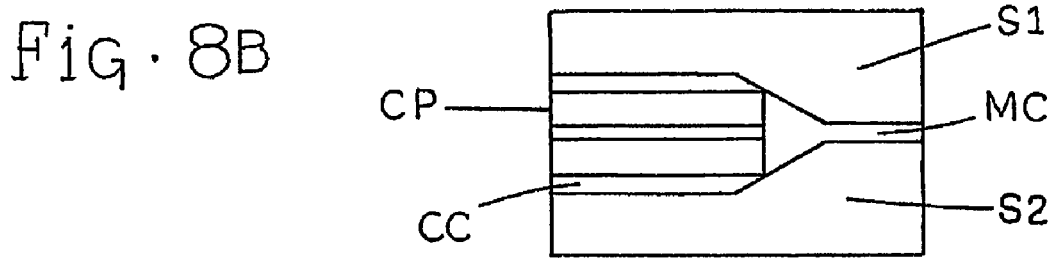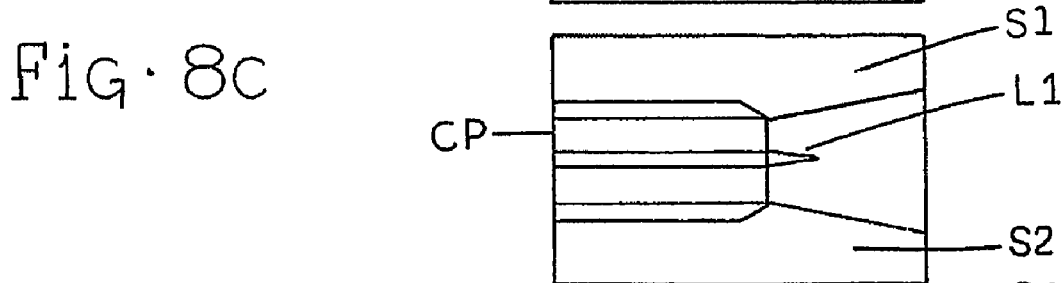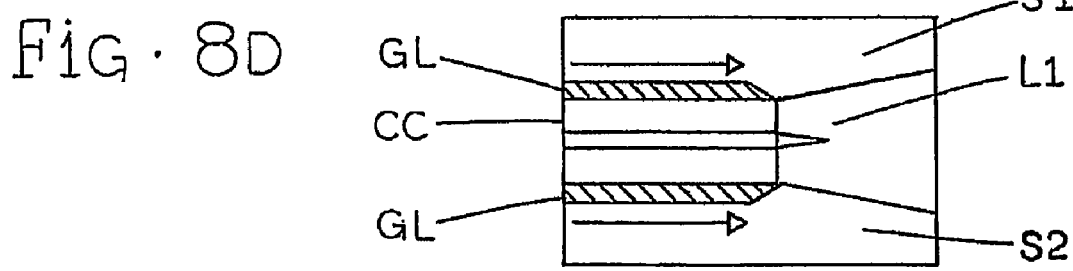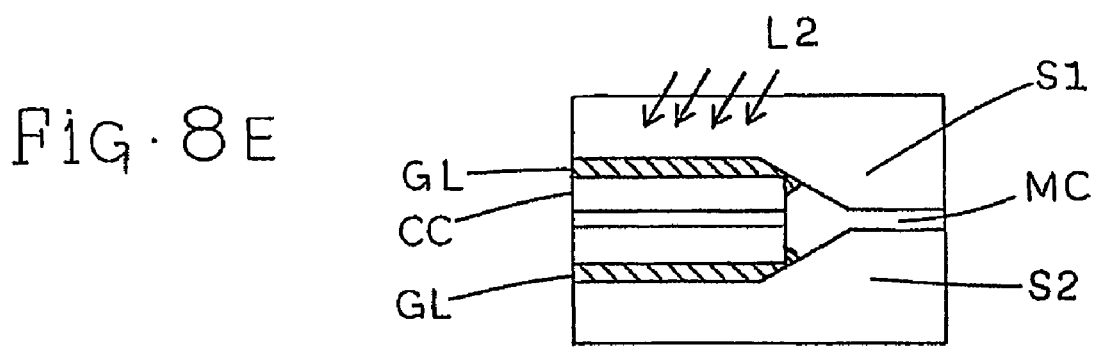

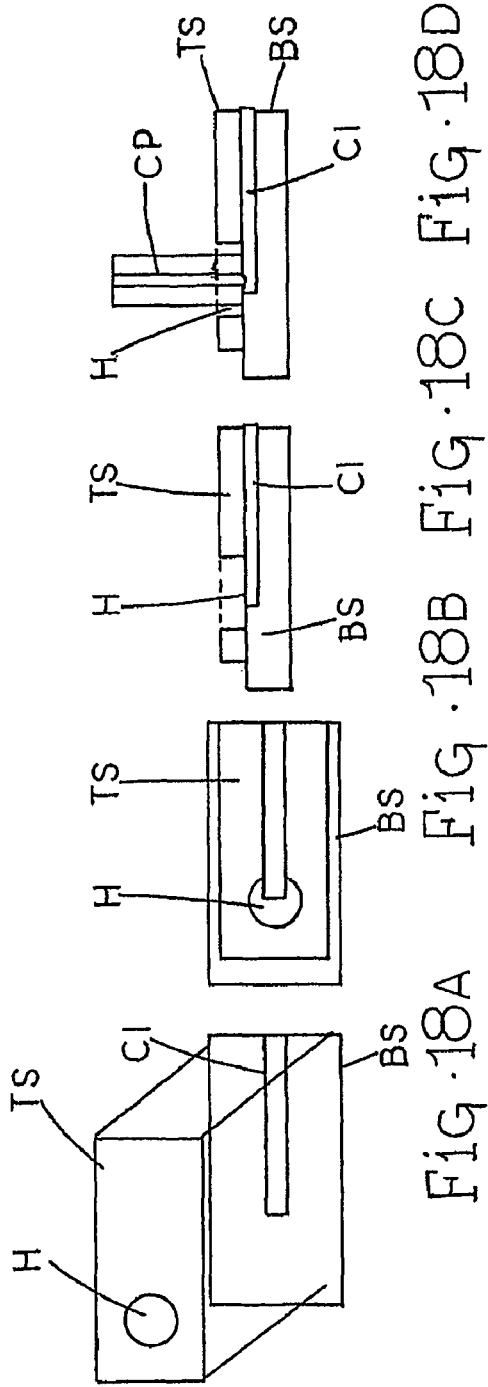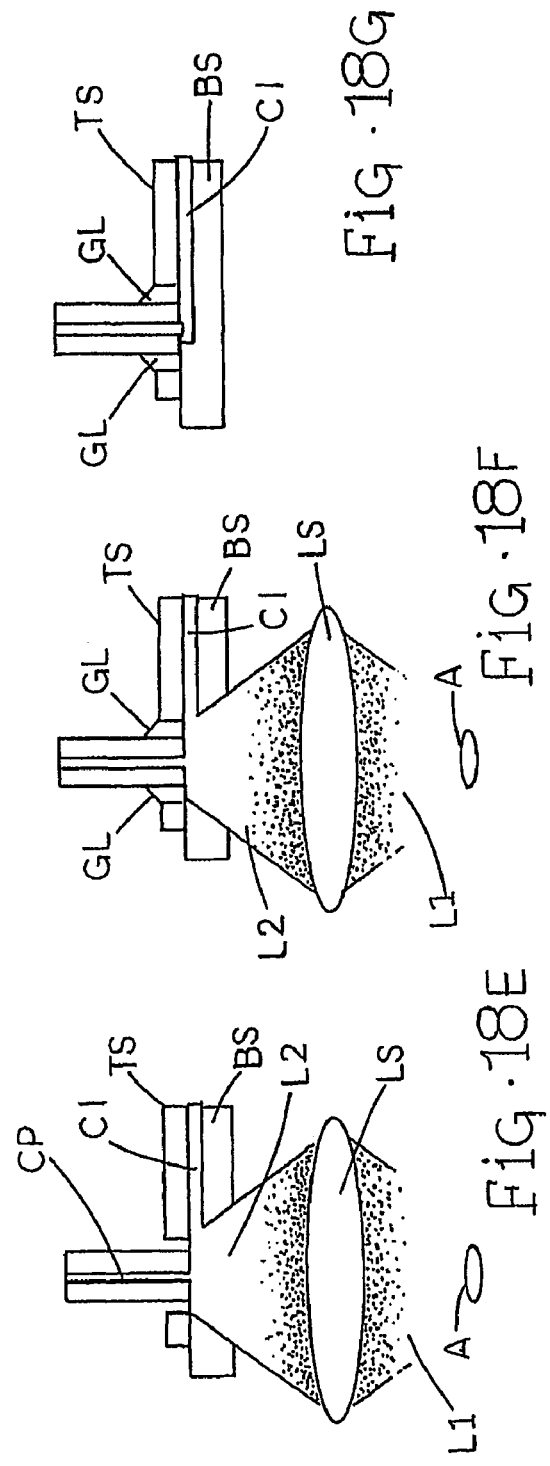

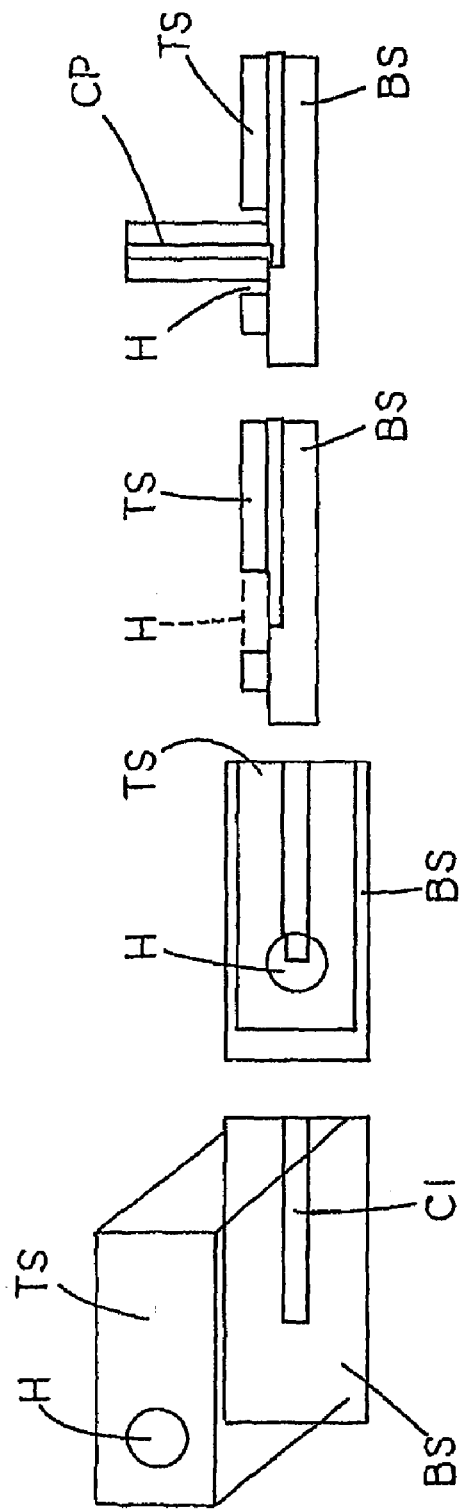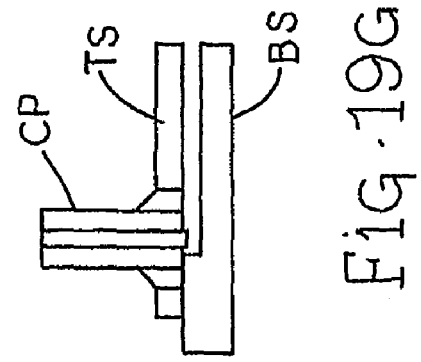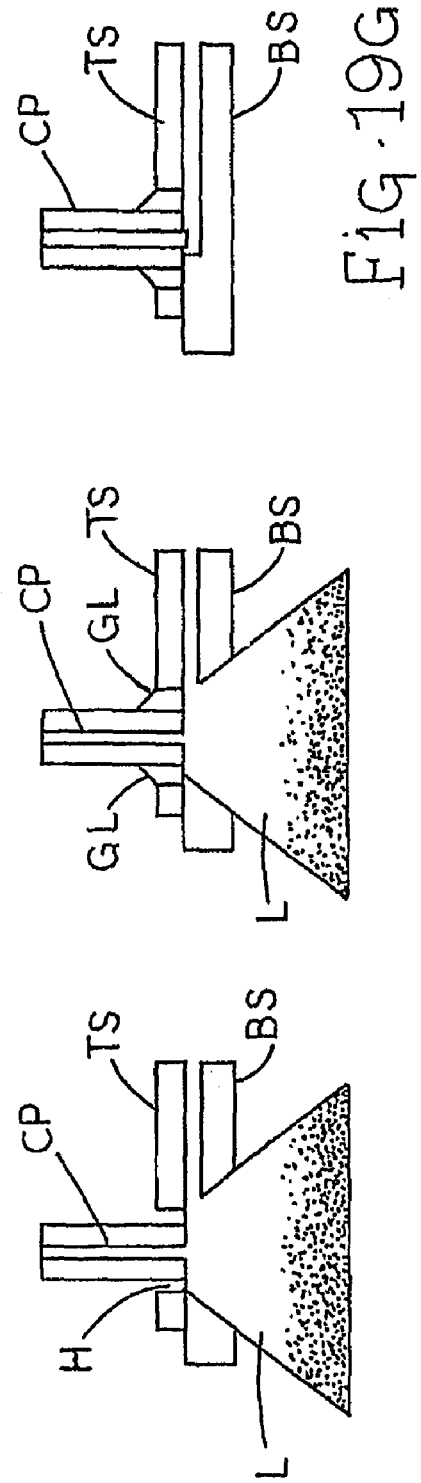

MICROFLUIDIC CHIP APPARATUSES, SYSTEMS AND METHODS HAVING FLUIDIC AND FIBER OPTIC INTERCONNECTIONS

CROSS-REFERENCE TO RELATED APPLICATIONS

This application is the U.S. national stage of International Application No. PCT/US2006/31164, filed Aug. 10, 2006 and entitled MICROFLUIDIC CHIP APPARATUSES, SYSTEMS AND METHODS HAVING FLUIDIC AND FIBER OPTIC INTERCONNECTIONS, which claims the benefit of U.S. Patent Application Ser. No. 60/707,246, filed Aug. 11, 2005, the disclosure of which is incorporated herein by reference in its entirety. The disclosures of the following U.S. Provisional Applications, commonly owned and simultaneously filed Aug. 11, 2005, are all incorporated by reference in their entirety: U.S. Provisional Application entitled APPARATUS AND METHOD FOR HANDLING FLUIDS AT NANO-SCALE RATES, U.S. Provisional Application No. 60/707,421; U.S. Provisional Application entitled MICROFLUIDIC BASED APPARATUS AND METHOD FOR THERMAL REGULATION AND NOISE REDUCTION, U.S. Provisional Application No. 60/707,330; U.S. Provisional Application entitled MICROFLUIDIC METHODS AND APPARATUSES FOR FLUID MIXING AND VALVING, U.S. Provisional Application No. 60/707,329; U.S. Provisional Application entitled METHODS AND APPARATUSES FOR GENERATING A SEAL BETWEEN A CONDUIT AND A RESERVOIR WELL, U.S. Provisional Application No. 60/707,286; U.S. Provisional Application entitled MICROFLUIDIC SYSTEMS, DEVICES AND METHODS FOR REDUCING DIFFUSION AND COMPLIANCE EFFECTS AT A FLUID MIXING REGION, U.S. Provisional Application No. 60/707,220; U.S. Provisional Application entitled MICROFLUIDIC SYSTEMS, DEVICES AND METHODS FOR REDUCING NOISE GENERATED BY MECHANICAL INSTABILITIES, U.S. Provisional Application No. 60/707,245; U.S. Provisional Application entitled MICROFLUIDIC SYSTEMS, DEVICES AND METHODS FOR REDUCING BACKGROUND AUTOFLUORESCENCE AND THE EFFECTS THEREOF, U.S. Provisional Application No. 60/707,386; U.S. Provisional Application entitled MICROFLUIDIC CHIP APPARATUSES, SYSTEMS, AND METHODS HAVING FLUIDIC AND FIBER OPTIC INTERCONNECTIONS, U.S. Provisional Application No. 60/707,246; U.S. Provisional Application entitled METHODS FOR CHARACTERIZING BIOLOGICAL MOLECULE MODULATORS, U.S. Provisional Application No. 60/707,328; U.S. Provisional Application entitled METHODS FOR MEASURING BIOCHEMICAL REACTIONS, U.S. Provisional Application No. 60/707,370; U.S. Provisional Application entitled METHODS AND APPARATUSES FOR REDUCING EFFECTS OF MOLECULE ADSORPTION WITHIN MICROFLUIDIC CHANNELS, U.S. Provisional Application No. 60/707,366; U.S. Provisional Application entitled PLASTIC SURFACES AND APPARATUSES FOR REDUCED ADSORPTION OF SOLUTES AND METHODS OF PREPARING THE SAME, U.S. Provisional Application No. 60/707,288; U.S. Provisional Application entitled BIOCHEMICAL ASSAY METHODS, U.S. Provisional Application No. 60/707,374; U.S. Provisional Application entitled FLOW REACTOR METHOD AND APPARATUS, U.S. Provisional Application No. 60/707,233; and U.S. Provisional Application entitled MICROFLUIDIC SYSTEM AND METHODS, U.S. Provisional Application No. 60/707,384.

TECHNICAL FIELD

The subject matter disclosed herein relates generally to microfluidic chip technology. More particularly, the subject matter disclosed herein relates to microfluidic chip apparatuses, systems, and methods having fluidic and fiber optic interconnections and related methods.

BACKGROUND ART

Microelectromechanical systems (MEMS) have been developed for miniaturizing many different systems, such as scientific instruments or real-time monitoring devices. Many MEMS devices resemble integrated electronic circuits in that they are actually components that must be combined with other components to achieve a desired function. Unlike integrated electronic circuits, MEMS frequently must connect not just electrically to other components, but also by other physico-chemical parameters, such as optically and fluidically.

Electrical connections for miniaturized systems, such as integrated circuits, have benefited from extensive technical development, both to improve the connection (e.g. decrease form factor, decrease resistance, increase tolerance to extreme conditions) and to improve manufacturability, primarily to make formation of the connection amenable to automation.

MEMS are a less mature technology, and optical and fluidic connections from MEMS to other components remain very problematic. Improvements are needed both to improve the connections and to make them more manufacturable. In the case of optical connections, extensive effort has been expended to automate the connection of just fiber optics. The development of all-optical communications networks, however, requires the integration of many, diverse optical components, such as spectral filters, lasers, diffraction gratings, beamsplitters, and photodetectors. The connection and assembly of many of these components is still a manual process. Fluidic connections have proven the most problematic. Fluidic connections can have many of the same requirements that other MEMS connections do, such as micrometer precision of placement, and rigid and strong mechanical attachment. However, fluidic connections must conform to the edges of the fluidic passageways, making a water-tight seal without occluding the passageways. Furthermore, the seal must be able to withstand pressure of tens of pounds per square inch (p.s.i.) for low-pressure systems and tens of thousands of p.s.i. for some higher pressure systems. Furthermore, fluid connections must be compatible with the fluids to be transported. The materials of the fluid connections must be inert—they should not dissolve in, imbibe, or react with the fluid or chemicals dissolved in the fluid; nor should dissolved chemicals adsorb to the surfaces of the connection.

Fluid connections sometimes also must achieve stringent requirements for dead volume (the volume of the connection), void volume (volumes that extend out of the needed connection), and dispersion (defined later). Fluidic connections with large dead volumes can greatly increase the total volume of a system, contrary to the goal of miniaturization. Dispersion is the tendency of a fluidic system to degrade chemical concentration gradients. For example, if a chemical dissolved in a flow is suddenly increased, then the increase in concentration can be considered as a step that flows down the fluidic channel. Dispersion acts to reduce the steepness of the step—a sudden increase in concentration is turned into a more gradual gradient due to dispersion. One common contributor to dispersion is "unswept" or "void" volume. This is a volume of fluid in the interconnect that is outside the main flow through the interconnect. For example, a crevice between the ends of the walls of two channels that are joined end-to-end will contain a volume of fluid that is stagnant, even if fluid flows through the channel. Similarly, any sudden expansion or contraction of the fluid channel diameter will produce corners where the fluid flows more slowly, increasing dispersion.

Void volumes also result in "carry-over" when different fluids are passed sequentially through a fluidic system. Carry-over results in contamination of fluids by fluids that previously passed through the system. Such contamination is extremely problematic for analytical systems that must have, for example, large dynamic range or sensitive detection.

Connection of MEMS microfluidic channels to external fluid reservoirs frequently includes the attachment of microcapillaries to the MEMS microfluidic channels. This is done by a variety of techniques, such as gluing or use of fittings traditionally used in liquid chromatography. Examples of microfluidic connections include the "sipper chip" technology described in U.S. Pat. No. 5,779,868, the NANOPORT™ components available from Upchurch Scientific, Inc. (Oak Harbor, Wash.), and various connections in the CAPTITE™ and CHIP-TITE™ series developed at Sandia National Labs. A more experimental system that attempts a more comprehensive solution to multi-type connections for MEMS is described in Galambos et al. 2001, Proc. Of 2001 Amer. Soc. Mech. Eng., Nov. 11-16. A technique for connecting capillary tubing to a microfluidic chip that permits limited control over the placement of the seal is described by Bings et al., 1999, *Analytical Chemistry*, Vol. 71, pages 3292-6.

Coupling optical systems to fluidic systems has the challenges of both optical and fluidic engineering—precise alignment, watertight seals, low dead volumes, low dispersion, and efficient optical coupling are required. Optical coupling has been achieved both with remotely positioned light sources and detectors as well as with integrated optical lightguides. Remotely positioned light sources and detectors are most intolerant of relative movements of components, and thus require precise and stable positioning of all components. Integrated optical lightguides require expensive fabrication techniques and, unless the light source and detector are integrated into the MEMS device, optical coupling of the integrated lightguides in the MEMs device to external light sources and sensors is still required.

Summarily, it is desirable to provide simple, reliable, and manufacturable techniques for connecting fiber optics and capillaries to microfluidic MEMS devices.

SUMMARY

According to one embodiment, a method is disclosed for connecting a light-guiding conduit to a microfluidic channel formed between a first and second substrate. The method can include a step for providing a first and second substrate comprising first surfaces, wherein the first surfaces of the first and second substrates form a microfluidic channel and a connection channel when the first surfaces are positioned together and the connection channel extends from an edge of the first surface of the first or second substrate to, the microfluidic channel. The method can also include a step for bonding the first surfaces of the first and second substrates to form the microfluidic channel and the connection channel. Further, the method can include a step for inserting a light-guiding conduit into the connection channel such that the light-guiding conduit connects to the microfluidic channel. The method can also include a step for filling an area between the light-guiding conduit and the connection channel with a substance for forming a liquid-tight seal between the capillary and the connection channel.

According to a second embodiment, a method is disclosed for connecting a filamentous component to a microfluidic channel formed between a first and second substrate. The method can include a step for providing a first and second substrate comprising first at least substantially planar surfaces. The method can also include a step for etching a microfluidic channel and connection channel in one of the first planar surfaces of the first and second substrate, wherein the connection channel extends from an edge of the first planar surface of the first or second substrate to the microfluidic channel. Further, the method can include a step for bonding the first surfaces of the first and second substrates to enclose the microfluidic channel and the connection channel. The method can also include a step for inserting a filamentous component into the connection channel such that the filamentous component connects to the microfluidic channel. The method can also include a step for applying an adhesive to the filamentous component and the connection channel to provide a liquid-tight seal between the filamentous component and the connection channel.

According to a third embodiment, a microfluidic device is provided. The microfluidic device can include a first and second substrate comprising first surfaces, wherein the first surfaces of the first and second substrate are attached and form a microfluidic channel and a connection channel and the connection channel extends from an edge of the first surface of the first or second substrate to the microfluidic channel. The microfluidic device can also include a light-guiding conduit attached to the connection channel, wherein the capillary conduit is fluidly connected to the microfluidic channel.

According to a fourth embodiment, a microfluidic device is disclosed. The microfluidic device can include a first and second substrate comprising first surfaces. The first surfaces of the first and second substrate can be attached and form a microfluidic channel and a connection channel. Further, the connection channel can extend from an edge of the first surface of the first or second substrate to the microfluidic channel. A light-guiding conduit can be attached to the connection channel. Further, the light-guiding can be fluidly connected to the microfluidic channel. The first and second substrates can comprise a material selected from the group consisting of polymer, metal, silicon, silica, glass, quartz, sapphire, zinc oxide, alumina, Group III-V compounds, and combinations thereof. The first and second surfaces of the first substrate can be at least substantially planar. The first surface of the first substrate can comprise the microfluidic element and connection channel formed therein. The microfluidic channel and the connection channel can be in fluid communication.

According to a fifth embodiment, a method is disclosed for connecting a fiber optic to a microfluidic channel. The method can include a step for providing a first and second substrate comprising first surfaces, wherein the first surfaces of the first and second substrates form a microfluidic channel and a first fiber optic channel when the first surfaces are positioned together and the first fiber optic channel extends from an edge of the first surface of the first or second substrate in a direction towards the microfluidic channel. The method can also include a step for bonding the first surfaces of the first and second substrates to form the microfluidic channel and the first fiber optic channel. Further, the method can include a step for inserting a fiber optic into the first fiber optic channel such that the fiber optic aligns with the microfluidic channel. The method can also include a step for attaching the fiber optic to the first fiber optic channel.

According to a sixth embodiment, a method is disclosed for connecting a fiber optic to a microfluidic channel. The method can include a step for providing a first and second substrate comprising first at least substantially planar surfaces, wherein the first planar surfaces of the first and second substrate form a microfluidic channel and a first fiber optic channel when the first planar surfaces are positioned together, and wherein the first fiber optic channel extends from an edge of the first planar surface of the first or second substrate in a direction towards the microfluidic channel. The method can also include a step for bonding the first planar surfaces of the first and second substrates to form the microfluidic channel and the first fiber optic channel. Further, the method can include a step for inserting a fiber optic into the first fiber optic channel such that the fiber optic aligns with the microfluidic channel. The method can also include a step for applying adhesive to the fiber optic and the first fiber optic channel to attach the fiber optic to the first fiber optic channel.

According to a seventh embodiment, a microfluidic device is disclosed which can include a first and second substrate comprising first surfaces. The first surfaces of the first and second substrate can be attached and form a microfluidic channel and a first fiber optic channel. The first fiber optic channel can extend from an edge of the first surface of the first or second substrate in a direction towards the microfluidic channel. The microfluidic device can also include an fiber optic attached to the first fiber optic channel, wherein the fiber optic at least substantially aligns with the microfluidic channel.

According to an eighth embodiment, a microfluidic system is disclosed for optically analyzing fluids. The microfluidic system can include a microfluidic device. The microfluidic device can include a first and second substrate comprising first surfaces, wherein the first surfaces of the first and second substrate are attached and form a microfluidic channel and a first fiber optic channel. Additionally, the first fiber optic channel can extend from an edge of the first surface of the first or second substrate in a direction towards the microfluidic channel. The microfluidic device can also include a fiber optic attached to the first fiber optic channel, wherein the fiber optic at least substantially aligns with the microfluidic channel. Further, the microfluidic system can include a light source operable to transmit light through the fiber optic. The microfluidic system can also include detection equipment for receiving light through the fiber optic.

According to a ninth embodiment, a system is disclosed for connecting a light-guiding conduit to a microfluidic chip. The system can include a capillary positioner for maintaining a first end of a light-guiding conduit in a position for communicating light with an interior of the light-guiding conduit. Further, the system can include a microfluidic chip including a connection channel for holding a second end of the light-guiding conduit for communicating light between the microfluidic chip and the interior of the light-guiding conduit. The system can also include a robotic arm for moving the first end of the light-guiding conduit to the position for communicating light with the interior of the light-guiding conduit.

According to a tenth embodiment, a method is disclosed for connecting a filamentous component to a microfluidic channel. The method can include a step for providing a first and second substrate comprising first surfaces. The first surfaces of the first and second substrates can form a microfluidic channel and a connection channel when the first surfaces are positioned together. Further, the connection channel can extend through the first or second substrate to the microfluidic channel. The method can also include a step for bonding the first surfaces of the first and second substrates to form the microfluidic channel. Further, the method can include a step for inserting a filamentous component into the connection channel such that the filamentous component communicates with the microfluidic channel. The method can also include a step for filling an area between the filamentous component and the connection channel with a light-curable adhesive. Further, the method can include a step for applying a focused light beam on the light-curable adhesive for forming a liquid-tight seal between the filamentous component and the connection channel.

According to an eleventh embodiment, a method is disclosed for connecting a light-guiding conduit to a microfluidic channel. The method can include a step for providing a first and second substrate comprising first surfaces, wherein the first surfaces of the first and second substrates form a microfluidic channel and a connection channel when the first surfaces are positioned together. The connection channel can extend through the first or second substrate to the microfluidic channel. Further, the method can include a step for bonding the first surfaces of the first and second substrates to form the microfluidic channel. The method can also include a step for inserting a light-guiding conduit into the connection channel such that the light-guiding conduit communicates with the microfluidic channel. Further, the method can include a step for filling an area between the light-guiding conduit and the connection channel with a light-curable adhesive.

It is therefore an object to provide novel microfluidic chip apparatuses, systems, and methods having fluidic and fiber optic interconnections.

BRIEF DESCRIPTION OF THE DRAWINGS

Exemplary embodiments of the subject matter will now be explained with reference to the accompanying drawings, of which:

FIGS. 8A-8E illustrate views of different stages in the assembly of a microfluidic chip and connection channels by transmitting light through a connection channel for curing glue;

FIGS. 18A-18G illustrate views of different stages in the assembly of a microfluidic chip and connection channel with a fiber optic, a wire, or a capillary;

FIG. 19A-19G illustrate views of alternative stages in the assembly of a microfluidic chip and connection channel with a fiber optic or capillary;

DETAILED DESCRIPTION

Figure 1:
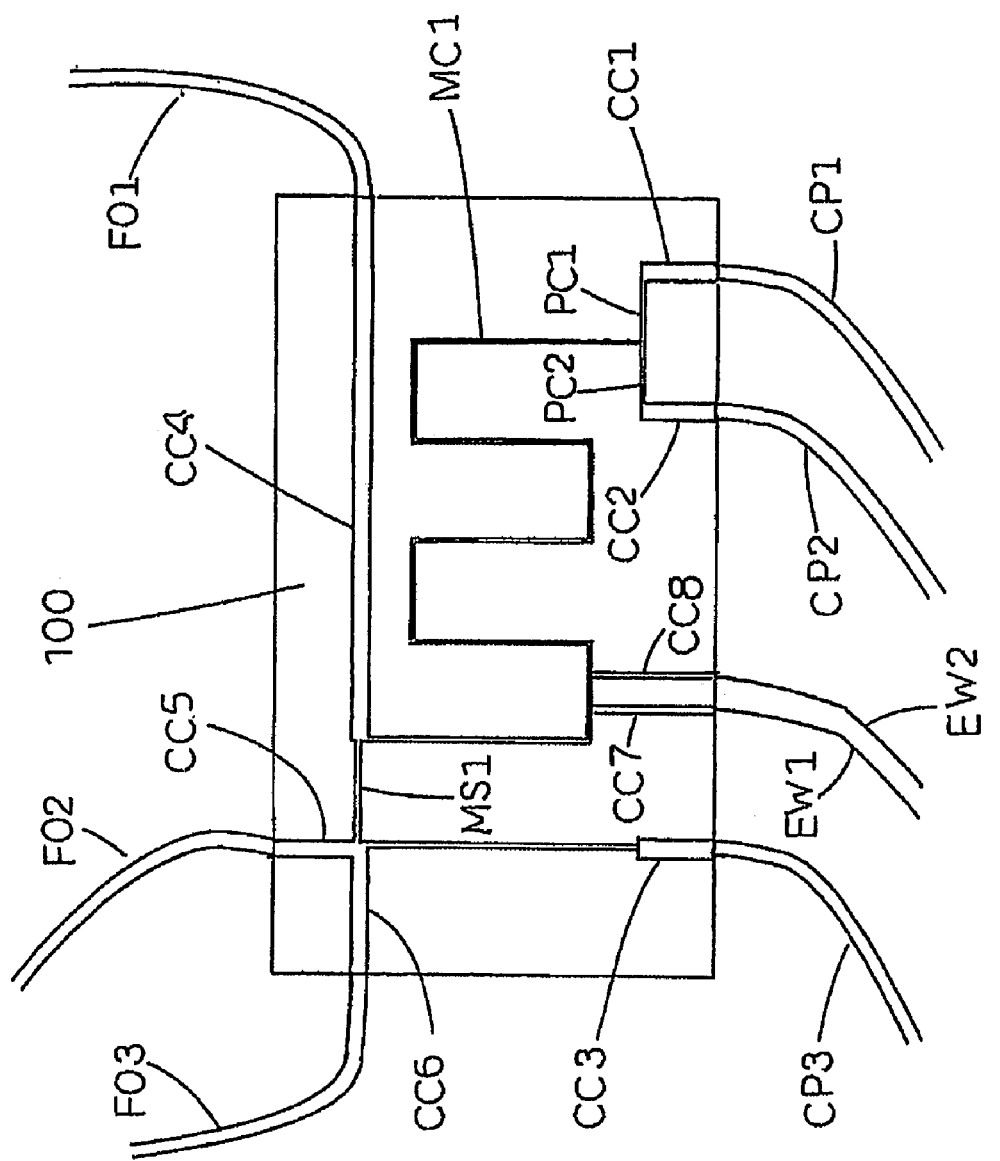
FIG. 1 is a schematic diagram of an exemplary embodiment of a microfluidic system for generating and mixing continuous fluid flows.

In accordance with the subject matter disclosed herein and the various figures of drawings, microfluidic chip apparatuses, systems, and method having fluidic and fiber optic interconnections are provided Methods for fabricating microfluidic chips are described herein which incorporate improved methods for fabricating microfluidic chips. Furthermore, methods and systems are described herein which incorporate improved fluidic and fiber optic interconnects for microfluidic chips. It should be appreciated that the various figures of drawings do not constitute limitations on the scope of the disclosed fabrication methods.

As used herein, the term "fluid" generally means any flowable medium such as liquid, gas, vapor, supercritical fluid, combinations thereof, or the ordinary meaning as understood by those of skill in the art.

As used herein, the term "vapor" generally means any fluid that can move and expand without restriction except for a physical boundary such as a surface or wall, and thus can include a gas phase, a gas phase in combination with a liquid phase such as a droplet (e.g., steam), supercritical fluid, the like, or the ordinary meaning as understood by those of skill in the art.

As used herein, "bonding of substrates" or "substrate bonding" generally means an applicable process for joining one or more substrates used to make a microfluidic chip, such as via anodic bonding, fusion bonding, thermal bonding, epoxying, and compression bonding.

As used herein, the term "reagent" generally means any flowable composition or chemistry. The result of two reagents combining together is not limited to any particular response, whether a biological response or biochemical reaction, a dilution, or the ordinary meaning as understood by those of skill in the art.

In referring to the use of a microfluidic chip for handling the containment or movement of fluid, the terms "in", "on", "into", "onto", "through", and "across" the chip generally have equivalent meanings.

As used herein, the term "microfluidic chip," "microfluidic system," or "microfluidic device" generally refers to a chip, system, or device which can incorporate a plurality of interconnected channels or chambers, through which materials, and particularly fluid borne materials can be transported to effect one or more preparative or analytical manipulations on those materials. A microfluidic chip is typically a device comprising structural or functional features dimensioned on the order of millimeter-scale or less, and which is capable of manipulating a fluid at a flow rate on the order of one hundred μl/min or less. Typically, such channels or chambers include at least one cross-sectional dimension that is in a range of from about 1 μm to about 500 μm. The use of dimensions on this order allows the incorporation of a greater number of channels or chambers in a smaller area, and utilizes smaller volumes of reagents, samples, and other fluids for performing the preparative or analytical manipulation of the sample that is desired.

As used herein, the term "filamentous component" generally refers to a fluid delivery tube such as a capillary tube, a light-guiding conduit such as a fiber optic, a wire, or any other suitable component for connection to a microfluidic device, channel, or chip. Further, a capillary or fiber optic may also refer to any other suitable filamentous component.

Microfluidic systems are capable of broad application and can generally be used in the performance of biological and biochemical analysis and detection methods. The systems described herein can be employed in research, diagnosis, environmental assessment and the like. In particular, these systems, with their micron and submicron scales, volumetric fluid control systems, and integratability, can generally be designed to perform a variety of fluidic operations where these traits are desirable or even required. In addition, these systems can be used in performing a large number of specific assays that are routinely performed at a much larger scale and at a much greater cost.

A microfluidic device or chip can exist alone or may be a part of a microfluidic system which, for example and without limitation, can include: pumps for introducing fluids, e.g., samples, reagents, buffers and the like, into the system; detection equipment or systems; data storage systems; and control systems for controlling fluid transport and/or direction within the device, monitoring and controlling environmental conditions to which fluids in the device are subjected, e.g., temperature, current and the like.

A schematic diagram of an exemplary embodiment of a microfluidic chip 100 for mixing continuous fluid flows is illustrated in FIG. 1. Microfluidic chip 100 has multiple fluidic, optical, and electrical connections. Central to microfluidic chip 100 is a microchannel MC1 that comprises the on-chip channels for transporting and combining fluids. Microcapillaries CP1 and CP2 connect to microfluidic chip 100 via connection channels CC1 and CC2, respectively, which connect to premixing channels PC1 and PC2, respectively. Microcapillaries CP1 and CP2 can connect to external reservoirs of fluid (not shown), such as external pumps, for conveying fluids to microchannel MC1. Connection channels CC1 and CC2 provide alignment by which microcapillaries CP1 and CP2 are aligned with microchannel MC1 and a strong mechanical connection for holding microcapillaries CP1 and CP2.

A capillary CP3 can be connected to microchannel MC1 via channel CC3. Capillary CP3 can remove fluids from chip 100 to a waste reservoir or to another system for further processing or analysis.

Fiber optics FO1, FO2, and FO3 can connect to connection channels CC4, CC5, and CC6, respectively. Connection channels CC4, CC5, and CC6 can align fiber optics FO1, FO2, and FO3 with channel MC1 and provide a strong mechanical connection for holding fiber optics FO1, FO2, and FO3 to microfluidic chip 100.

Electrical wires EW1 and EW2 can connect to channel MC1 on chip 100 via connection channels CC7 and CC8, respectively.

This combination of microcapillaries, fiber optics, and wires that connect to microchannel MC1 on microfluidic chip 100 can be used for a variety of functions. For example, fiber optic FO3 can connect to a light source (such as a laser or a UV lamp) and deliver light to microchannel segment MS1 of channel MC1. Fluid in microchannel MC1 can include fluorescent chemicals or particles that scatter the light delivered from fiber optic FO3. Additionally, fiber optic FO2 can capture light at segment MS1 and convey it to a photodetector (not shown), such as a photodiode or a photomultiplier tube. The fluid in microchannel segment MS1 can absorb light, and fiber optic FO1 can capture light that transmits through microchannel segment MS1 and deliver it to a photodetector, thus permitting analytical techniques such as absorption spectroscopy. Electrical wires EW1 and EW2 can connect to electrical components in chip 100, such as a thermistor to measure temperature, or the wires can connect to electrodes or other electrical components in channel MC1.

For microfluidic chip 100 and similar chips to be commercially feasible, the connections of microcapillaries, fiber optics, and wires must be reliable and automatable while still meeting stringent requirements such as precise alignment, small dead volumes, no voids, and low dispersion.

A microfluidic chip, such as chip 100, can comprise a central body structure in which the various microfluidic elements are disposed. The body structure can include an exterior portion or surface, as well as an interior portion which defines the various microscale channels, fluid mixing regions, and/or chambers of the overall microscale device. For example, the body structures of microfluidic chips typically employ a solid substrate that is typically planar in structure, i.e., at least substantially flat or having at least one flat surface. Suitable substrates can be fabricated from any one of a variety of materials, or combinations of materials. Typically, the planar substrates are manufactured using solid substrates common in the fields of microfabrication, e.g., silica-based substrates, such as glass, quartz, silicon, or polysilicon, as well as other known substrates, such as sapphire, zinc oxide alumina, Group III-V compounds, gallium arsenide, and combinations thereof. In the case of these substrates, common microfabrication techniques such as photolithographic techniques, wet chemical etching, micromachining, i.e., drilling, milling and the like, can be readily applied in the fabrication of microfluidic devices and substrates. Alternatively, polymeric substrates materials can be used to fabricate the devices described herein, including, e.g., polydimethylsiloxanes (PDMS), polymethylmethacrylate (PMMA), polyurethane, polyvinylchloride (PVC), polystyrene polysulfone, polycarbonate, polymethylpentene, polypropylene, polyethylene, polyvinylidine fluoride, ABS (acrylonitrile-butadiene-styrene copolymer), COC (cyclic olefin copolymers) and the like. In the case of such polymeric materials, laser ablation, injection molding, or embossing methods can be used to form the substrates having the channels and element geometries as described herein. In such cases, original molds can be fabricated using any of the above described materials and methods.

Figure 2A:
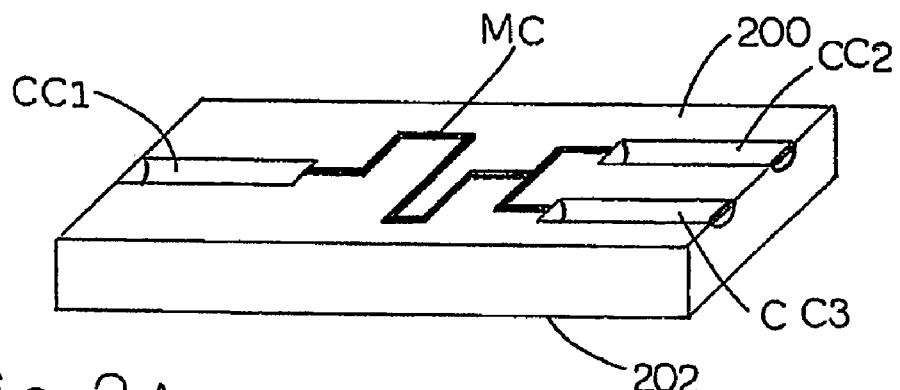
FIGS. 2A-2C illustrate views of different stages in assembly of a microfluidic chip and connection channels having a fluidic interconnection.
Figure 2B:
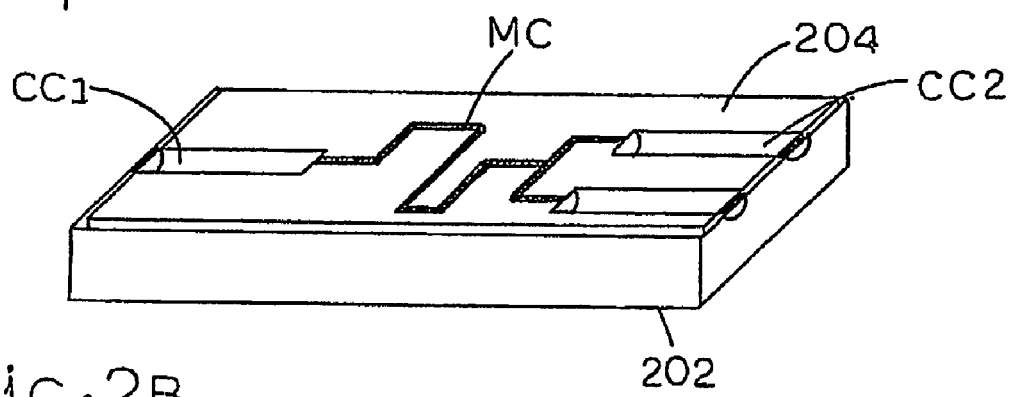
Figure 2C:
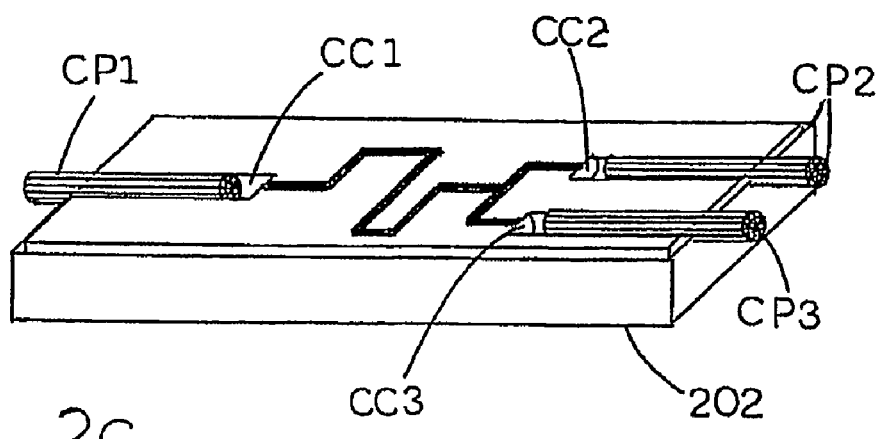

Referring to FIGS. 2A-2C, views of different stages in the assembly of a microfluidic chip and connection channels having at least one fluidic interconnection are illustrated. Microscale channels MC and similar structures (e.g. fluid mixing regions and chambers) can be fabricated into one surface 200 of a planar substrate 202, as grooves, wells, depressions, or other suitable configurations in that surface. Referring to FIG. 2B, a second planar substrate 204, typically prepared from the same or similar material, can be overlaid and bonded to the first, thereby defining and sealing the channels, mixing regions, and/or chambers of the device. Suitable techniques for bonding include thermal bonding, anodic bonding, gluing, or covalent bonding. Together, surface 200 of first substrate 202 and a lower mated surface of the upper substrate 204 define the interior portion of the device, i.e., defining the channels, fluid mixing junctions, and chambers of the device. Alternatively, the contacting surfaces of substrates 202 and 204 can be etched, embossed, or molded and mated together for defining an interior portion of the device.

Connection channels CC1, CC2, and CC3 can be formed between substrates 202 and 204. Connection channels CC1, CC2, and CC3 can attach and align capillaries, fiber optics, or wires to the microscale channel MC. Connection channels CC1, CC2, and CC3 can extend to the edge of substrate 202 and have diameters that are similar to the object to be connected. Referring to FIG. 2C, connection channels CC1, CC2, and CC3 can have diameters that are slightly larger than capillaries CP1, CP2, and CP3 inserted into channels CC1, CC2, and CC3, respectively. Alternatively, fiber optics or wires can be inserted into channels CC1, CC2, and CC3. The capillaries, fiber optics, and wires connected to a chip typically have larger diameters than the microfluidic channels on a chip, so connection channels typically have larger diameters than the microfluidic channels. Connection channels can be made at the same time, and using the same processes, as the microfluidic channels, for simplifying fabrication overall.

Figure 3A:
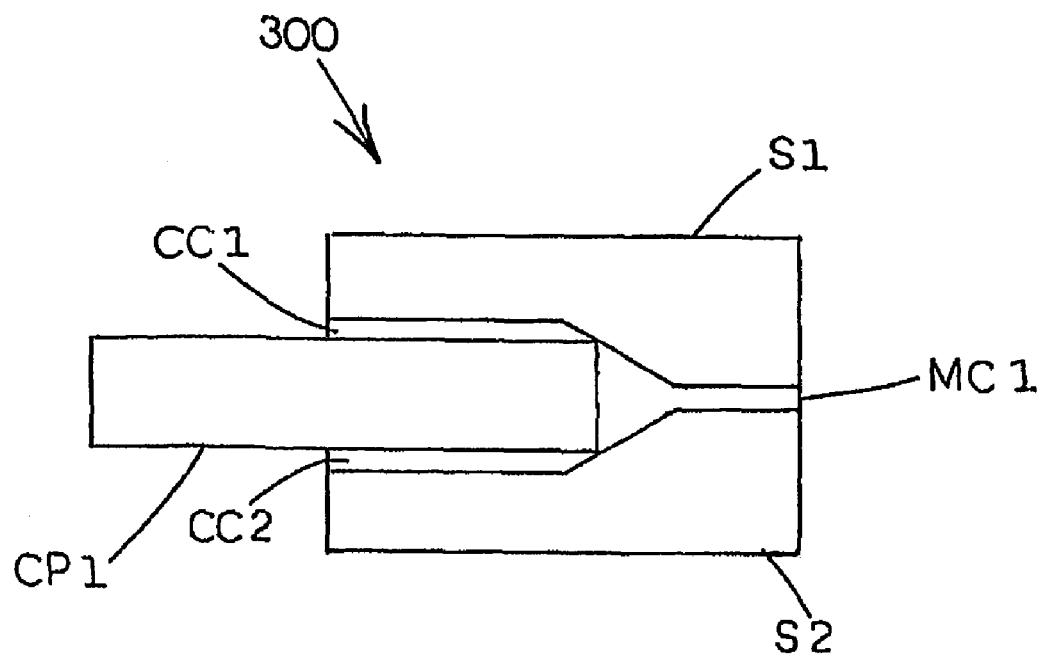
FIGS. 3A and 3B illustrate different cross-sectional side views of a capillary having a fluidic interconnection with a microfluidic chip.
Figure 3B:
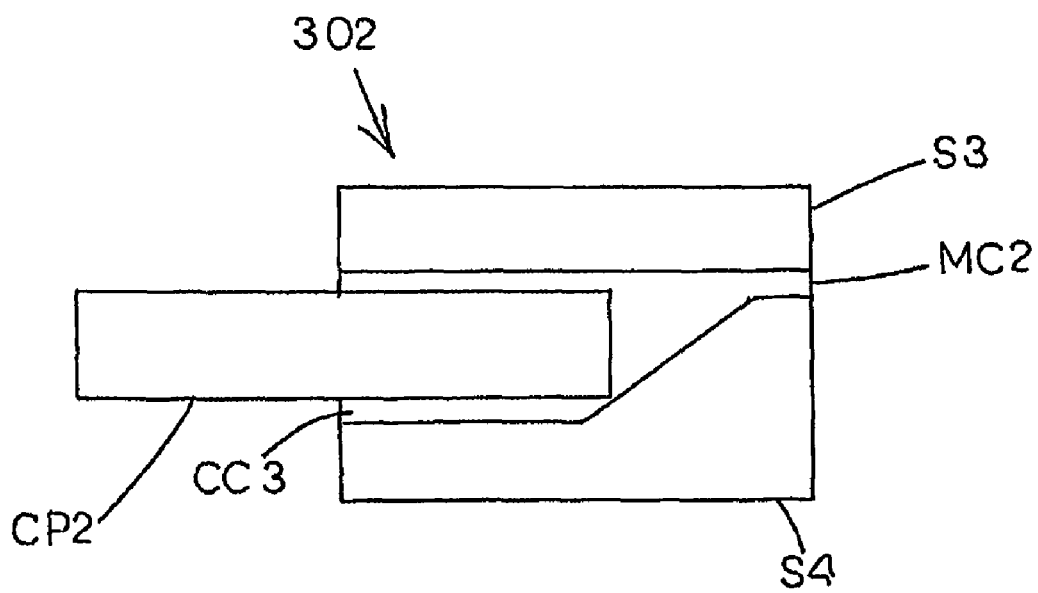

FIGS. 3A and 3B illustrate different cross-sectional side views of a capillary having a fluidic interconnection with a microfluidic chip. Referring specifically to FIG. 3A, a microfluidic chip, generally designated 300, can include a first and second connection channel CC1 and CC2 formed in a top and bottom substrate S1 and S2, respectively. Connection channels CC1 and CC2 form a single channel for receiving a capillary CP1 when substrate S1 and S2 are combined. Microfluidic chip 300 can also include a microscale channel MC1 having fluid connection with channels CC1 and CC2. A capillary CP1 can be inserted in channels CC1 and CC2 for delivering or receiving fluid from channel MC1. Capillary CP1 can be aligned with channel MC1 in this embodiment depending on the depths and shapes of channels CC1 and CC2. Alternative to capillary CP1, a fiber optic can be inserted in channels CC1 and CC2 for transmitting light into channel MC1.

Referring now to FIG. 3B, microfluidic chip, generally designated 302, can include substrates S3 and S4 having one connection channel CC3 formed in substrate S4. A capillary CP2 can be inserted in channels CC3 for delivering or receiving fluid from a channel MC2. In this embodiment, capillary CP2 is not aligned vertically with channel MC2.

Connection of a component, such as a capillary, fiber optic, or electrical wire, in a microfluidic chip (such as chips 300 and 302 shown in FIGS. 3A and 3B) can then be conducted by inserting the component into one or more connection channels (such as channels CC1, CC2, and CC3 shown in FIGS. 3A and 3B) and then bonding the capillary to the wall of the connection channel. Glue can be used for bonding the capillary to the wall of the connection channel.

Figure 4A:
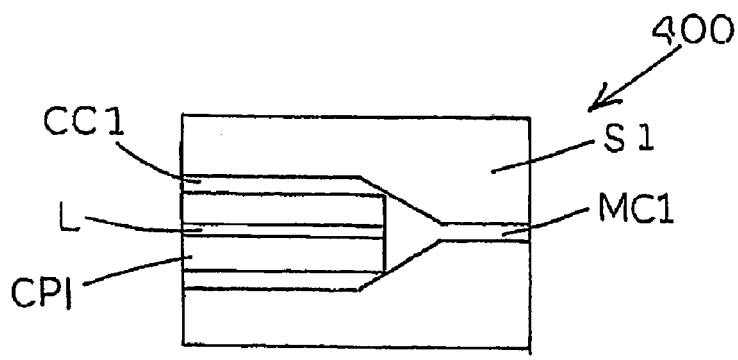
FIGS. 4A-4E illustrate different cross-sectional top views of glue used to attach a capillary inserted into a microfluidic chip.
Figure 4B:
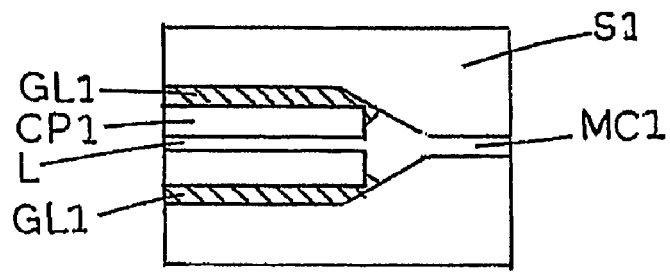

FIGS. 4A-4E illustrate different top views of a capillary inserted into a microfluidic chip in which the two substrates have been bonded to define and seal the microchannels similar to FIG. 2B. Referring specifically to FIG. 4A, a microfluidic chip, generally designated 400, can include a connection channel CC1 formed in a surface of a first and second substrate S1. Connection channel CC1 has two ends: the first end connects to a microchannel MC1 formed in substrate S1, and the second end is open at the edge of substrate S1; A capillary CP1 can be inserted into channel CC1 for connecting to microscale channel MC1. Referring now to FIG. 4B, capillary CP1 is shown affixed to microfluidic chip 400 with glue GL1. During assembly, capillary CP1 is first inserted into chip 400 and then glue GL1 is placed to form a mechanically rigid, fluid-tight seal between the surfaces of capillary CP1 and of connection channel CC1. In this embodiment, glue GL1 has completely filled the space between capillary CP1 and connection channels CC1 with no glue entering into microchannel MC1 or into lumen L of the capillary CP1. Alternatively, glue GL1 can fill some of the space at the leading edge of capillary CP1 to decrease dead volume.

Figure 4C:
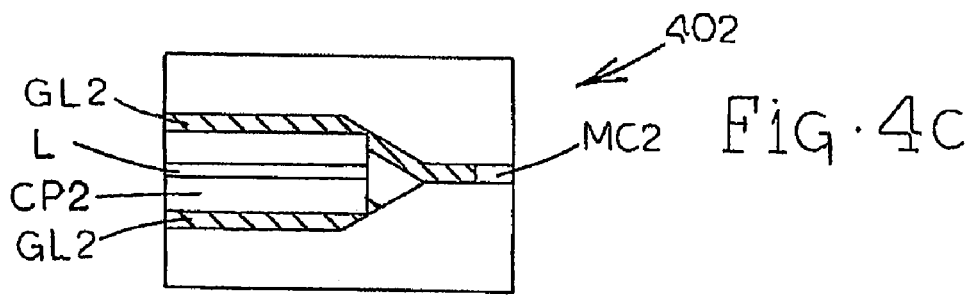
Figure 4D:
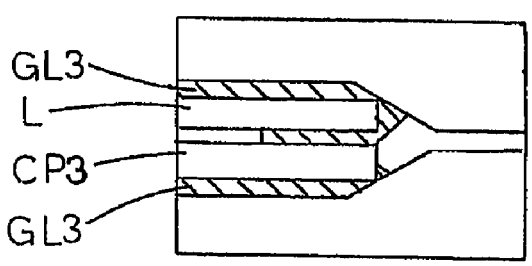
Figure 4E:
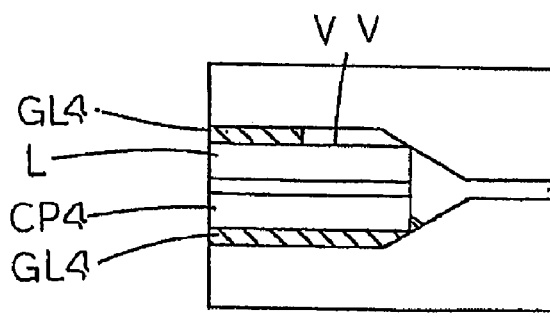

FIGS. 4C-4E illustrate microfluidic chips having failed connections to a capillary. FIG. 4C shows a microfluidic chip, generally designated 402, having a failed connection whereby glue GL2 extends beyond capillary CP2 and blocks microscale channel MC2. FIG. 4D shows a microfluidic chip, generally designated 404, having a failed connection whereby glue GL3 blocks lumen L of capillary CP3. FIG. 4E shows a microfluidic chip, generally designated 406, having a poor connection whereby the fluid passage between capillary CP4 and microscale channel MC3 is not blocked, but a large void volume VV runs down the side of the capillary CP3 in connection channel CC1 because glue GL4 does not fill connection channel CC1.

Figure 5A:
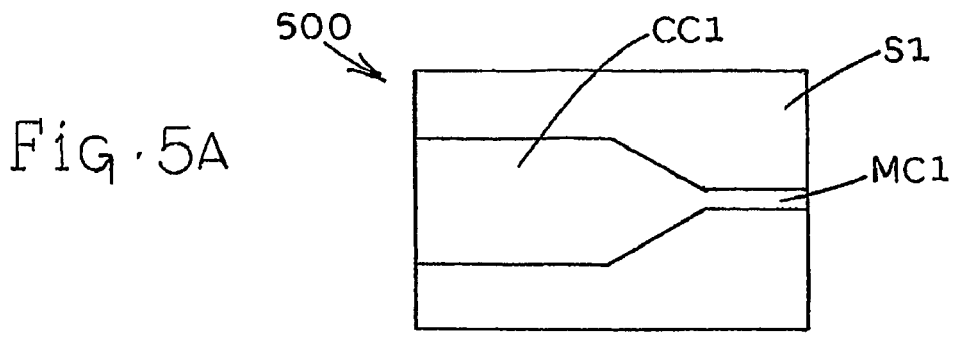
FIGS. 5A-5E illustrate views of different stages in the assembly of a microfluidic chip and connection channels having at least one fluidic interconnection.

Referring to FIGS. 5A-5E, top views of different stages in the assembly of a microfluidic chip and connection channels having at least one fluidic interconnection are illustrated. Referring specifically to FIG. 5A, a microfluidic chip, generally designated 500, having connection channel CC1 formed in substrate S1 can be provided. Connection channel CC1 can be connected to a microscale channel MC1. A second substrate (not shown) has been bonded over substrate S1 to enclose connection channel CC1 and microchannel MC1.

Figure 5B:
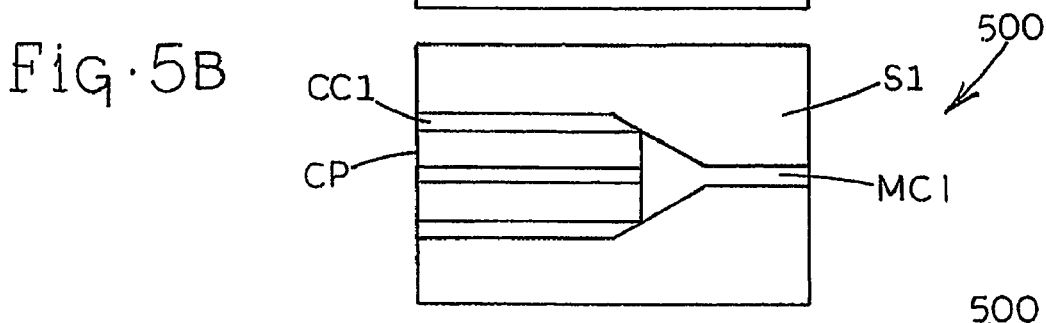

Referring to FIG. 5B, a capillary CP can be inserted into connection channel CC1 until it stops at the point that capillary CP meets the end of connection channel CC1.

Figure 5C:
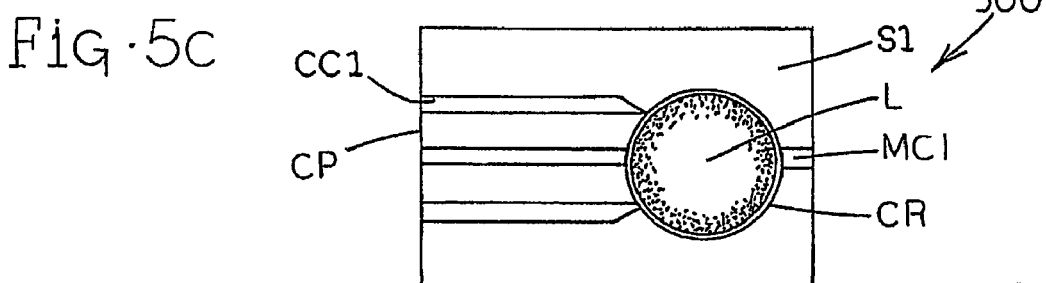
Figure 5D:
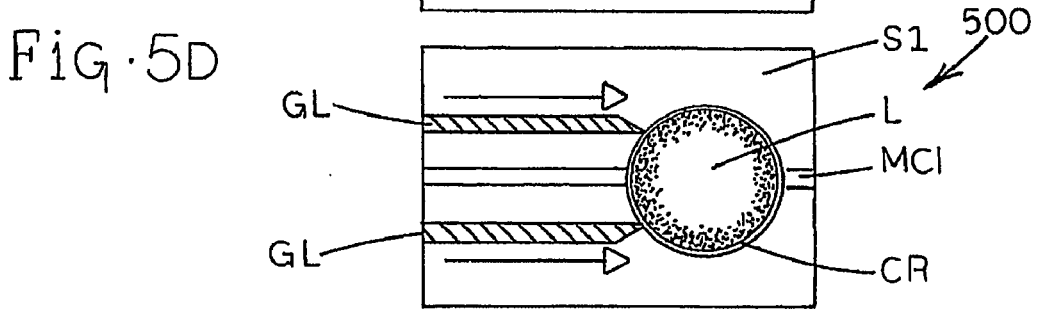
Figure 5E:
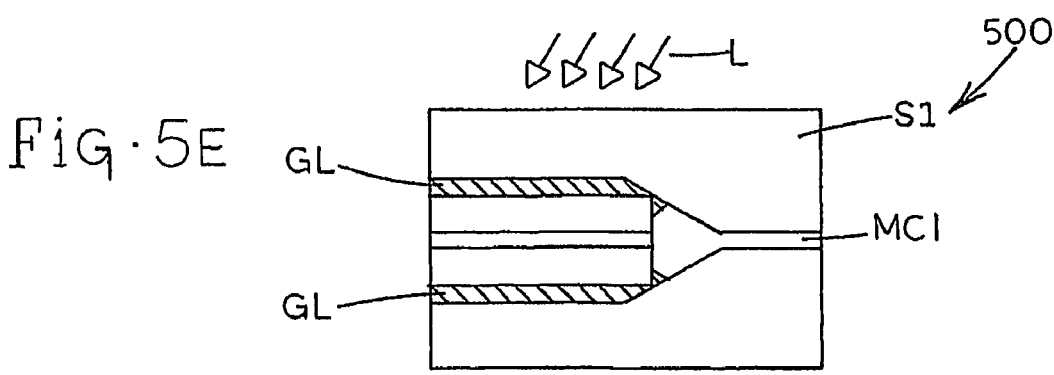

Referring to FIG. 5C, a beam of light L can shine into microfluidic chip 500 along an optical axis that is perpendicular to the plane of microfluidic chip 500. Beam of light L can be a laser beam that has been expanded to an appropriate diameter, or it can be the image of an aperture projected to focus at the connection channels CC1 by optics (not shown), or it can be the light from a light-emitting diode placed in close proximity to microfluidic chip 800. Referring to FIG. 5D, a light-curable glue GL can flow up connection channel CC1 filling the space between the wall of connection channels CC1 and capillary CP. Glue GL can be pumped in connection channels CC1 or it can be sucked up the connection channels by application of a vacuum, or it can advance by capillary action. Glue GL can flow up connection channel CC1 until its leading edge enters beam of light L whereupon it cures, thus halting the advance of glue GL. Referring to FIG. 5E, a larger portion of connection channel CC1 can be illuminated with light L to cure the rest of the glue GL for securing capillary CP to chip 500. Thus, a beam of light L is used to define the edges of the bond formed by glue GL, eliminating any errors in gluing shown in FIG. 4.

Glue GL can be light-curable and include any of a large number of UV-curable/UV-activated monomers and glues that polymerize or glue on irradiation by the appropriate wavelength of light. Examples of such glues include MASTER BOND® UV10 (available from Master Bond Inc. of Hackensack, N.J.), DYMAX®) 1128-M (available from Dymax Corporation of Torrington, Conn.), and LOCTITE® 3105 (available from Henkel Loctite Corp. of Rocky Hill, Conn.). Other glues that can be used are curable in the visible (400-700 nm) range. Alternatively, a focused beam of IR light can be used to cure heat-curable/heat-activatable glues.

One embodiment of the subject matter disclosed herein utilizes a microscope (such as the Model E800 microscope available from Nikon Inc. of Melville, N.Y.) configured for epifluorescence. The epifluorescence configuration includes a mercury arclamp, excitation filter, and beamsplitter that transmits UV light to the specimen plane. Microfluidic chip 500 can be made of polystyrene, polycarbonate, PMMA, Zeonor, or another transparent polymer or of glass or of quartz. The technique for fabrication for the microfluidic chip has little influence on fabrication of connections because capillary CP can be attached after fabrication of microfluidic chip 500. Microfluidic chip 500 can be placed on the microscope stage and positioned such that the connection channel CC1 and capillary CP are positioned in the field of view. The field diaphragm of the microscope is then focused onto the image plane and closed down to the appropriate diameter. The normal transmission illumination of the microscope permits visualization through an optically transparent microfluidic chip, allowing the operator to view all operations. The beam block for the epifluorescence pathway is opened, illuminating a circular region (designated CR in FIGS. 5C and 5D) at the end of capillary CP, and glue GL (such as UV monomer Model 3105 available from Henkel Loctite Corp.) can then be placed at the opening of the connection channels CC1 and CC2. Glue GL flows between the capillary CP and the wall of the connection channels CC1 and CC2 via capillary action and the leading edge cures on entering the UV-illuminated region CR (as shown in FIG. 5D). When glue GL has been cured all around capillary CP, the UV beam is moved along all of the connection channels CC1 and CC2 to partially cure all glue GL, making the connection more mechanically stable. Microfluidic chip 500 can then be transferred to a UV curing oven (such as UV curing oven Model ELC500 available from Electro-Lite Corporation of Danbury, Conn.) and UV baked for another 10 minutes to fully cure the UV monomer. Connection of a fiber optic or of a wire can be accomplished by similar methods.

Figure 6:
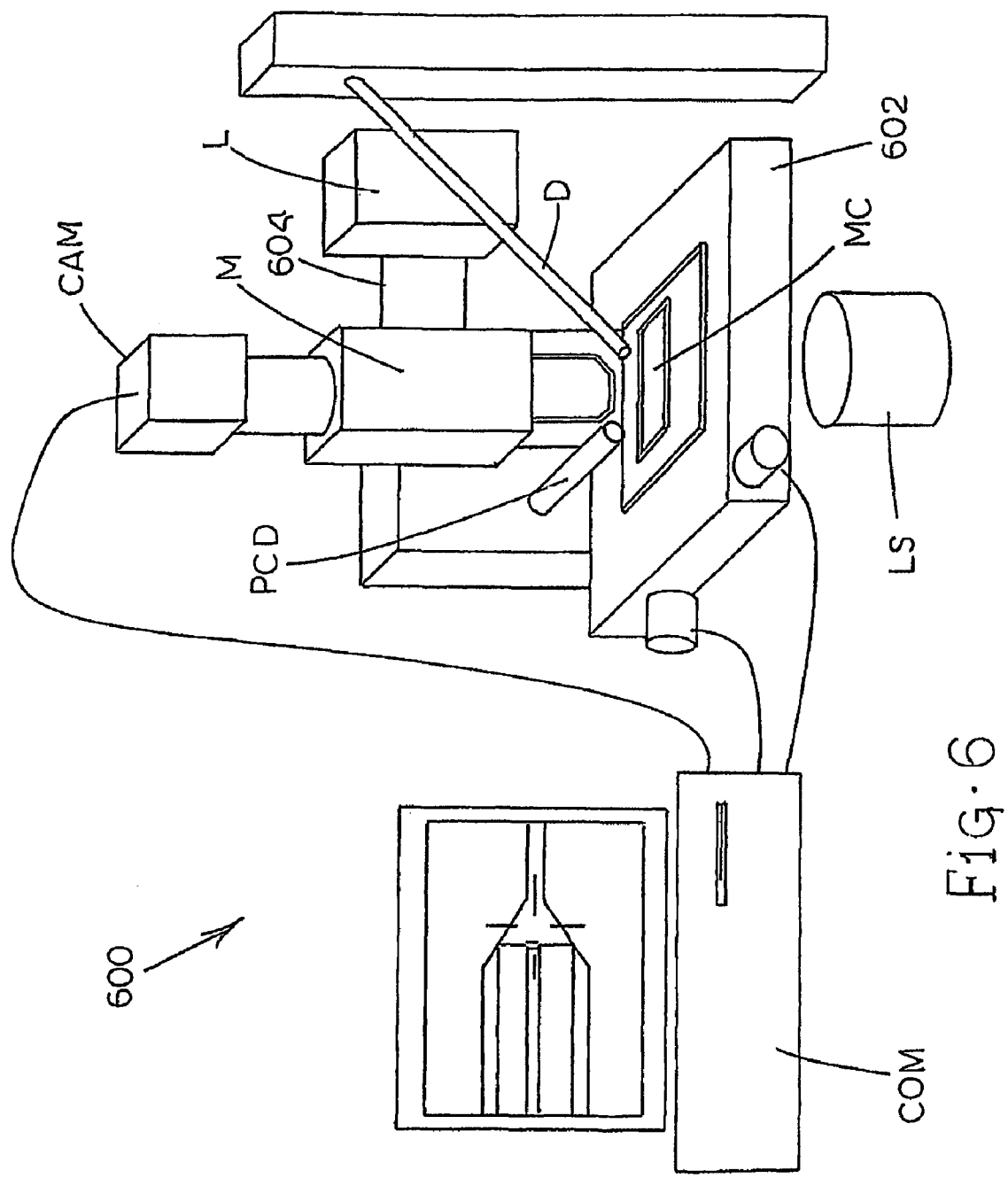
FIG. 6 illustrates a perspective view of a system for automating connection fabrication.

This technique for creating connections can be automated in a fashion similar to that used to wirebond the dye of an integrated circuit into a DIP package. FIG. 6 illustrates a perspective view of a system, generally designated 600, for automating connection fabrication. A microfluidic chip MC (such as chip 500 shown in FIGS. 5A-5E) can be placed on an open frame XY-stage 602 with optical encoder feedback (e.g., the BioPrecision Stage controlled by the MAC5000 controller available from Ludl Electronic Products, Ltd. of Hawthorne, N.Y., U.S.A.) and controlled by a computer COM. System 600 can include a microscope M for sending a magnified view of chip MC to a camera CAM. The image from camera CAM can then be as captured by computer COM. Microfluidic chip MC has fiducial marks included as part of its fabrication to permit camera CAM and computer COM to precisely determine the position and angular orientation of chip MC relative to stage 602. An arclamp or laser L can provide light for curing glue (such as glue GL shown in FIGS. 5A-5E) in chip MC. System 600 can include a shutter 604 under computer control for illuminating the connection with light. System 600 can include a precision capillary dispenser PCD for inserting a capillary (such as capillary CP1 shown in FIGS. 5A-5E) into connection channels (such as connection channels CC1 and CC2 shown in FIGS. 5A-5B) of chip MC until the capillary abuts the end of connection channel. Precision glue dispenser D can dispense light-curable monomer or glue at the opening of the connection channel. System 600 can also include a light source LS for broadly illuminating the connection channel with light to cure glue in the entire connection channel after the leading edge of the glue has been cured by the light beam at the front edge of the capillary.

Figure 7:
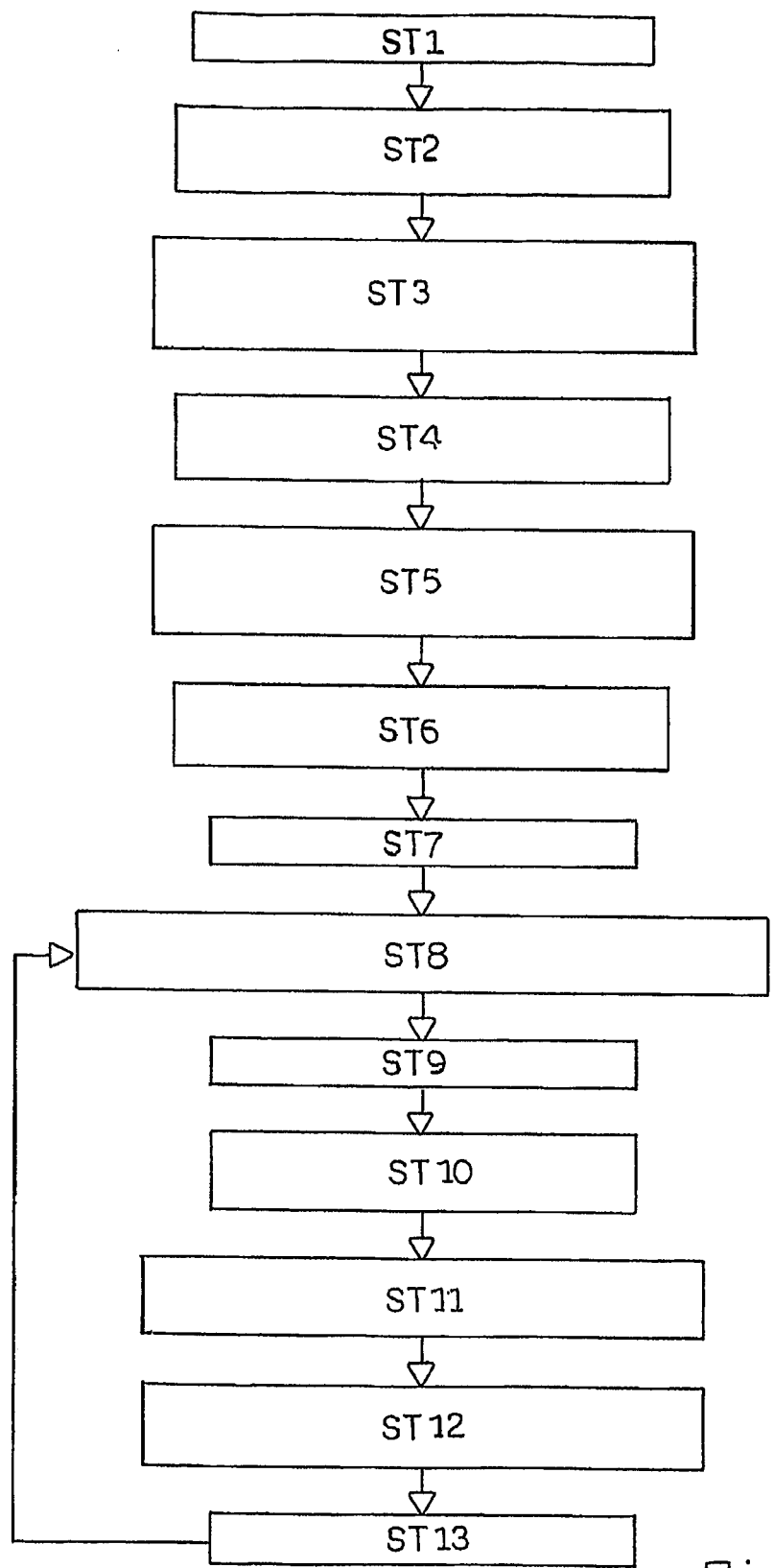
FIG. 7 is a flow chart of steps for automated gluing of connections using a system for automating connection fabrication.

FIG. 7 illustrates a flow chart of steps for automated gluing of connections using a system for automating connection fabrication (such as system 600 shown in FIG. 6). Initially, at step ST1, a microfluidic chip (such as microfluidic chip MC shown in FIG. 6) can be placed on an open frame XY-stage (such as stage 602 shown in FIG. 6). Next, at step ST2, a computer (such as computer COM shown in FIG. 6) can instruct the stage to move to the approximate position of fiducial mark #1 as indicated on the chip. The computer can auto-focus a microscope (such as microscope M shown in FIG. 6), video match an image of fiducial mark #1 via image processing (two-dimensional cross-correlation), and record the coordinates (step ST3). Next, at step ST4, the computer can instruct the stage to move to the approximate position of fiducial mark #2 as indicated on the chip. The computer can auto-focus a microscope, video match an image of fiducial mark #2 via image processing (two-dimensional cross-correlation), and record the coordinates (step ST5). At step ST6, the computer determines the coordinates $(X_0Y_0)$ and rotation for the microfluidic chip based on fiducial marks #1 and #2. This orients microfluidic chip MC for the computer which can now instruct the stage to move to predetermined locations, such as the connection of a capillary (such as CP shown in FIG. 5C) and microscale channel (such as microscale channel MC1 shown in FIG. 5C). Next, at ST7, the computer can direct the stage to move to the connection of the capillary and microscale channel.

Next, the process begins a loop beginning at step ST8 for positioning and affixing a predetermined number of capillaries to appropriate connection channels. Referring to FIG. 7, at step ST8, a precision capillary dispenser (such as precision capillary dispenser PCD shown in FIG. 6) can insert the capillary until its end abuts the end of the connection channel or channels. At step ST9, a shutter (such as shutter 604 shown in FIG. 6) of the microscope can be opened. Next, glue (such as glue GL shown in FIGS. 5A-5E) can be dispensed by a capillary dispenser (such as precision capillary dispenser PCD shown in FIG. 6) into the connection channel (step ST10). An appropriate amount of time is waited for glue to advance to the location of circular region (such as circular region CR shown in FIGS. 5C and 5D) of a light beam emitted by microscope (step ST11). Alternatively, computer COM can analyze the image to determine when the glue has advanced to the location of circular region CR. Next, a broadly illuminating beam from microscope is directed to cure all the glue (step ST12). At step ST13, the process returns to step ST8 if there are more connections.

If the capillary or fiber optic to be connected to the microfluidic chip (such as microfluidic chip 300) can transmit the light for curing, then illumination of the glue can be achieved by shining the light into the fiber optic or capillary. This has the advantage that the light emanates from the end of the capillary or optic as a circular beam of light that expands with the numerical aperture of the fiber optic. This creates a circular "wall" of light emanating from the fiber optic through which uncured glue cannot flow.

FIGS. 8A-8E illustrate views of different stages in the assembly of a microfluidic chip and connection channels by transmitting light through a connection channel for curing glue. Referring specifically to FIG. 8A, a microfluidic chip, generally designated 800, having a connection channel CC connected to a microscale channel MC is provided. Microfluidic chip 800 can be made of polystyrene, polycarbonate, Poly(methyl methacrylate) (PMMA), Zeonor, or other transparent polymer, or of glass, or of quartz. Connection channel CC is formed by a first and second substrate S1 and S2. Referring to FIG. 8B, a capillary CP can be inserted in connection channel CC. Capillary CP can be made of a UV-transmitting fused silica light guide/capillary available from Polymicro Technologies L.L.C. of Phoenix, Ariz.

Referring to FIG. 8C, light can be directed into capillary CP such that it emanates from the end of capillary CP in the connection channel CC. Light L1 can emanate from the light-guiding capillary CP to form a cone of light that creates a wall of light at the end of capillary CP. Light L1 can be introduced into capillary CP by directing the beam of a HeCd laser (such as the Series 56 Omnichrome available from Melles Griot BV of Carlsbad, Calif.) into the free end of the capillary.

Referring to FIG. 8D, light-curing glue GL can flow along connection channel CC toward the end of capillary CP. Glue GL can be Model 3105 available from Henkel Loctite Corp. When the leading edge of glue GL enters the cone of illumination of light L1, glue GL is cured. The further advance of glue GL can be halted by the curing. Referring to FIG. 8E, a second light L2 can then be directed along all of connection channel CC to cure all of the glue GL filling the space between capillary CP and the wall of the connection channel CC.

Alternatively, microfluidic chip 800 can be made of opaque materials, such as metal or silicon, when cure light is transmitted by the capillary or fiber optic. In this case, subsequent cure of the glue GL distant from the end of the capillary requires either injection of light into the gap between the capillary CP and the wall of the connection channel CC or a secondary curing technique, such as heat or time.

Connection of a fiber optic can be accomplished with similar methods. If substrate S1 of microfluidic chip 800 is sufficiently transparent to the wavelengths of light carried by the fiber optic during use of chip 800, then connection of the fiber optic does not require that the face of the fiber optic be in direct contact with fluid inside microfluidic channel MC. A small layer of substrate S1 can remain separating microfluidic channel MC from the front face of the fiber optic.

A light-guiding conduit frequently comes with a sheath of polyimide (such as light-guiding capillaries available from Polymicro Technologies L.L.C. of Phoenix, Ariz.). It may not be necessary for this polyimide sheathing to be removed. The sheathing can be left on whereby it acts as a light barrier, e.g. for UV light, that leaks from the light-guiding capillary, thereby preventing this light from prematurely curing the glue GL in the connection channel CC. Alternatively, a light-guiding conduit can be coated with another opaque material to prevent premature curing of the glue GL in the connection channel CC by light leaking from the light-guiding conduit.

Post-processing of the glue can be performed to achieve an interconnect that is more chemically compatible with the fluids intended for use in the final microfluidic system. For example, many acids or organic solvents will swell or chemically attack a polymer glue. A sinterable material, such as a glass-filled UV-curable glue, can be used to glue to capillary or fiber optic. Subsequent sintering of the assembly will remove the polymer and anneal the glass. Thus, for example, a microfluidic device, capillary, and interconnect can be formed entirely of glass.

Figure 9A:
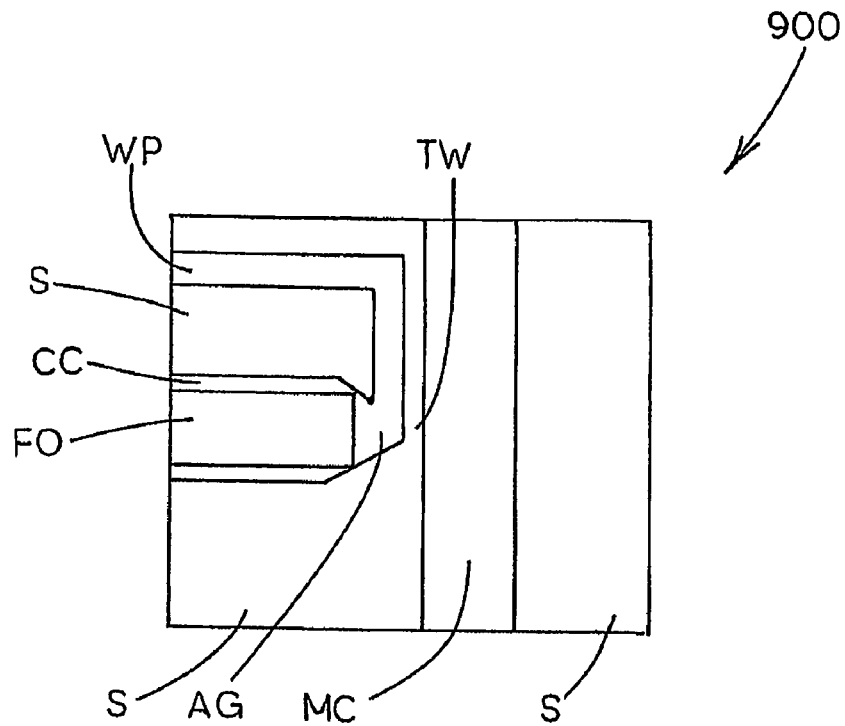
FIGS. 9A and 9B illustrate top views of different stages in the assembly of a microfluidic chip and connection channels.
Figure 9B:
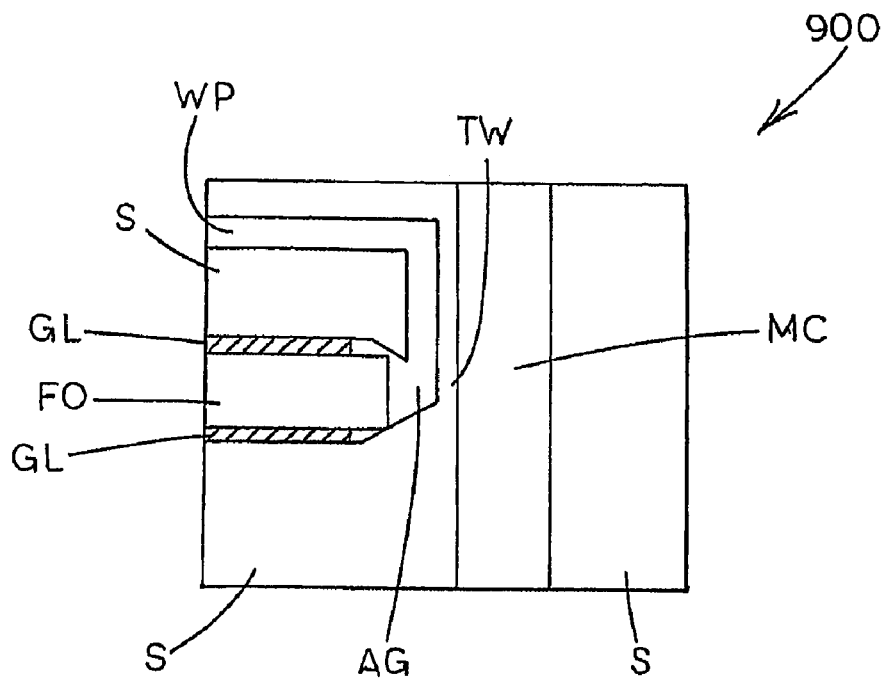

FIGS. 9A and 9B illustrate top views of different stages in the assembly of a microfluidic chip and connection channels. Referring specifically to FIG. 9A, a microfluidic chip, generally designated 900, can be made of a substrate S forming a microscale channel MC, a weep channel WP, and a connection channel CC. Connection channel CC can be separated by a thin wall TW from microscale channel MC. A fiber optic FO can be inserted into connection channel CC and affixed with glue GL using any of the techniques described above. Weep channel WC can permit air to escape from the end of the connection channel CC as glue GL flows up connection channel CC.

According to one embodiment, an air gap AG can be formed between fiber optic FO and thin wall TW. This can be advantageous if separate optical components are desired at the end of fiber optic FO. Referring to FIG. 9B, glue GL can be advanced and stopped at the front face of the fiber optic FO. This permits formation of an air gap AG between the fiber optic FO and the wall TW. Optical components (such as waveguides, diffraction gratings, microlenses and other suitable optical components known to those of skill in the art) attached to the end of FO can be positioned in air gap AG.

According to an alternate embodiment, no air gap AG is formed. If glue GL is sufficiently transparent to the wavelengths of light carried by the fiber optic during use of chip 800, then glue GL can be allowed to flow past the end of the fiber optic prior to curing of glue GL. If the refractive index of glue GL matches the refractive index of substrate S, then glue GL and substrate S will behave optically like an index-matching immersion fluid connecting fiber optic FO to fluid transmitted in microfluidic channel MC.

Figure 10A:
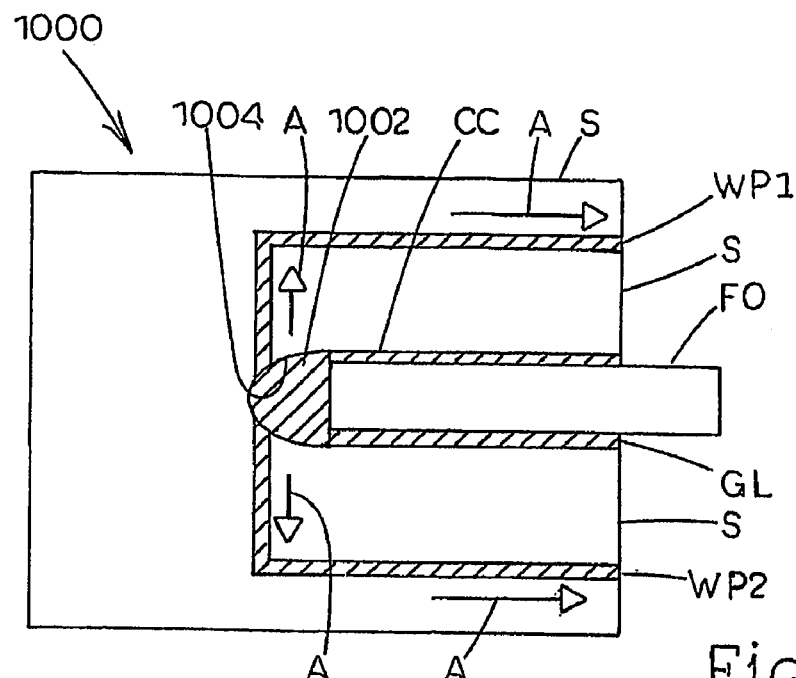
FIGS. 10A-10C illustrate different views of exemplary microfluidic systems having optical components integrated therein.
Figure 10B:
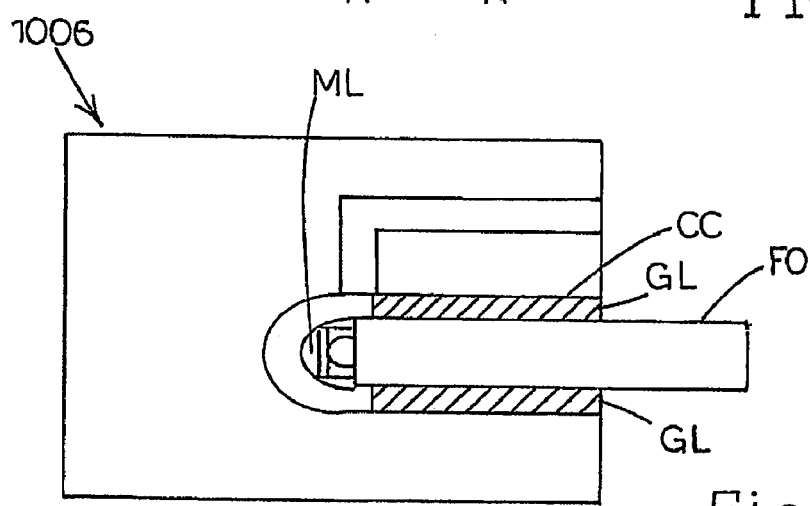
Figure 10C:
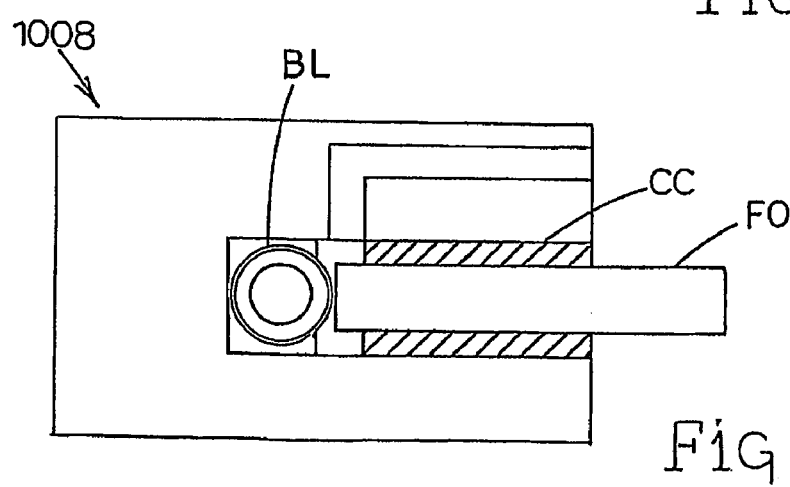

FIGS. 10A-10C illustrate different views of exemplary microfluidic systems having optical components integrated therein. Referring specifically to FIG. 10A, a microfluidic system, generally designated 1000, can include a lens 1002 formed by the shape of a connection channel CC and glue GL that fills the space between an end surface 1002 of fiber optic FO and an end surface 1004 of connection channel CC. The shape of connection channel CC and the refractive index of glue GL can be selected to provide a lens of desired optical power. System 1000 can include a substrate S having connection channel CC and weep channels WP1 and WP2 formed therein. End 1004 of connection channel CC can be etched concave so that lens 1002 can be formed therein. Next, a top substrate (not shown) can be bonded to substrate S to enclose connection channel CC and weep channels WP1 and WP2.

When fiber optic FO is positioned as shown in FIG. 10A, a glue GL of appropriate refractive index (e.g., a UV-curable monomer) can be flowed in the direction of the gray arrows through the connection channel CC and weep channels WP1 and WP2. Glue GL can fill the convex portion of connection channel CC, and in so doing, forms lens 1002. If glue GL can be cured to form a solid, lens 1002 can form a solid lens. Alternatively, lens 1002 can be used in liquid form, and various liquids with different refractive indices can be used to adjust the focal length of lens 1002.

Referring now to FIG. 10B, a microfluidic system, generally designated 1006, can include a microlens ML attached to a fiber optic FO prior to inserting fiber optic FO into a connection channel CC. After insertion of fiber optic FO, fiber optic FO can be affixed into place as shown in FIG. 10B with light-curable glue GL. Alternatively, the fiber optic FO can be affixed by simply adding a self-curing glue, such as epoxy, at the opening of connection channel CC, or fiber optic FO can be bonded using one of the thermal bonding processes described below.

Referring to FIG. 10C, a microfluidic system, generally designated 1008, can include a ball lens BL integrated with fiber optic FO inserted in a connection channel CC. Ball lens BL can be a loose component integrated with fiber optic FO by inserting it into connection channel CC prior to placement of fiber optic FO. Next, ball lens BL can be then pushed to the end of connection channel CC, as shown in FIG. 10C, with the fiber optic FO. Connection channel CC can serve to align ball lens BL and fiber optic FO. Alternatively, fiber optic FO can be glued by simply adding a self-curing glue GL, such as epoxy, at the opening of connection channel CC, or fiber optic FO can be bonded using one of the thermal bonding process described below.

Figure 11A:
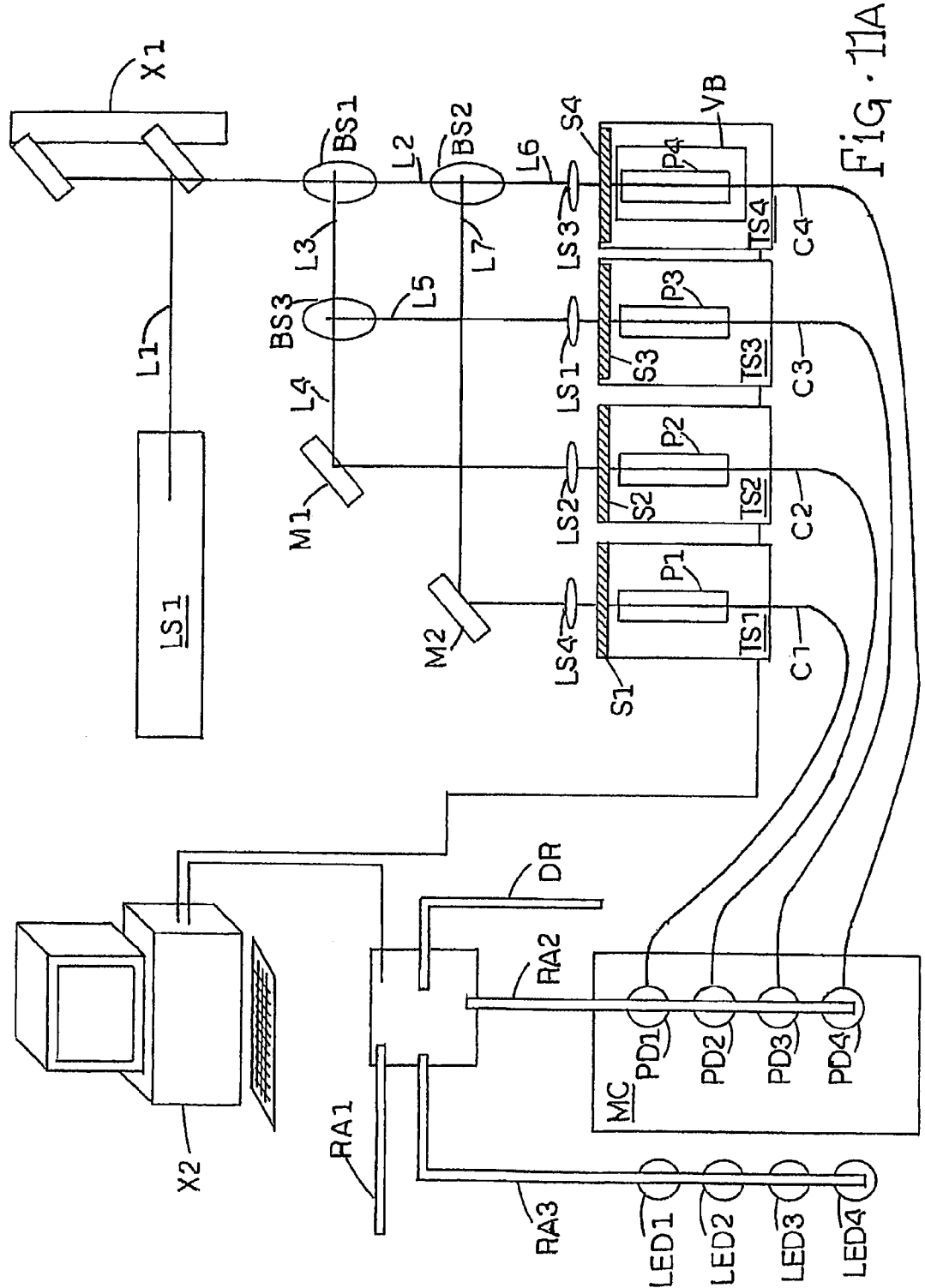
FIG. 11A illustrates a schematic diagram of a system for automating the process of attaching a capillary or optic fiber to a connection channel by transmitting light through the capillary or optic fiber to cure glue.

FIG. 11A illustrates a schematic diagram of a system 1100 for automating the process of attaching a capillary or optic fiber to a connection channel by transmitting light through the capillary or optic fiber to cure glue. This automated process can be used in a process such as the process described with regard to FIG. 8. System 1100 can include a light source LS1 operable to project a beam of light L1 to a beam-steerer 30. In one embodiment, light source LS1 is a laser, such as the Melles Griot 51 Series UV laser available from Melles Griot BV. The beam-steerer can direct light beam L1 to beamsplitter BS1. Beamsplitter BS1 can split light L1 into beams of light L2 and L3 and direct light L2 and L3 to beamsplitters BS2 and BS3, respectively. Beamsplitters BS2 can split light L2 into beams of light L4 and L5. Light L4 and L5 can be directed to a mirror M1 and lens LS1, respectively. Mirror M1 can direct light L4 to a lens LS2. Beamsplitter BS3 can split light L3 into beams of light L6 and L7 and direct light L6 and L7 to lens LS3 and mirror M2, respectively. Mirror M2 can direct light L7 to a lens LS4. Lenses LS1, LS2, LS3, and LS4 can focus light L5, L4, L6, and L7, respectively, to an intense spot for insertion of light into an end of fiber optics or light-guiding capillaries C1, C2, C3, and C4, respectively. Similar optical trains can be used to split the light beam into a plurality of beams sufficient to allow one beam to impinge upon a plurality of fiber optics or light-guiding capillaries.

Positioners P1, P2, P3, and P4 can hold the ends of capillaries C1, C2, C3, and C4. Stops S1, S2, S3, and S4 can provide a solid "wall" to which capillaries C1, C2, C3, and C4 can abut to ensure that the capillaries are aligned at or near the focal point of lenses LS1, LS2, LS3, and LS4, respectively. Stops S1, S2, S3, and S4 can be made of any suitable transparent material that is transparent to the wavelength of light beams L4, L5, L6, and L7. In one embodiment, the stops may be made of glass and/or quartz. Capillaries C1, C2, C3, and C4 can be inserted into the connection channels (not shown) of a microfluidic chip MC. A robotic arm RA can automate insertion of capillaries C1, C2, C3, and C4 into positioners P1, P2, P3, and P4 and the connection channels of microfluidic chip MC. Light L1 can be turned on and glue (not shown) dispensed by a glue dispensing robot DR. After sufficient time has elapsed for the glue to flow into the connection channels and be cured at the end of fiber optics C1, C2, C3, and C4, a broader beam of light from another light source LS2 can be turned on to cure the rest of the glue in all of the connection channels in microfluidic chip MC.

Detectors PD1, PD2, PD3, and PD4 can be positioned above the connection channels of microfluidic chip MC. In one embodiment, detectors PD1, PD2, PD3, and PD4 are attached to robotic arm RA1 to allow the detectors to be automatically moved in and out of position above the connection channels. In another embodiment, the detectors are photodiodes such as the JIC 149L photodiode available from Boston Electronics Corporation of Boston, Mass., U.S.A. In one embodiment, the robotic arm is on a Carvo RSP 9000 robot. Light L1 can be turned on and light can be detected by the detectors as it exits capillaries C1, C2, C3, and C4.

In another embodiment, positioners P1, P2, P3, and P4 are attached to motorized translation stages TS1, TS2, TS3, and TS4. In one embodiment, translation stages TS1, TS2, TS3, and TS4 are motorized with NewFocus closed and/or open-loop Picomotors. Feedback from detectors PD1, PD2, PD3, and PD4 fed through a computer or microcontroller 31 can be used to move translation stages TS1, TS2, TS3, and TS4 to optimize the light detected by detectors PD1, PD2, PD3, and PD4. After light throughput has been optimized, glue (not shown) can be dispensed by a glue dispensing robotic arm RA2.

Controller 31 now waits a sufficient time for the glue to flow into the connection channels and be cured at the end of capillaries C1, C2, C3, and C4. If the glue does not wick up the connection channels, a vacuum may be applied to one or more capillaries by pulling a vacuum on a capillary end contained within a vacuum box (not shown). The vacuum helps suck the glue up the connection channels. After the glue has reached the end of the connection channels and the advancing glue front has been cured, a broader beam of light from another light source can be turned on to cure the rest of the glue in all of the connection channels in microfluidic chip MC. In one embodiment, this broader beam of light is also controlled by a robotic arm RA3. In one embodiment, the broader light beam is produced by a plurality of UV light-emitting diodes LED1, LED2, LED3, and LED4, such as MegaBright UV LEDs available from Cree, Inc. of Durham, N.C., U.S.A.

Figure 11B:
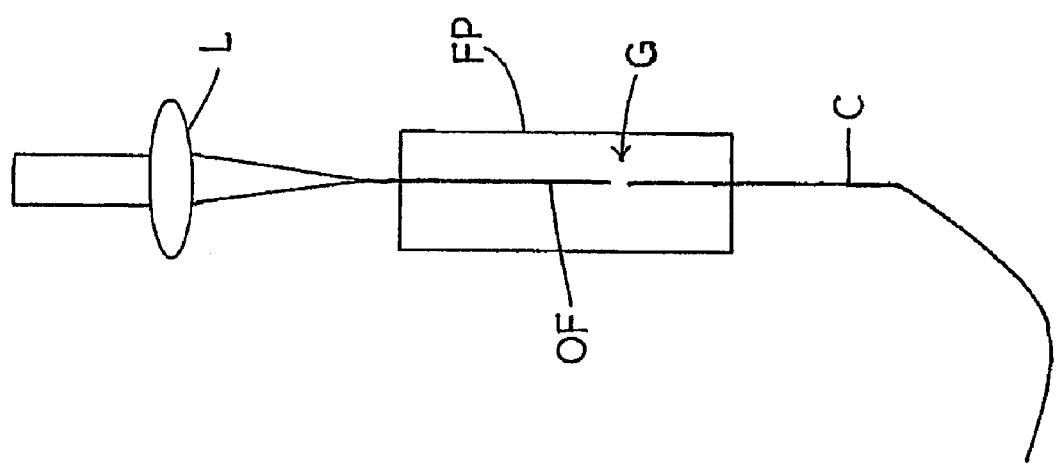
FIG. 11B is a schematic diagram of an apparatus for coupling a capillary and an optical fiber for light transmission according to one embodiment.

FIG. 11B illustrates a schematic diagram of an apparatus for coupling a capillary C and an optical fiber OF for light transmission according to one embodiment. A short span of optical fiber FO having the same numerical aperture as capillary C is permanently affixed to a fiber positioner FP. The end of optical fiber FO is placed at the focal point of lens L. Capillary C can be butt-coupled to optical fiber OF within fiber positioner FP. By ensuring that the gap is small, light can be achieved between the two optical fibers. A small gap, generally designated G, can be provided between capillary C and optical fiber FO. An advantage of this system is that no feedback or motor control is required.

Figure 11C:
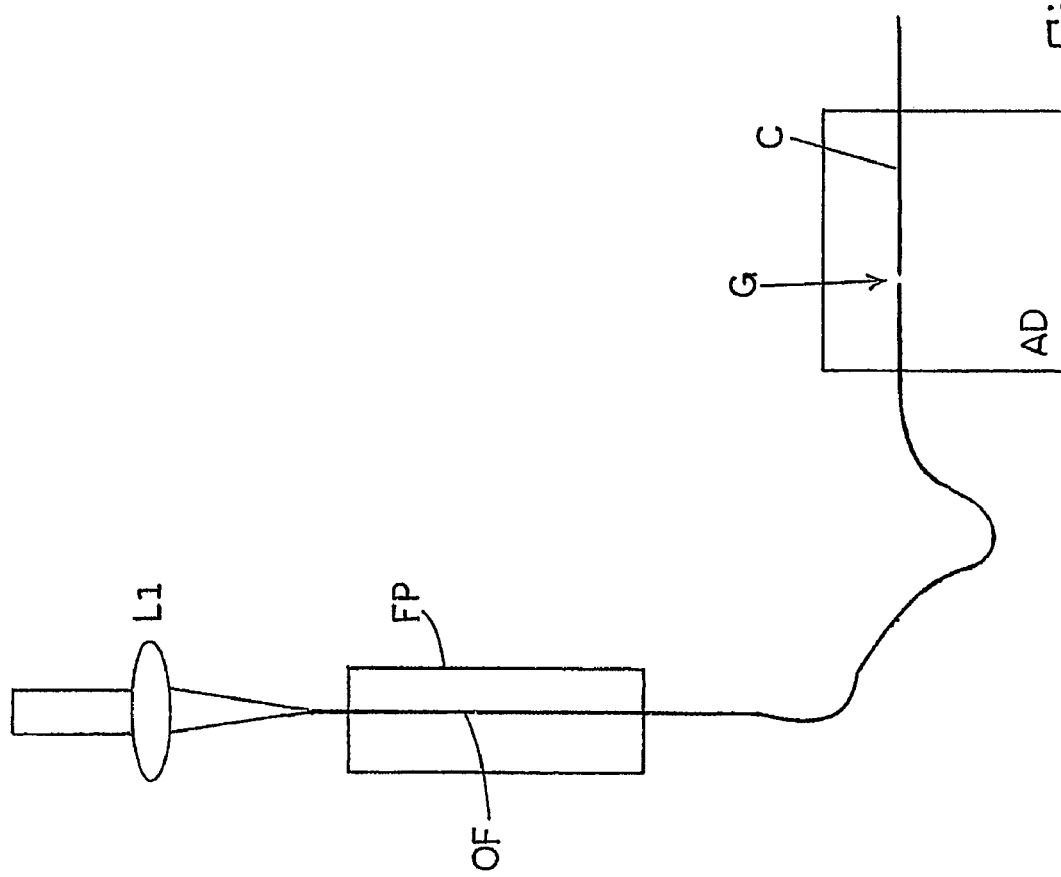
FIG. 11C is a schematic diagram of another apparatus whereby a fixed optical fiber extends beyond a fiber positioner and its free end is positioned into an alignment device.

FIG. 11C illustrates a schematic diagram of another apparatus whereby a fixed optical fiber OF extends beyond a fiber positioner FP and its free end is positioned into an alignment device AD. One end of optical fiber OF that is to be cured to a microfluidic chip (not shown) is also placed into alignment device AD where it is butt-coupled to a fixed capillary C. Alignment device AD can align optical fiber OF and capillary C so that they are optimally aligned. According to one embodiment, alignment device AD can be a fusion splicer such as the Type 65 alignment fusion splicer available from Sumitomo Electric Lightwave Corp. of Research Triangle Park, North Carolina, U.S.A. Using the fusion splicer, a plurality of optical fibers or capillaries/fibers can be aligned simultaneously, by aligning the outside diameters of the capillaries or fibers. Other suitable alignment techniques can also be utilized. After alignment, a small gap, generally designated G, between capillary C and optical fiber OF may occur. By ensuring that gap G is small, adequate coupling can be achieved by capillary C and optical fiber OF.

Figure 12:
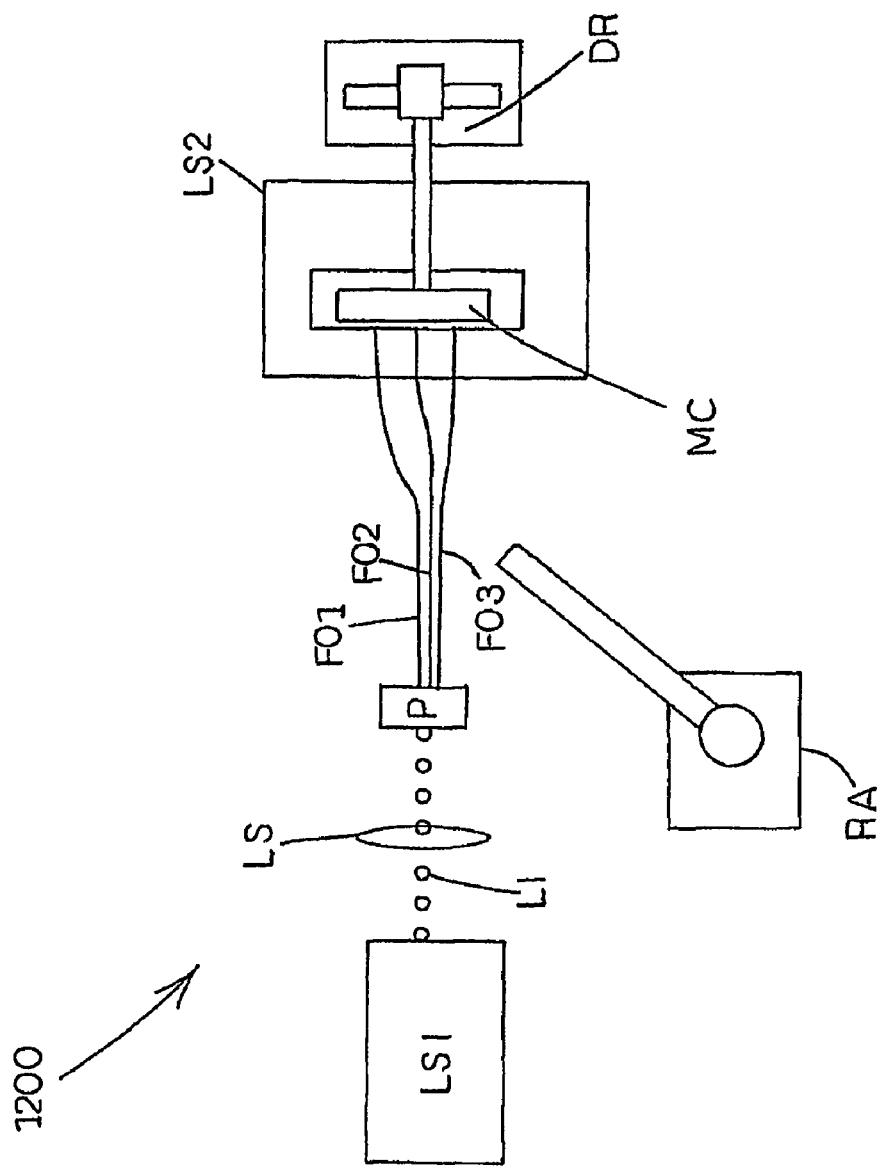
FIG. 12 illustrates a schematic diagram of another system for automating the process of attaching a capillary or optic fiber to a connection channel by transmitting light through the capillary or optic fiber to cure glue.

FIG. 12 illustrates a schematic diagram of another system 1200 for automating the process of attaching a capillary or optic fiber to a connection channel by transmitting light through the capillary or optic fiber to cure glue. System 1200 can include a light source LS1 operable to project a beam of light L1 toward lens LS. Lens LS can focus light L1 to an intense spot for insertion of light L1 into fiber optics FO1, FO2, and FO3. Lens LS can be a refracting lens that focuses light L1 to a single spot, or it can be a diffracting optic capable of focusing light L1 to multiple spots at the ends of fiber optics FO1, FO2, and FO3. Fiber optics FO1, FO2, and FO3 can be bundled together such that their free ends are held together by a positioner P at the focal point of lens LS. The fiber optics FO1, FO2, and FO3 can be inserted into the connection channels (not shown) in a microfluidic chip MC. System 1200 can include a robotic arm RA operable to automate insertion of fiber optics FO1, FO2, and FO3 into positioner P and the connection channels of microfluidic chip MC.

Light L1 can be turned on and glue (not shown) can be dispensed by a glue dispensing robot DR. After sufficient time has elapsed for the glue to flow into the connection channels and be cured at the end of fiber optics FO1, FO2, and FO3, a broader beam of light from light source LS2 can be turned on to cure the rest of the glue in all of the connection channels in microfluidic chip MC.

Figure 13A:
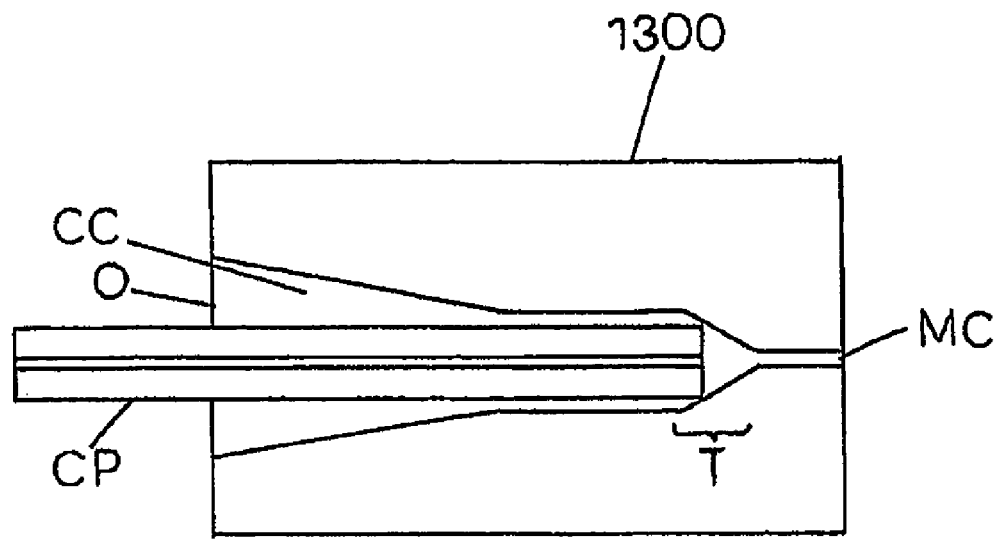
FIGS. 13A and 13B illustrate top views of a microfluidic chip for facilitating insertion of capillaries.
Figure 13B:
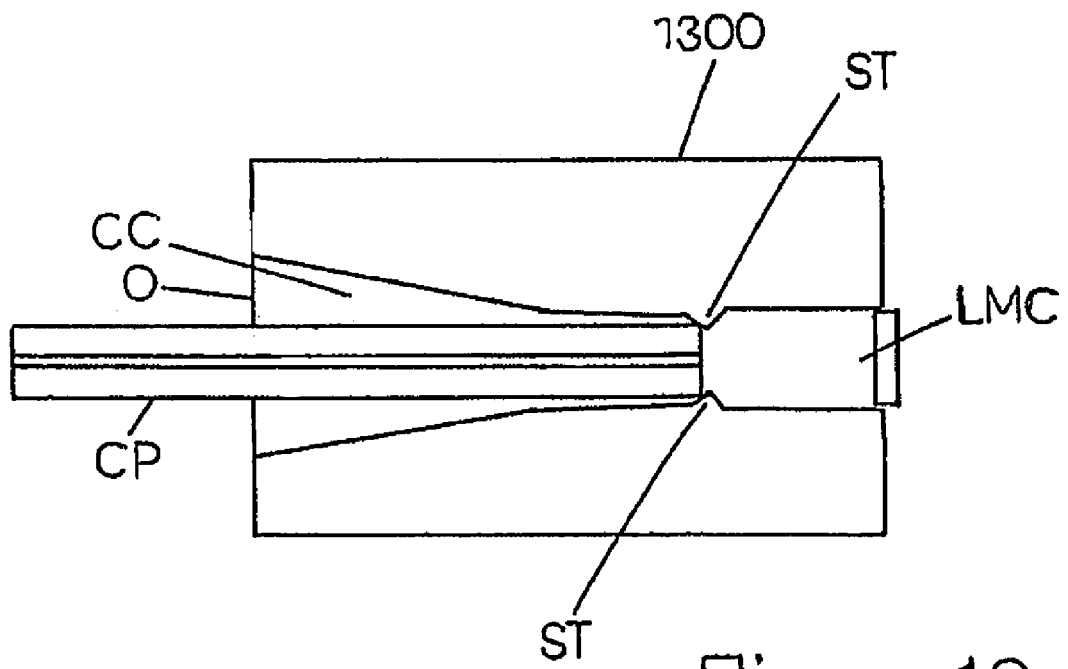

To facilitate the insertion of capillaries, fiber optics, and wires into a microfluidic device, the connection channel can be made much broader at its opening than at the junction with the microchannel. This relaxes the requirements for precision placement of the fiber optic during insertion into the microchannel. FIGS. 13A-13B illustrate top views of a microfluidic chip 1300 for facilitating insertion of capillaries. Referring to FIG. 13A, microfluidic chip 1300 includes a connection channel CC for automated insertion of a capillary CP into connection channel CC. Connection channel CC includes an opening that is much larger than the capillary CP. Connection channel CC can taper to guide capillary CP toward the opposing end of connection channel CC during insertion. Connection channel CC can be designed to self-align capillary CP with microfluidic channel MC. Connection channel CC can include a taper T at the junction of the connection channel CC with microchannel MC. Taper T can serve to automatically align the central axis of the capillary CP with microchannel MC. FIGS. 3A and 3B also demonstrate that alignment perpendicular to the plane of the substrates can be effected by the connection channel. Precision of placement is advantageous for fiber optics because alignment with the microchannel greatly influences the efficiency of optical coupling. Similarly for capillaries, alignment of the capillary with the microchannel greatly influences the dead volume and void volume of the fluidic interconnect.

Referring to FIG. 13B, insertion and alignment of capillary CP or a fiber optic (not shown) can also be facilitated for connection to a larger microscale channel LMC, a channel having a diameter equal to or larger than capillary CP or a fiber optic. Inclusion of a stop ST in connection channel CC permits insertion of capillary CP to the desired distance. Additionally, a stop ST can force glue to flow in front of capillary CP facilitating curing of the glue with minimum void volumes by the techniques described with respect to FIGS. 5 and 8.

Figure 14:
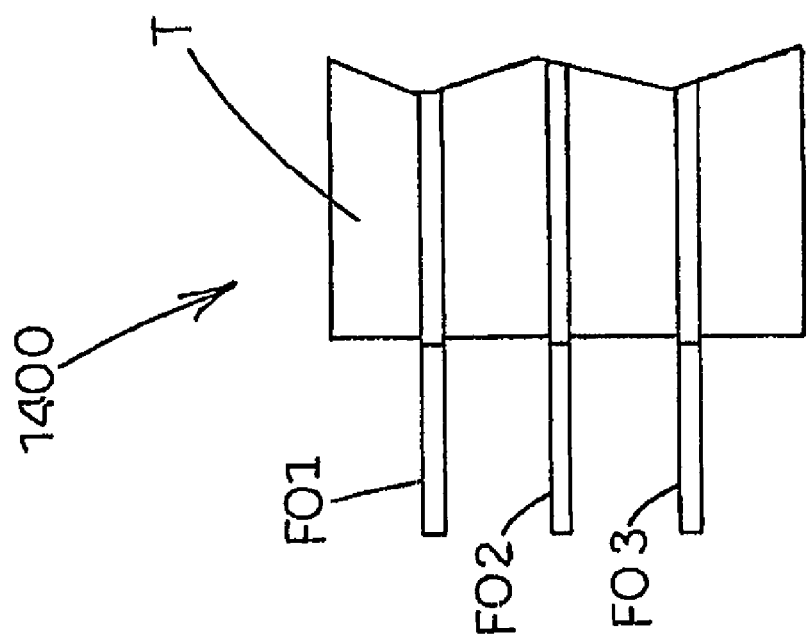
FIG. 14 illustrates a top view of a ribbon assembly for holding multiple fiber optics or capillaries.

FIG. 14 illustrates a top view of a ribbon assembly, generally designated 1400, for holding multiple fiber optics FO1, FO2, and FO3 or capillaries. Alternatively, ribbon assembly 1400 can hold capillaries or wires. Ribbon assembly can comprise a tape assembly for taping fiber optics FO1, FO2, and FO3 together with tape T. Tape T facilitates handling multiple strand-like fiber optics, capillaries, and wires. The spacing of the fiber optics FO1, FO2, and FO3 can be precise and match the spacing of the connection channels in a microfluidic chip for facilitating simultaneous insertion of fiber optics FO1, FO2, and FO3. The spacing can be the same at both ends of ribbon assembly 1400 for simplifying manufacture of ribbon assembly 1400 or spacing can be different at the two ends such that ribbon assembly 1400 resembles a wiring harness. In this configuration, the spacing at one end matches the connection channels on a microfluidic chip and the spacing and/or positioning at the other end matches components off-chip or facilitates connection to components off-chip. Bundling of fiber optics, capillaries, and/or wires can be in two dimensions, as depicted in FIG. 14, or it can be three dimensional whereby the strand-like components are bound by a matrix of, for example, flexible polymer.

Figure 15:
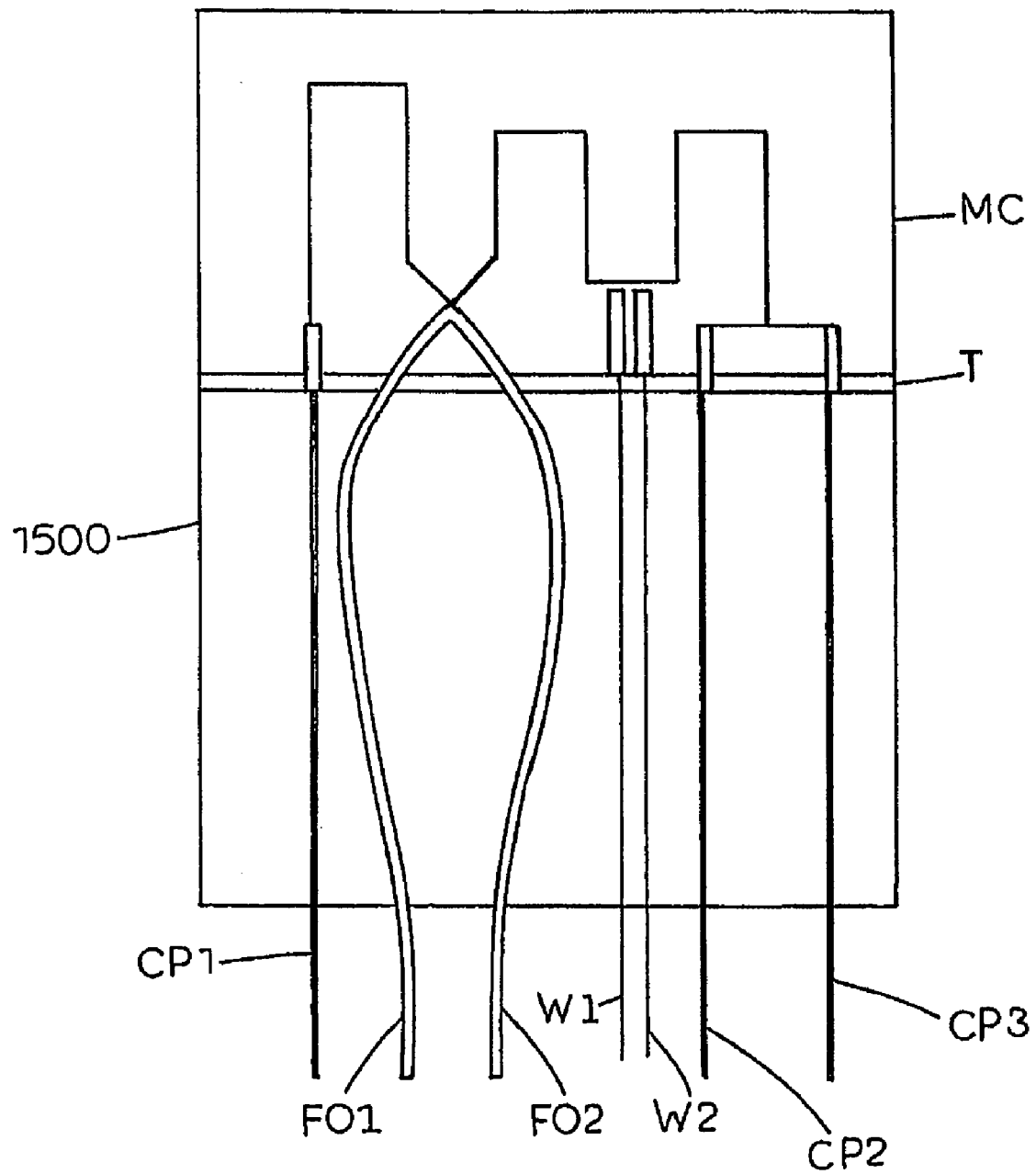
FIG. 15 illustrates a top view of a ribbon assembly for connecting multiple capillaries, wires, and fiber optics into a single microfluidic chip.

FIG. 15 illustrates a top view of a ribbon assembly 1500 for connecting multiple capillaries (CP1, CP2, and CP3), wires (W1 and W2), and fiber optics (FO1 and FO2) into a single microfluidic chip MC. Ribbon assembly 1500 can include tape T attached to microfluidic chip MC, such that the tape T also provides strain relief.

Figure 16A:
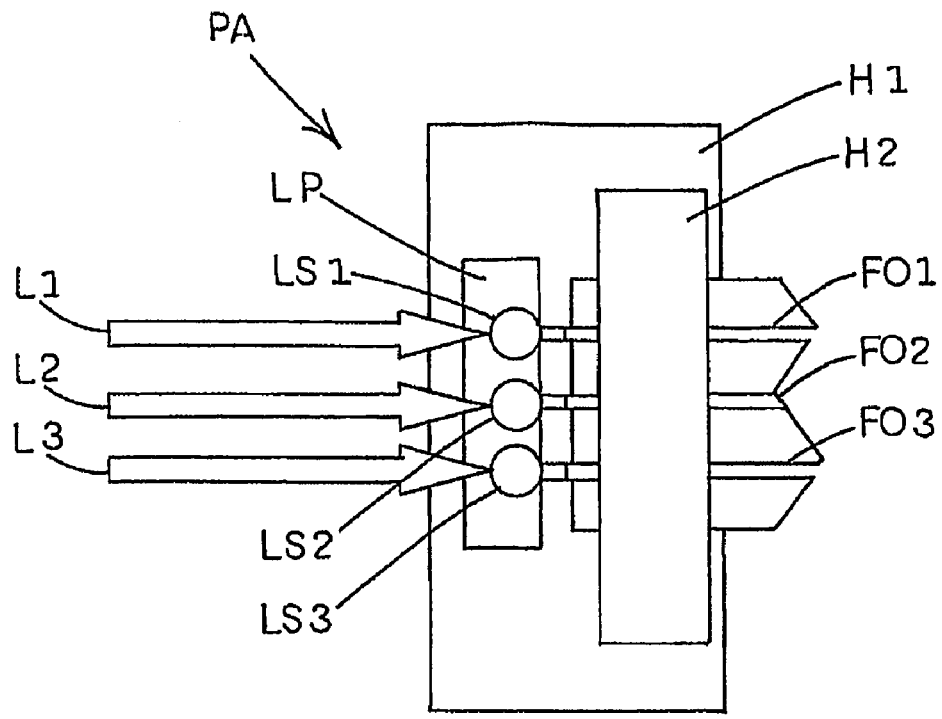
FIG. 16A illustrates a positioner assembly for holding fiber optics or capillaries in front of lenses.

Such bundled components can be used in concert with automated insertion and gluing systems as described at in further detail herein. For example, FIG. 16A illustrates a positioner assembly, generally designated PA, (such as positioners P1, P2, P3, and P4 shown in FIG. 11) for holding fiber optics FO1, FO2, and FO3 in front of lenses LS1, LS2, and LS3, respectively. Lenses LS1, LS2, and LS3 can focus light beams into fiber optics FO1, FO2, and FO3, respectively. Positioner assembly PA can be clamped between holders H1 and H2. A lens positioner LP can hold lenses LS1, LS2, and LS3 at a spacing and height that matches positioner assembly PA. Light beams L1, L2, and L3 can be focused on lenses LS1, LS2, and LS3, respectively, for insertion into fiber optics FO1, FO2, and FO3, respectively.

Figure 16B:
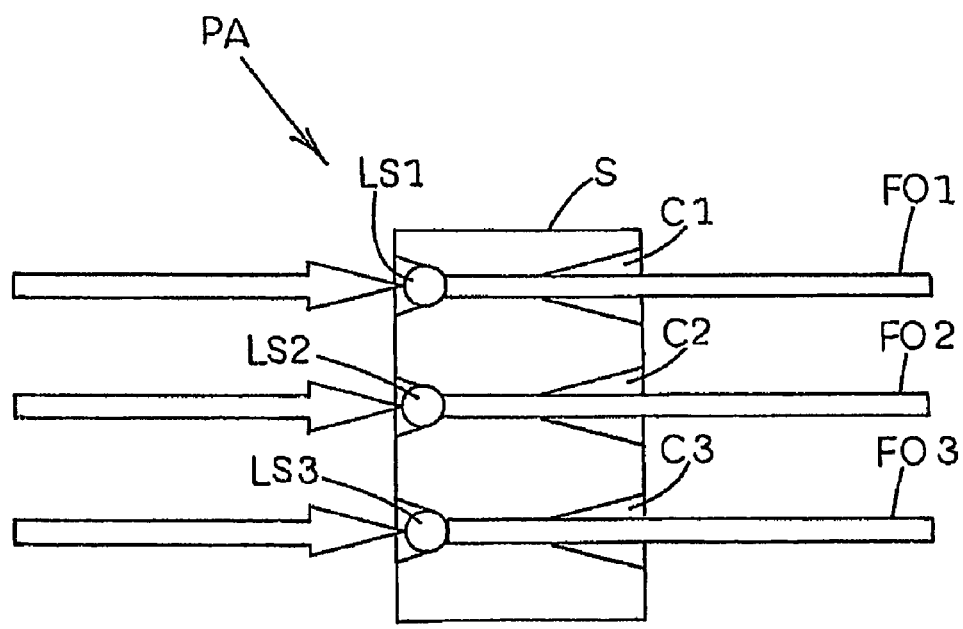
FIG. 16B illustrates another positioner assembly for holding fiber optics or capillaries in front of lenses.

FIG. 16B illustrates a positioner assembly, generally designated PA, (such as positioners P1, P2, P3, and P4 shown in FIG. 11) for holding fiber optics FO1, FO2, and FO3 in front of lenses LS1, LS2, and LS3. Lenses LS1, LS2, and LS3 can focus light beams into fiber optics FO1, FO2, and FO3, respectively. Positioner assembly PA can include a substrate S having channels C1, C2, and C3 formed similar to connection channels. One end of each of channels C1, C2, and C3 is enlarged to accept small lenses LS1, LS2, and LS3, respectively, such as a ball lens. Lenses LS1, LS2, and LS3 can be secured into position by, for example, gluing. Fiber optics FO1, FO2, and FO3 can then be inserted into the other end of channels C1, C2, and C3, respectively, until they abut lenses LS1, LS2, and LS3, respectively. Channels C1, C2, and C3 can align fiber optics FO1, FO2, and FO3, respectively, in all three dimensions with respect to lenses LS1, LS2, and LS3, respectively.

Figure 17A:
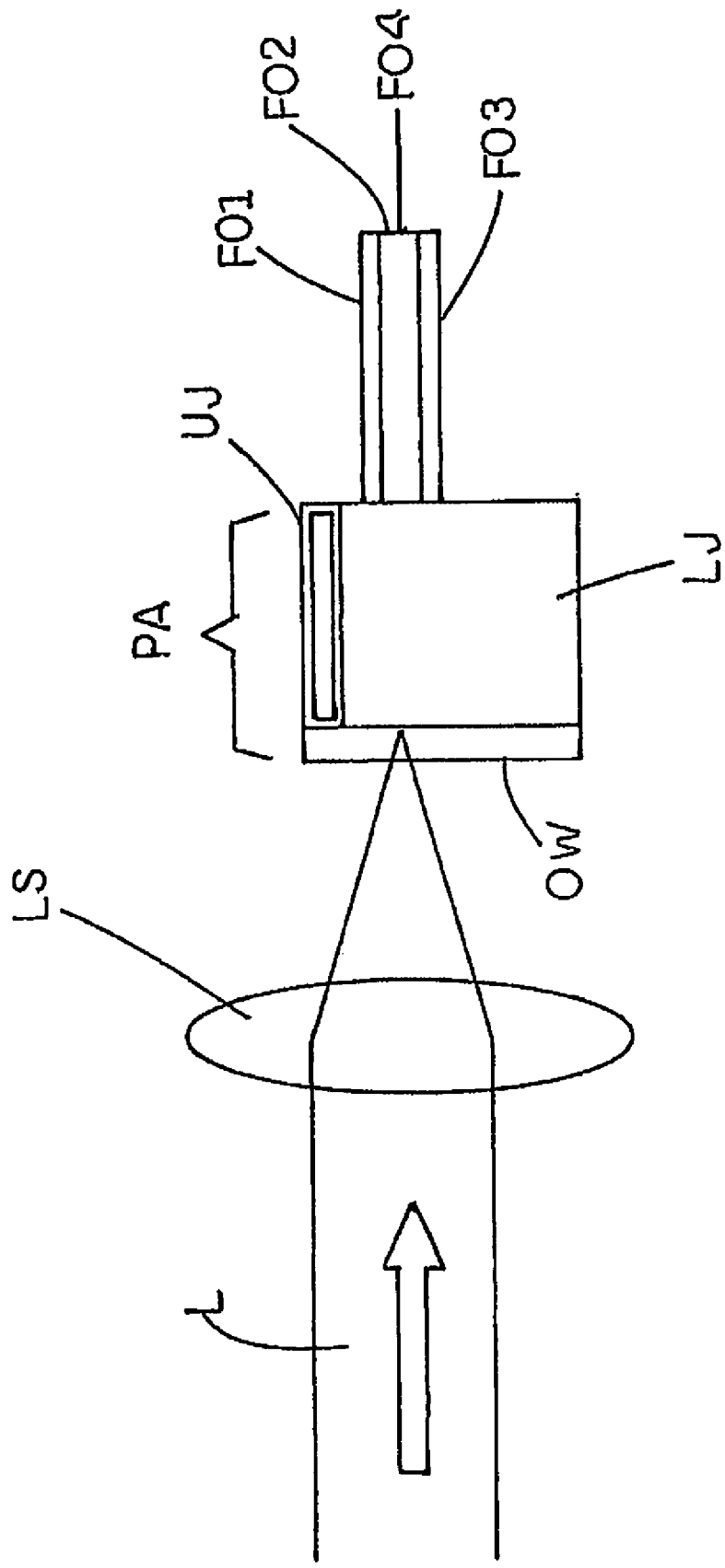
FIGS. 17A and 17B illustrate a positioner assembly for holding fiber optics or capillaries in front of a lens.
Figure 17B:
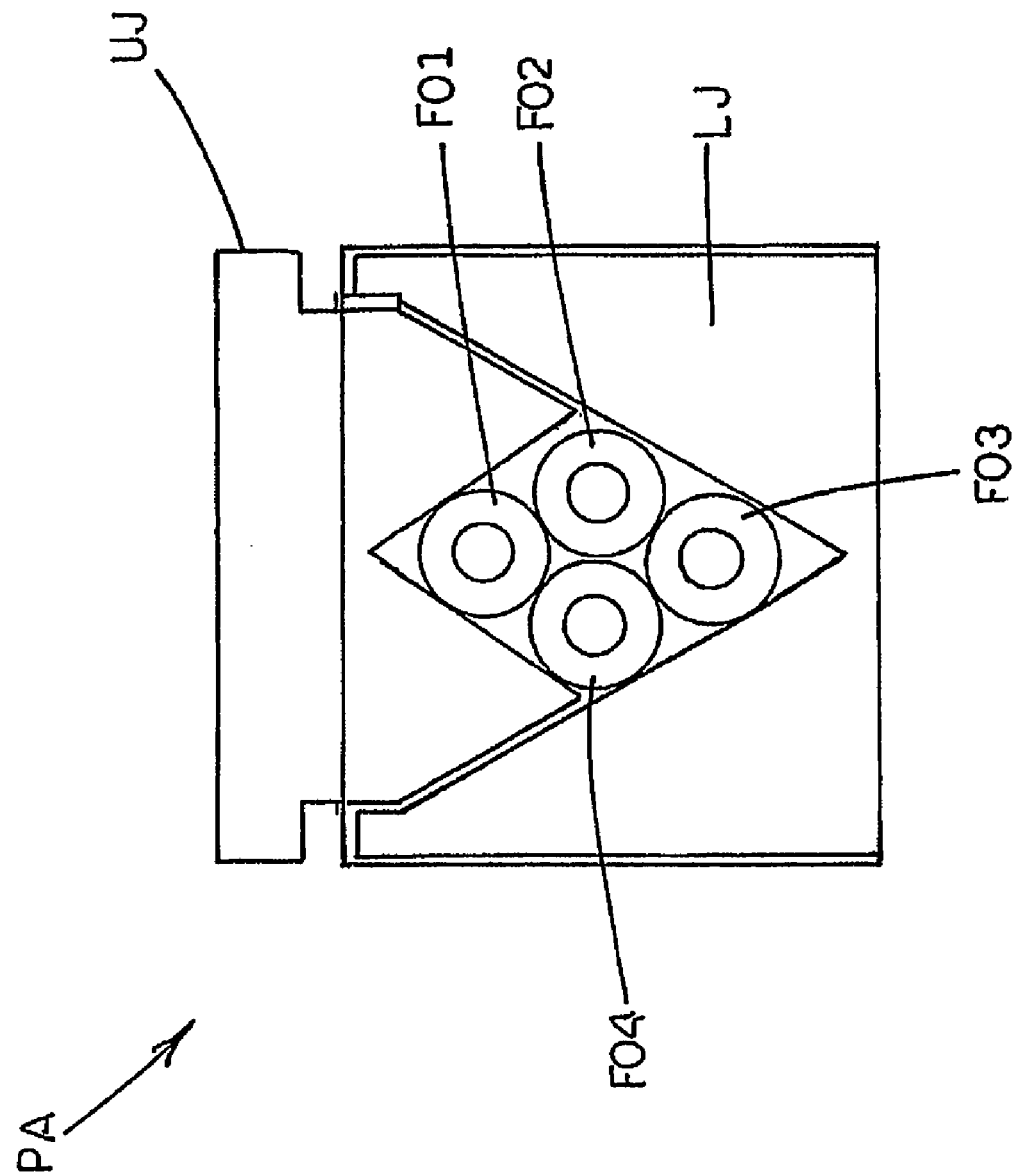

FIGS. 17A and 17B illustrate a side and front view, respectively, of a positioner assembly, generally designated PA, (such as positioner P shown in FIG. 12) for holding multiple fiber optics FO1, FO2, FO3, and FO4 or capillaries. Referring specifically to FIG. 17A, positioner assembly PA can hold fiber optics FO1, FO2, FO3, and FO4 in position in front of a single lens LS. Lens LS can focus a light beam L into the fiber optics FO1, FO2, FO3, and FO4. Positioner assembly PA can comprise a lower jaw LJ and an upper jaw UJ that is movable with respect to lower jaw FFF02 for holding fiber optics FO1, FO2, FO3, and FO4. Fiber optics FO1, FO2, FO3, and FO4 can bundled together such that their axes are parallel and their ends are approximately aligned.

Referring to FIG. 17B, fiber optics FO1, FO2, FO3, and FO4 can then be placed into positioner lower jaw LJ and clamped by lowering upper jaw UJ. The shape of jaws LJ and UJ can be designed such that fiber optics FO1, FO2, FO3, and FO4 are gently compressed into a small bundle for positioning into the focal point of lens LS (shown in FIG. 17A). All fiber optics FO1, FO2, FO3, and FO4 can then be gently pushed up against optical window OW which precisely aligns the ends of all fiber optics FO1, FO2, FO3, and FO4 in position at the focal point of lens LS.

The above descriptions for connections of capillaries, fiber optics, and wires to a microfluidic chip has described connections for capillaries, fiber optics, and wires that are in the plane of the chip, i.e. the central axis of the capillary, fiber optic, or wire is parallel to the plane of the microchannels. Similar techniques can be used to connect capillaries, fiber optics, and wires that are perpendicular to the plane of the microchannels.

Referring to FIGS. 18A-18G, views of different stages in the assembly of a microfluidic chip and connection channel with a capillary CP or with a fiber optic (not shown) or wire (not shown) are illustrated. Referring specifically to FIG. 18A, a base substrate BS can be provided having a microscale channel C1 formed therein. A top substrate TS having a hole H that extends through substrate TS can be provided. Substrates BS and TS can be made from any suitable material, such as polymers, glass, or silicon. Substrates BS and TS can be transparent to the wavelength of light needed to cure glue GL (shown in FIGS. 18F and 18G). FIG. 18B illustrates a top view of substrates TS and BS bonded together to enclose channel C1. FIG. 18C illustrates substrates TS and BS in a cross-sectional, side view.

Referring to FIG. 18D, a capillary CP can be inserted into hole H. Next, referring to FIG. 18E, a light source (not shown) can be turned on for passing light L1 through hole H. Light L1 passing through hole H can be focused by a lens LS onto the end of capillary CP for forming a cone of light L2 that converges at the tip of capillary CP. Referring to FIG. 18F, glue GL can then be placed into the gap between the walls of hole H and capillary CP. Glue GL can then advance down hole H until it is cured by light L2. Light L2 may be directed such that glue GL cures before it enters microscale channel C1.

FIG. 18G illustrates the completed connection of capillary CP. High numerical aperture of light focused by lens LS can be advantageous in that the light intensity drops rapidly out of the plane of focus. This reduces the amount of light that reflects up the gap between the walls of hole H and capillary CP for allowing glue GL to advance to the front edge of capillary CP. Additionally, shuttering of light L1 can be used to ensure glue GL is cured at the correct position relative to capillary CP and hole H. Automation of fabrication of connections shown in FIGS. 18A-18G can be automated in a fashion similar to processes described above. Formation of connections perpendicular to the plane of a microfluidic chip also can be made to fiber optics and capillaries that can conduct light to the joint, in a fashion similar to the processes described above.

FIGS. 19A-19G illustrate views of alternative stages in the assembly of a microfluidic chip and connection channel with a capillary CP or with a fiber optic (not shown). Referring specifically to FIG. 19A, a base substrate BS can be provided having a microscale channel C1 formed therein. A top substrate TS having a hole H that extends through substrate TS can be provided. Substrates BS and TS can be made from any suitable material, such as polymers, glass, or silicon. Substrates BS and TS can be transparent to the wavelength of light needed to cure glue GL (shown in FIGS. 19F and 19G). FIG. 19B illustrates a top view of substrates TS and BS bonded together to enclose channel C1. FIG. 19C illustrates substrates TS and BS in a cross-sectional, side view.

Referring to FIG. 19D, a light-guiding capillary CP can be inserted into hole H. Next, referring to FIG. 19E, a light source (not shown) can be turned on for shining light L through capillary CP. Light L passing through capillary CP can form a cone of light L that diverges at the end of capillary CP. Referring to FIG. 19F, glue GL can then be placed into the gap between the walls of hole H and capillary CP. Glue GL can then advance down hole H until it is cured by light L2. FIG. 19G illustrates the completed connection. Note that illumination of the entire glue area with a second light can be used after formation of the completed connection to ensure complete curing of glue GL.

The addition of a light opaque coating, such as polyimide or black paint or a black-doped glass for the cladding of the fiber optic can reduce light in the gap between the walls of hole H and capillary CP. Using a top substrate TS that strongly absorbs light L can also reduce light in the gap between the walls of hole H and capillary CP. Roughening of the wall of hole H or of the outside of capillary CP or fiber optic FO can be used to reflect light laterally to reduce light propagation in the gap between the walls of hole H and capillary CP. All of these techniques can allow glue GL to advance to the front edge of capillary CP before it cures in the gap. Additionally, reflection of light L off the bottom of microscale channel C1 can be used to cure glue GL in hole H above microscale channel C1 before glue GL enters microscale channel C1.

Figure 20A:
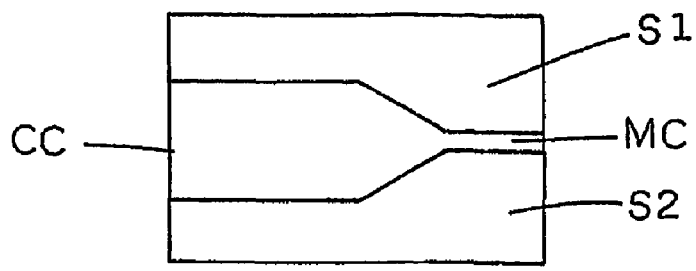
FIG. 20A-20E illustrate views of stages in the assembly of a microfluidic chip and connection channel with a fiber optic, a wire, or a capillary.
Figure 20B:
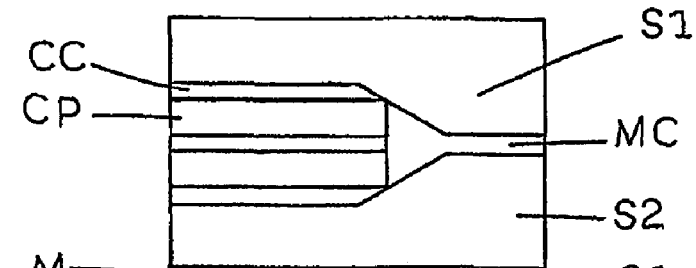

FIGS. 20A-20E illustrate views of stages in the assembly of a microfluidic chip and connection channel with a fiber optic or alternatively a wire (not shown) or capillary (not shown). This assembly process utilizes an optically opaque mask to define the illuminated region of the connection channel. Referring specifically to FIG. 20A, which provides a top view, illustrates a connection channel CC and microscale channel MC that have been formed into a substrate S1. A top substrate (not shown) is attached to complete connection channel CC and microscale channel MC as described above. FIG. 20B illustrates a capillary CP inserted into connection channel CC.

Figure 20C:
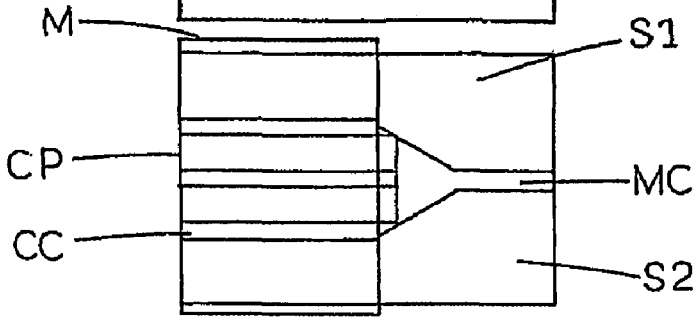

Referring to FIG. 20C, an optically opaque mask M can be positioned over connection channel CC. Mask M can be made from any material that is opaque to the wavelengths of light used to cure glue GL (shown in FIGS. 20D and 20E). Additionally, mask M can be transparent to other wavelengths, permitting optical inspection of the connection channel CC. Mask M can be electroplated onto the top substrate, glued on, or placed in contact with or slightly elevated above substrates S1 and S2.

Figure 20D:
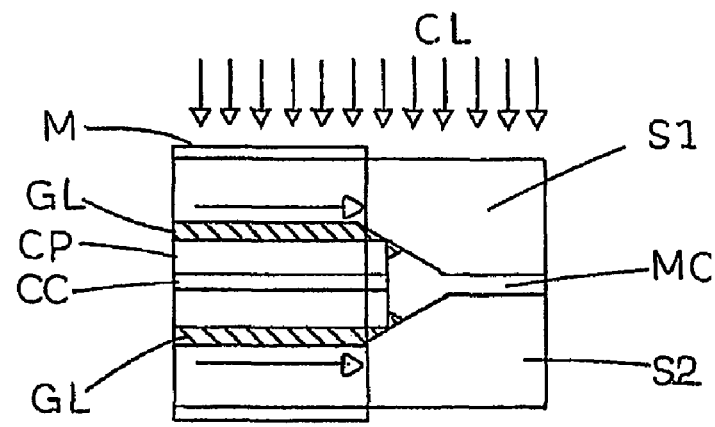
Figure 20E:
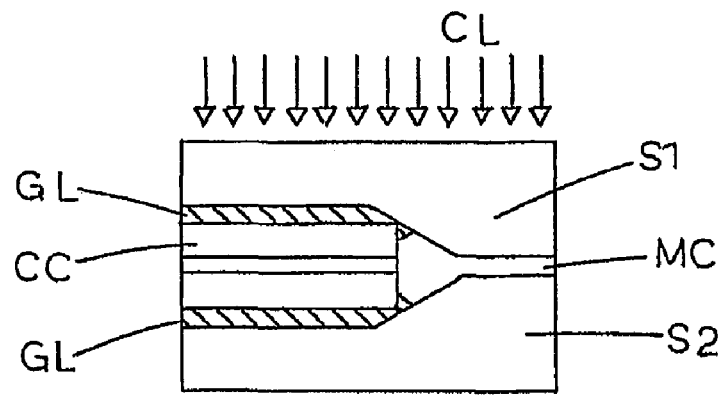

Referring to FIG. 20D, glue GL at the end of capillary CP can be cured with a spot of light from light CL. Light CL can be collimated to provide a sharp delineation between illuminated and masked regions. Connection channel CC includes a shaded area covered by opaque mask M such that only the end of capillary CP is illuminated by light CL. When glue GL enters connection channel CC, glue GL is not exposed to the light until it reaches the end of capillary CP where it is cured on entering the collimated light CL. Referring to FIG. 20E, after the advance of the glue GL is halted by curing at the end of capillary CP, mask M can be removed and the rest of glue GL is cured in connection channel CC. Alternatively, a second light (not shown) can illuminate the opposite side of the chip and, therefore, not blocked by mask M, to cure the rest of glue GL in connection channel CC. Alternatively, the rest of glue GL can be cured by a secondary method appropriate for the glue, such as heating.

Figure 21A:
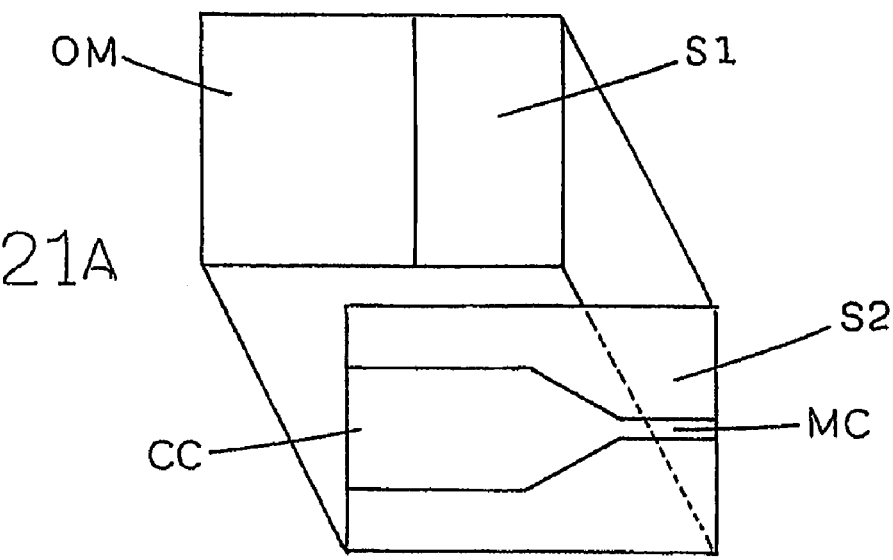
FIG. 21A-21G illustrate alternative stages in the assembly of a microfluidic chip using an opaque mask to form a connection.
Figure 21B:
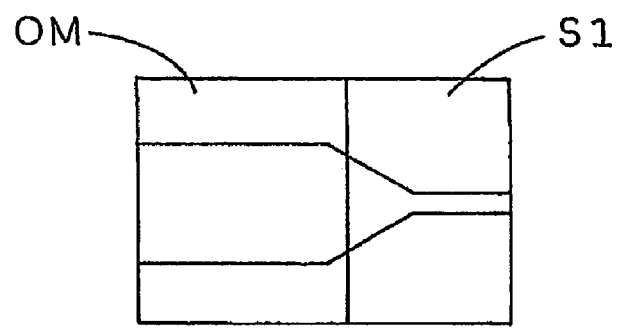
Figure 21C:
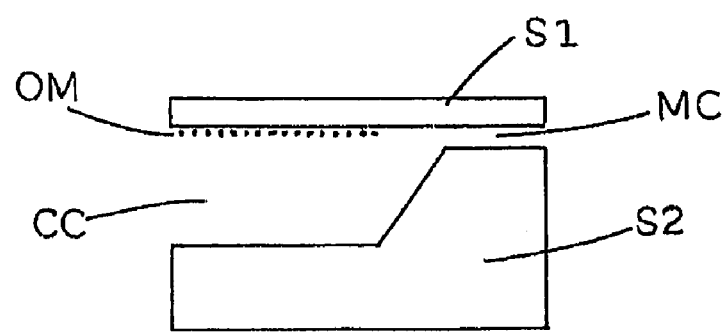

FIGS. 21A-21G illustrate alternative stages in the assembly of a microfluidic chip of using an opaque mask to form a connection. Referring specifically to FIG. 21A, an exploded view is provided of a top substrate S1 having an opaque mask OM formed thereon and a bottom substrate S2 having a connection channel CC and microscale channel MC formed therein. Opaque mask OM can be attached to substrate S1 by one of the following methods: adhering a foil to substrate S1; sputtering or vapor depositing a metal layer or other opaque layer onto substrate S1; or painting an opaque layer onto S1. FIGS. 21B and 21C illustrate a top view and a cross-sectional view, respectively, of the assembly of substrates S1 and S2.

Figure 21D:
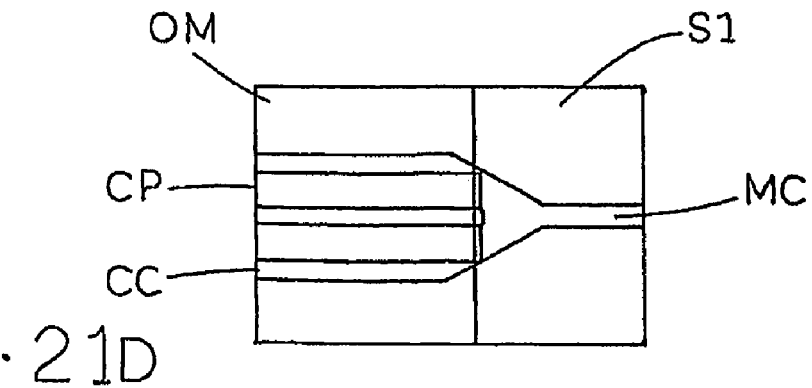
Figure 21E:
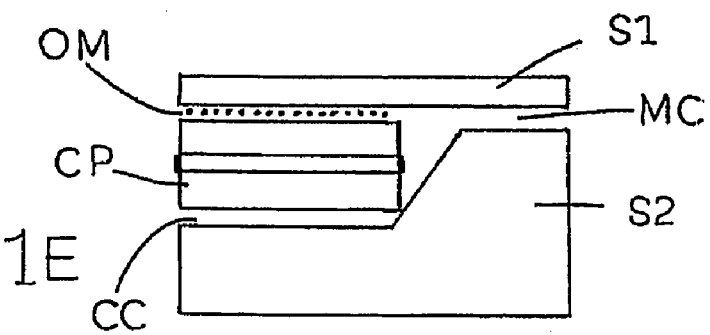
Figure 21F:
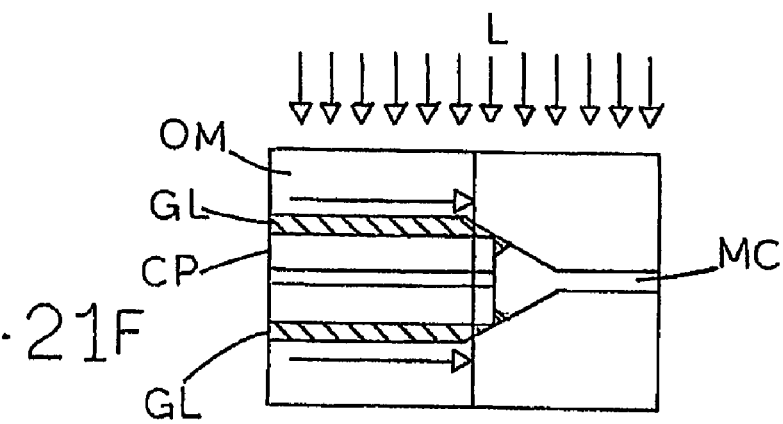
Figure 21G:
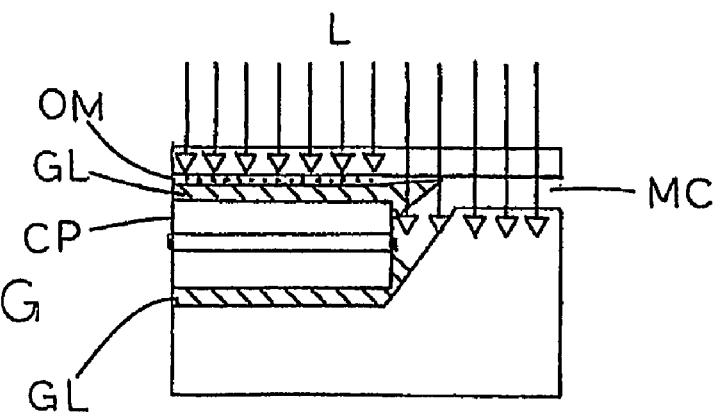

FIGS. 21D and 21E illustrate a top view and cross-sectional view, respectively, of substrates S1 and S2 having a capillary CP inserted in connection channel CC. FIGS. 21F and 21G illustrate a top and cross-sectional view, respectively, of a light L shining through top substrate S1 for curing light-curable glue GL applied to connection channel CC. The portion of glue GL near the end of capillary CP can be cured by the portion of light L that is not blocked by opaque mask OM. Next, the remainder of glue GL can be cured by shining light (not shown) through bottom substrate S2. Alternatively, the rest of glue GL can be cured by a secondary method appropriate for the glue, such as heating.

Figure 22A:
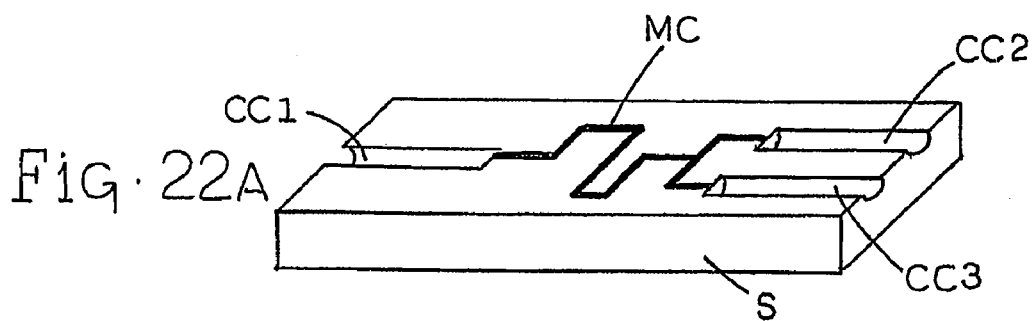
FIG. 22A-22D illustrate views of different stages in the assembly of a microfluidic chip in which selective melting is used to fill a gap between the microcapillary, fiber optic, or wire and the wall of a connection channel.
Figure 22B:
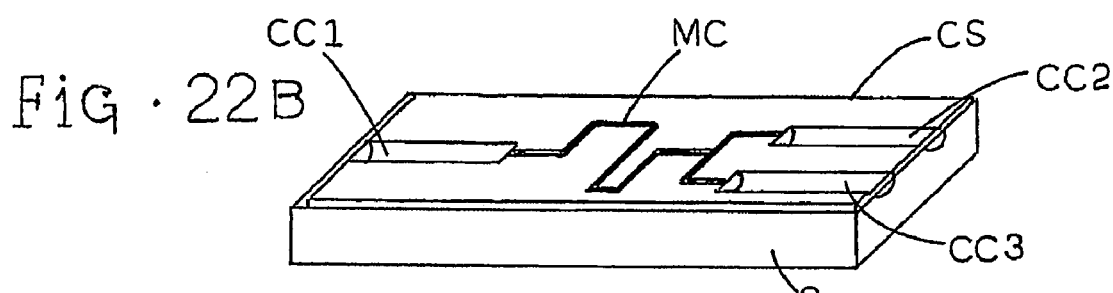

According to another embodiment, the gap between a wall of a connection channel and a capillary, fiber optic, or wire can be filled by selectively melting materials over the capillary such that the melted material fills the gap and attach the capillary to the connection channel. This has the advantage that it does not introduce a third material (e.g., a glue) which can complicate material compatibilities with fluids for which the microfluidic device is to be used. Referring to FIGS. 22A-22D, views of different stages in the assembly of a microfluidic chip in which selective melting is used to fill gap between the microcapillary, fiber optic, or wire and the wall of the connection channel are illustrated. Referring specifically to FIG. 22A, a perspective view of a substrate S is provided. Connection channels CC1, CC2, and CC3 and microfluidic channel MC can be etched into a surface of substrate S1. Referring to FIG. 22B, channels CC1, CC2, and CC3 can enclosed by bonding cover slip CS to substrate S.

Figure 22C:
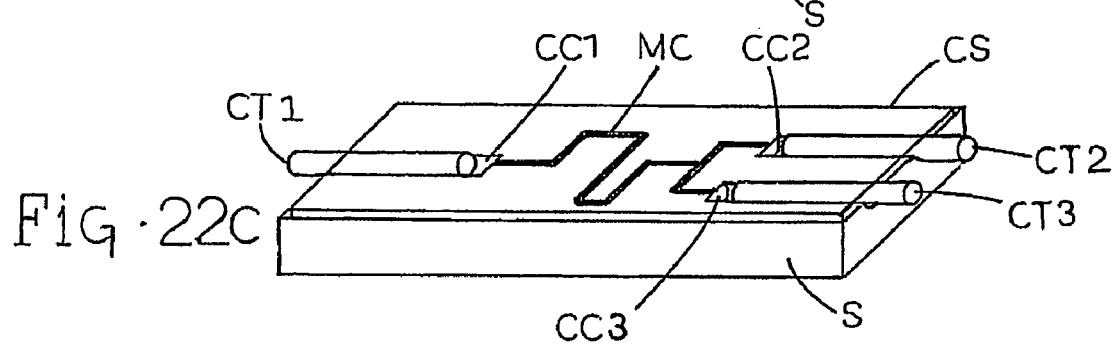
Figure 22D:
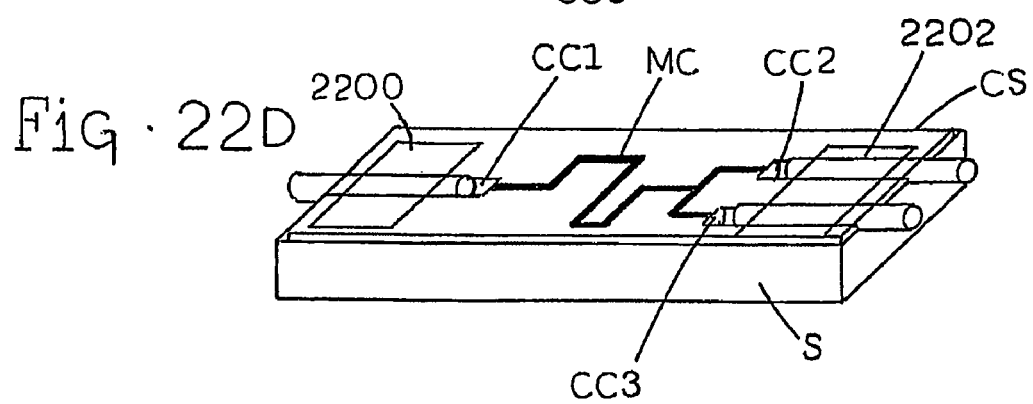

Referring to FIG. 22C, capillary tubes CT1, CT2, and CT3, can be positioned in connection channels CC1, CC2, and CC3, respectively. Referring to FIG. 22D, portions 2200 and 2202 of cover slip CS, which cover a portion of capillary tubes CT1, CT2, and CT3, can be melted selectively, filling in the gap between the capillary tubes CT1, CT2, and CT3 and the wall of connection channels CC1, CC2, and CC3, respectively. Glue can be placed at the openings of channels CC1, CC2, and CC3 at the edge of substrate S to mechanically strengthen the attachment of capillary tubes CT1, CT2, and CT3 to substrate S and cover slip CS; however, the melted material around capillary tubes CT1, CC2, and CC3 forms the fluid-tight seals.

Figure 23A:
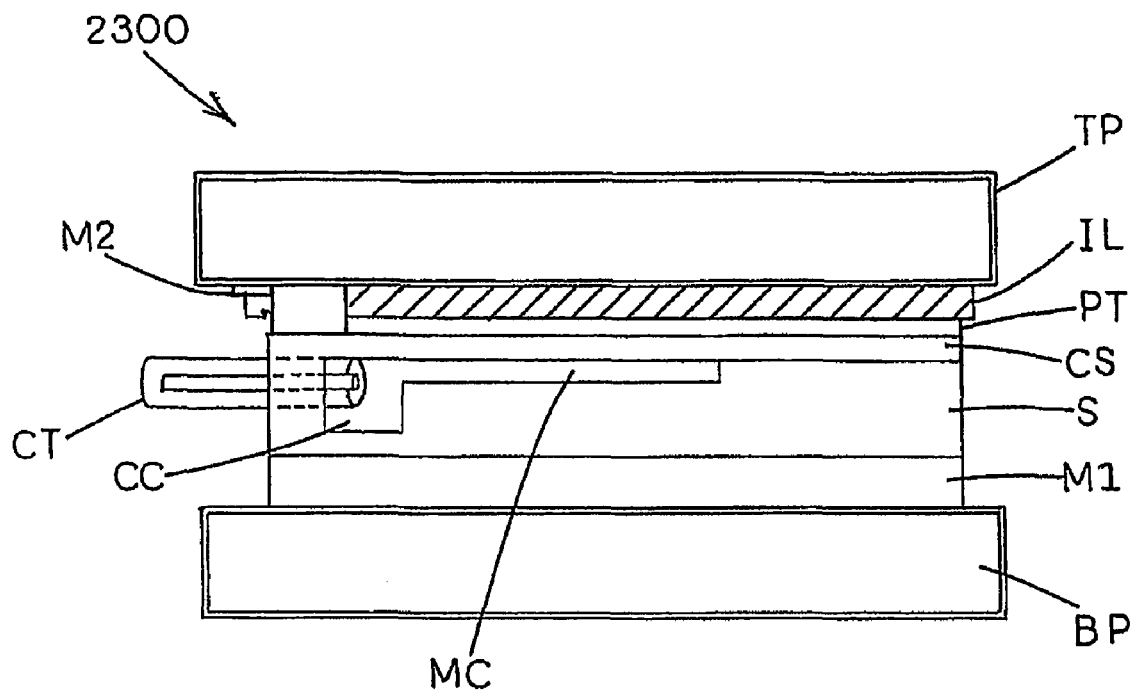
FIGS. 23A and 23B illustrates a cross-sectional side view and cross-sectional end view, respectively, of a microfluidic chip being bonded together with a top platen and bottom platen of a platen press.
Figure 23B:
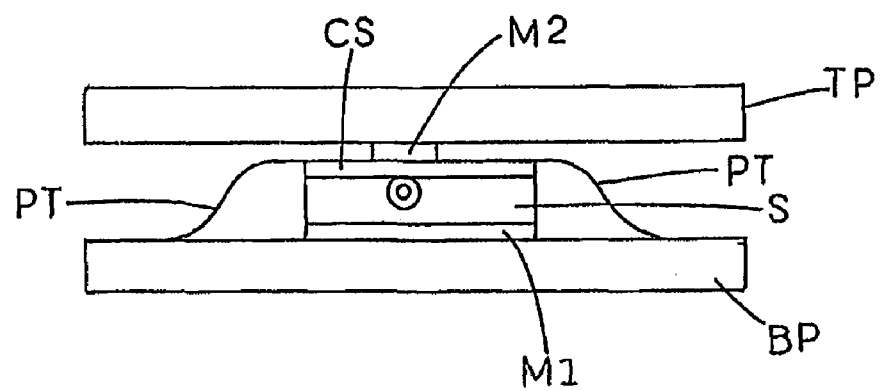

FIGS. 23A and 23B illustrate a cross-sectional side view and cross-sectional end view, respectively, of a microfluidic chip, generally designated 2300, being bonded together with a top platen TP and bottom platen BP of a platen press (not shown). This is an embodiment for melting the material around a capillary tube CT as described with respect to FIG. 22. Microfluidic chip 2300 can include a substrate S having a connection channel CC and microfluidic channels MC etched therein. Microfluidic chip 2300 can also include a cover slip CS bonded on top of substrate S for enclosing connection channel CC and microfluidic channels MC. An optically smooth material M1 can be positioned between substrate S and bottom platen BP. A thermally conductive material M2 can be positioned at a region onto or near cover slip CS for allowing heat to transfer from the top platen TP to a localized region of the cover slip CS. Heat can be transferred to this region of cover slip CS for melting that portion of cover slip CS to attach capillary tube to cover slip CS and substrate S. A thermally-insulating layer IL can be positioned at a region between top platen TP and cover slip CS for preventing top platen TP from conducting heat to the remaining portion of cover slip CS. According to one embodiment, insulating layer IL can comprise air. If insulating layer IL comprises air, an additional layer of tape PT can be used to hold the substrate down and prevent it from warping.

The gap surrounding capillary tube CT can be filled by heating top platen TP and selectively melting cover slip CS only under thermally-conductive material M2. The melted material of cover slip CS can fill in the gap between the capillary tube CT and the wall of the connection channel CC. The selective application of heat to cover slip CS to an area defined by the size of thermally-conductive material M2 can melt only the portion of cover slip CS above capillary tube CT. This preserves microscale channel MC and the portion of connection channel CC not adjacent to capillary tube CT.

Figure 24A:
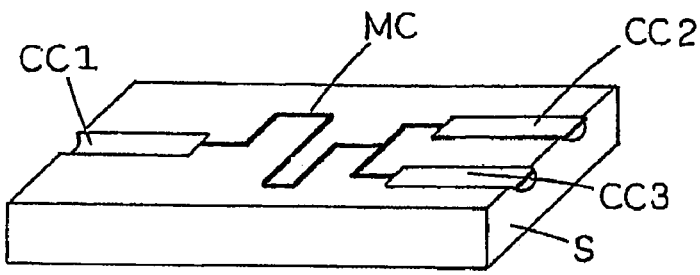
FIGS. 24A-24D illustrate different stages in the assembly of a microfluidic chip comprised of two different materials having different melting temperatures, in which selective melting is used to fill the gap between the capillary, fiber optic, or wire and the wall of the connection channel.
Figure 24B:
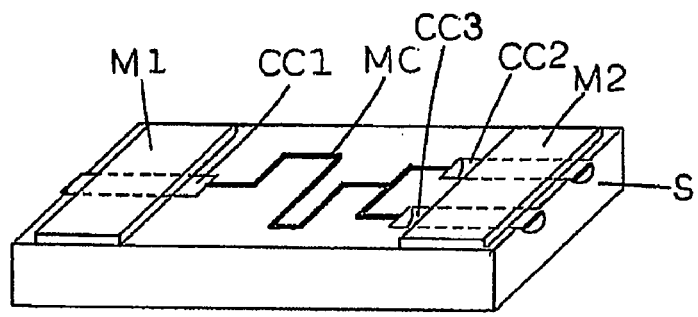

According to another embodiment, a microfluidic chip can be provided having two different materials with very similar coefficients of thermal expansion and different melting temperatures. FIGS. 24A-24D illustrate different stages in the assembly of a microfluidic chip comprised of two different materials having different melting temperatures, in which selective melting is used to fill the gap between the capillary (or alternatively a fiber optic or wire) and the wall of the connection channel. Referring specifically to FIG. 24A, a perspective view of a substrate S is provided. Connection channels CC1, CC2, and CC3 and microfluidic channel MC can be etched into a surface of substrate S. Next, referring to FIG. 24B, pieces of a material M1 and M2 having a lower melting temperature than substrate S but the same coefficient of thermal expansion can be bonded over a substantial portion of connection channels CC1, CC2, and CC3.

Figure 24C:
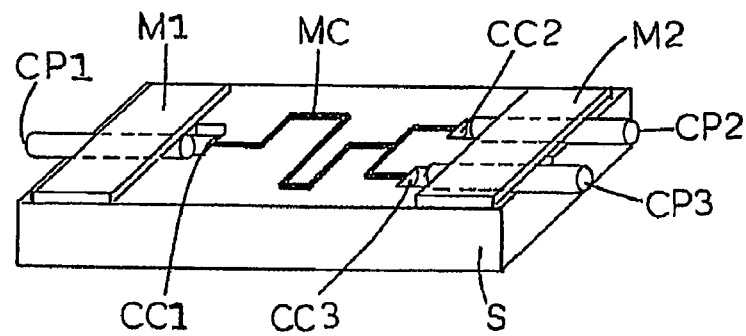
Figure 24D:
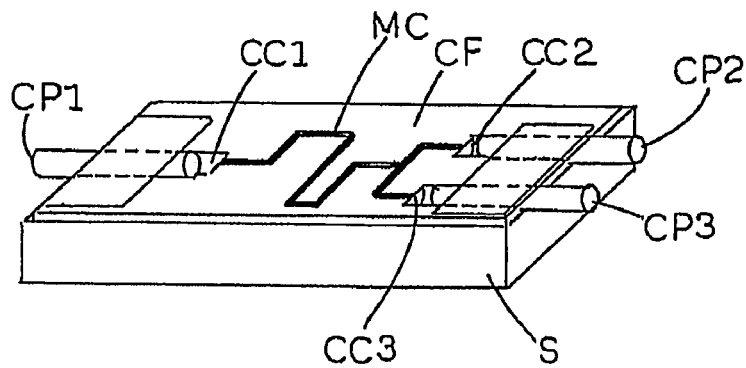

Referring to FIG. 24C, capillaries CP1, CP2, and CP2 can be positioned in connection channels CC1, CC2, and CC3, respectively. Materials M1 and M2 can then be melted over capillaries CP1, CP2, and CP3. When melted, material M1 and M2 can fill the gaps surrounding capillaries CP1, CP2, and CP3 for achieving liquid-tight seals between capillaries CP1, CP2, and CP3 and the substrate S. Because connection channels CC1, CC2, and CC3 and microfluidic channel MC are etched into a different material (substrate S) having a high melting point, then connection channels CC1, CC2, and CC3 and microfluidic channel MC will not melt during the melting step if the temperature is kept sufficiently low. Referring to FIG. 24D, following the selective melt procedure, a cover film CF can be bonded to the underlying substrate S with melted materials M1 and M2 to enclose channels CC1, CC2, and CC3.

Substrate S can comprise Zeonor 1420R (available from Zeon Chemicals L.P. of Louisville, Ky.). Materials M1 and M2 can comprise Topaz 8007 (available from Ticona of Summit, New Jersey Kentucky), respectively. These cyclic-olefin-copolymers have very similar coefficients of thermal expansion, but very different melting temperatures.

Figure 25:
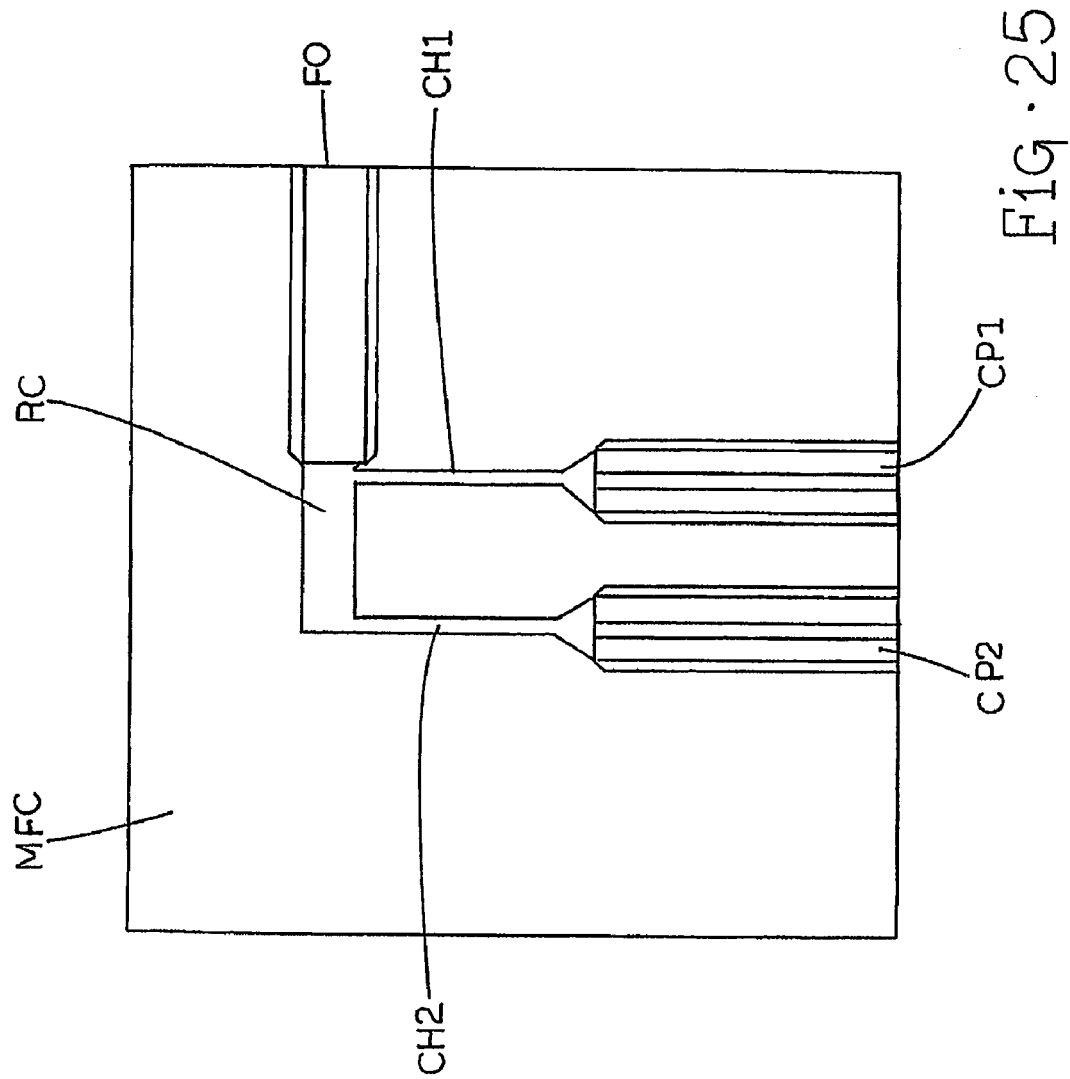
FIG. 25 illustrates a top view of a microfluidic chip for introducing light into a fluid.

FIG. 25 illustrates a top view of a microfluidic chip MFC for introducing light into a fluid. According to one embodiment, light can be introduced into fluid for initiating a photo-activatable reaction. Microfluidic chip MFC can include a capillary CP1 for delivering fluid into a reaction chamber RC. Fluid entering microfluidic chip MC via capillary CP1 can flow through a microchannel CH1 having fluid connection to capillary CP1. Microchannel CH1 can deliver fluid from capillary CP1 to reaction chamber RC. Microfluidic chip MFC can also include a microchannel CH2 having fluid connection to a capillary CP2. Fluid can exit from reaction chamber RC through microchannel CH2 and out of chip MFC via capillary CP2.

Microfluidic chip MFC can also include a fiber optic FO having an end facing reaction chamber RC. An opposing end of fiber optic FO can be connected to a light source (not shown). Fluid can be pumped through reaction chamber RC, as described above, while light is introduced via fiber optic FO into reaction channel RC. Additional fiber optics can be added to permit sequential treatment, or to control the distribution of light intensity in reaction chamber RC, or to permit attachment of multiple light sources for control of the spectral distribution of light in reaction chamber RC. Additional microchannels and capillaries can be connected to permit combination of multiple fluids before, into, or after reaction chamber RC.

Figure 26:
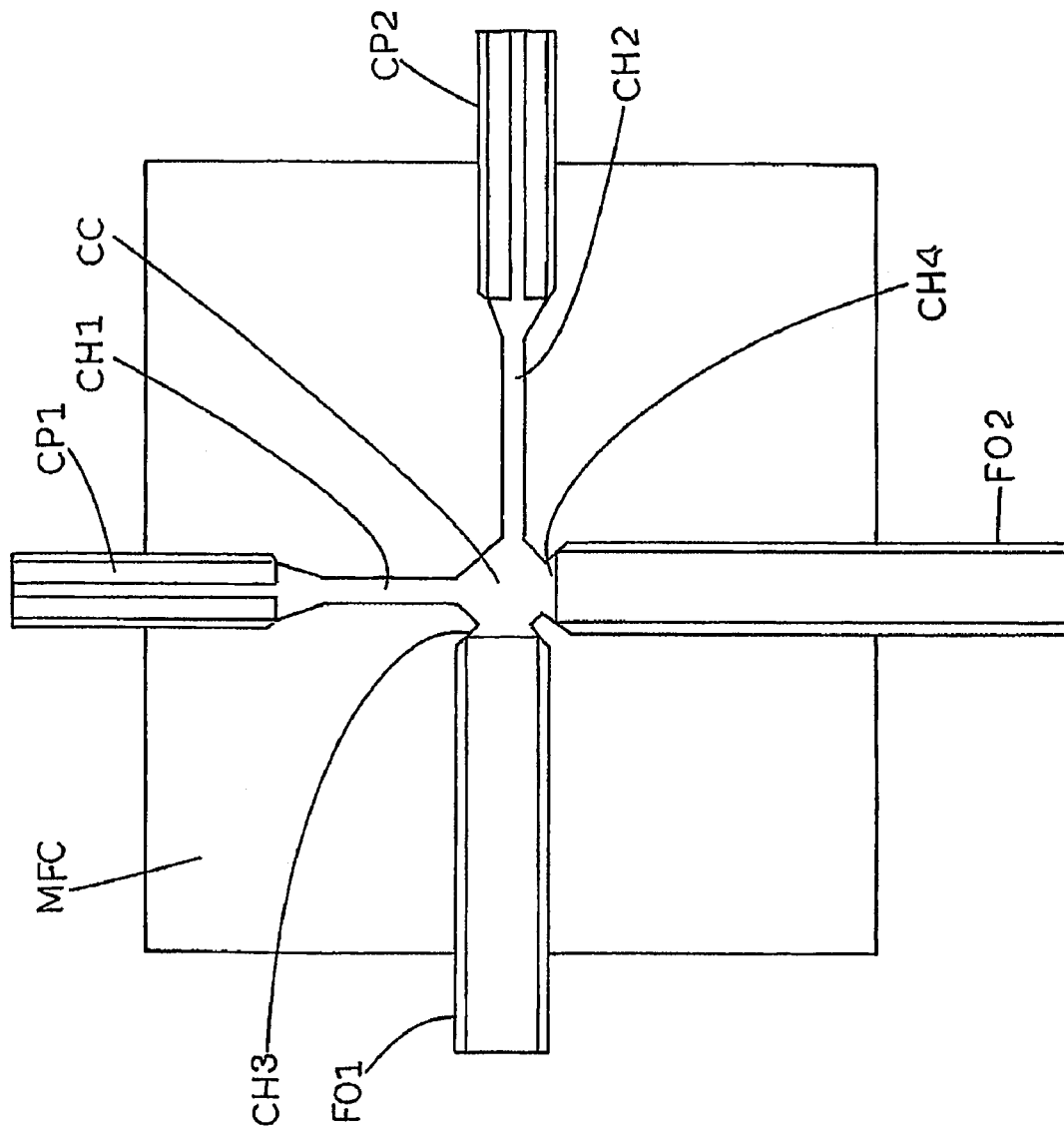
FIG. 26 illustrates a top view of a microfluidic chip for introducing two beams of light into a fluid or to introduce one beam of light and to monitor light emitted from the fluid due to, for example, scattering or fluorescence.

FIG. 26 illustrates a top view of a microfluidic chip MFC for introducing two beams of light into a fluid or to introduce one beam of light and to monitor light emitted from the fluid due to, for example, scattering or fluorescence. Microfluidic chip MFC can include a microchannel CH1 having a fluid connection to a capillary CP1 for delivering fluid to a cuvette channel CC. Microfluidic chip MFC can also include another microchannel CH2 for receiving fluid from cuvette channel CC for exit through capillary CP2 and out of chip MFC.

Referring still to FIG. 26, microfluidic chip MFC can also include other microchannels CH3 and CH4 for holding fiber optics FO1 and FO2, respectively. Fiber optic FO1 can have an end facing to cuvette channel CC and an opposing end connected to a remote light source (not shown). Fiber optic FO2 can have an end facing cuvette channel CC and an opposing end attaches to a photodetector (not shown). When fluid is pumped through cuvette channel CC, light can be introduced via fiber optic FO1. Fluorescent or scattered light arising from light introduced by fiber optic FO1 and emanating from the fluid in cuvette channel CC can be collected by fiber optic FO2 and detected at the off-chip photodetector.

Figure 27:
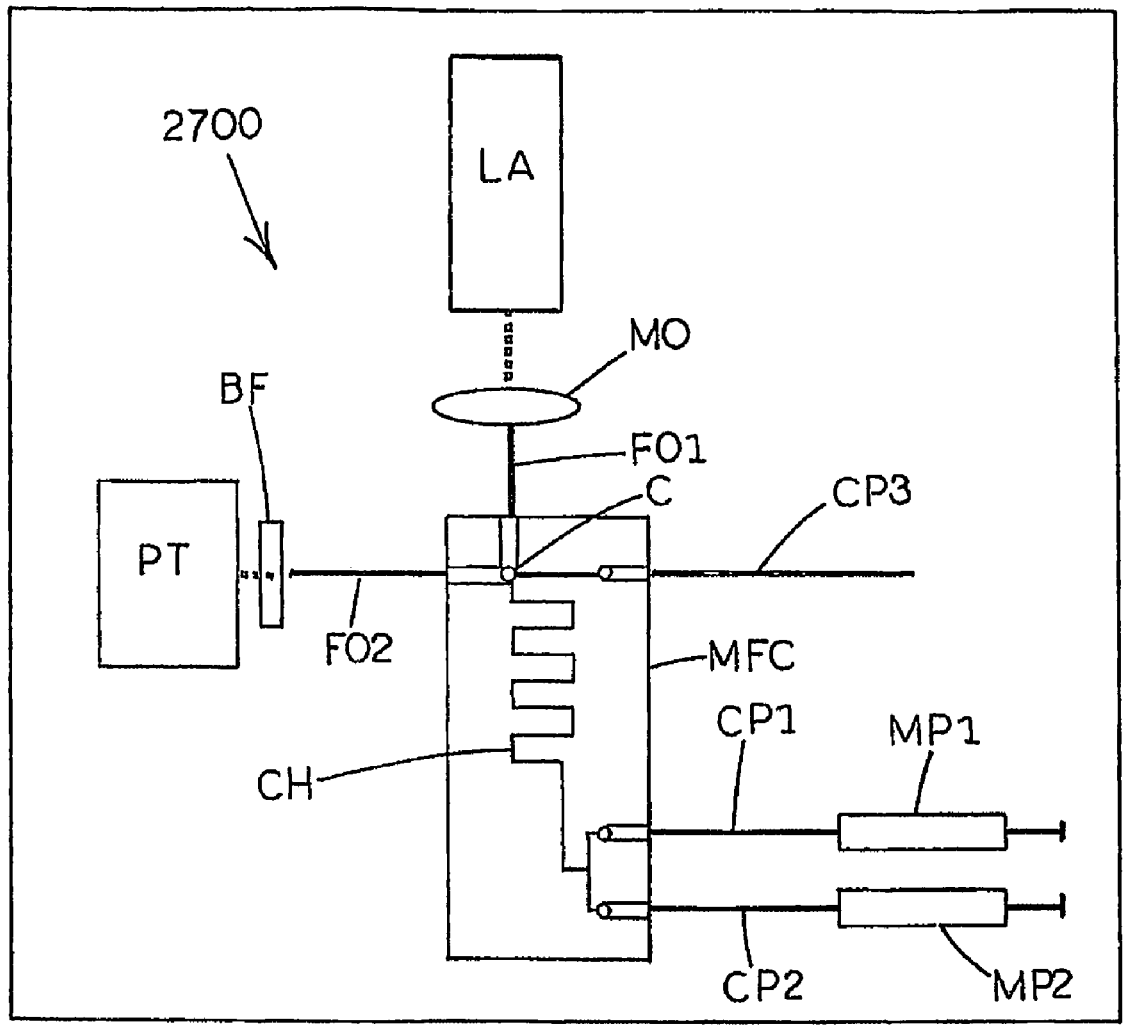
FIG. 27 illustrates a schematic diagram of a microfluidic system including a microfluidic chip configured similar to the microfluidic chips described above, such as microfluidic chip shown in FIG. 26.

FIG. 27 illustrates a schematic diagram of a microfluidic system, generally designated 2700, including a microfluidic chip MFC configured similar to the microfluidic chips described above, such as microfluidic chip MFC shown in FIG. 26. Microfluidic chip MFC can include a microchannel CH. Microchannel CH can receive different fluids from microsyringe pumps MP1 and MP2 through two input capillaries CP1 and CP2, respectively, connected to chip MFC. The fluids can combine in microchannel CH and travel to a microcuvette C for analysis. Capillaries CP1 and CP2 can be attached to chip MFC with a technique described above, such as the technique described with regard to FIGS. 5A-5E. Microfluidic chip MFC can be attached to fiber optics FO1 and FO2 such that microcuvette C is aligned with light transmitted to or from fiber optics FO1 and FO2.

Figure 28:
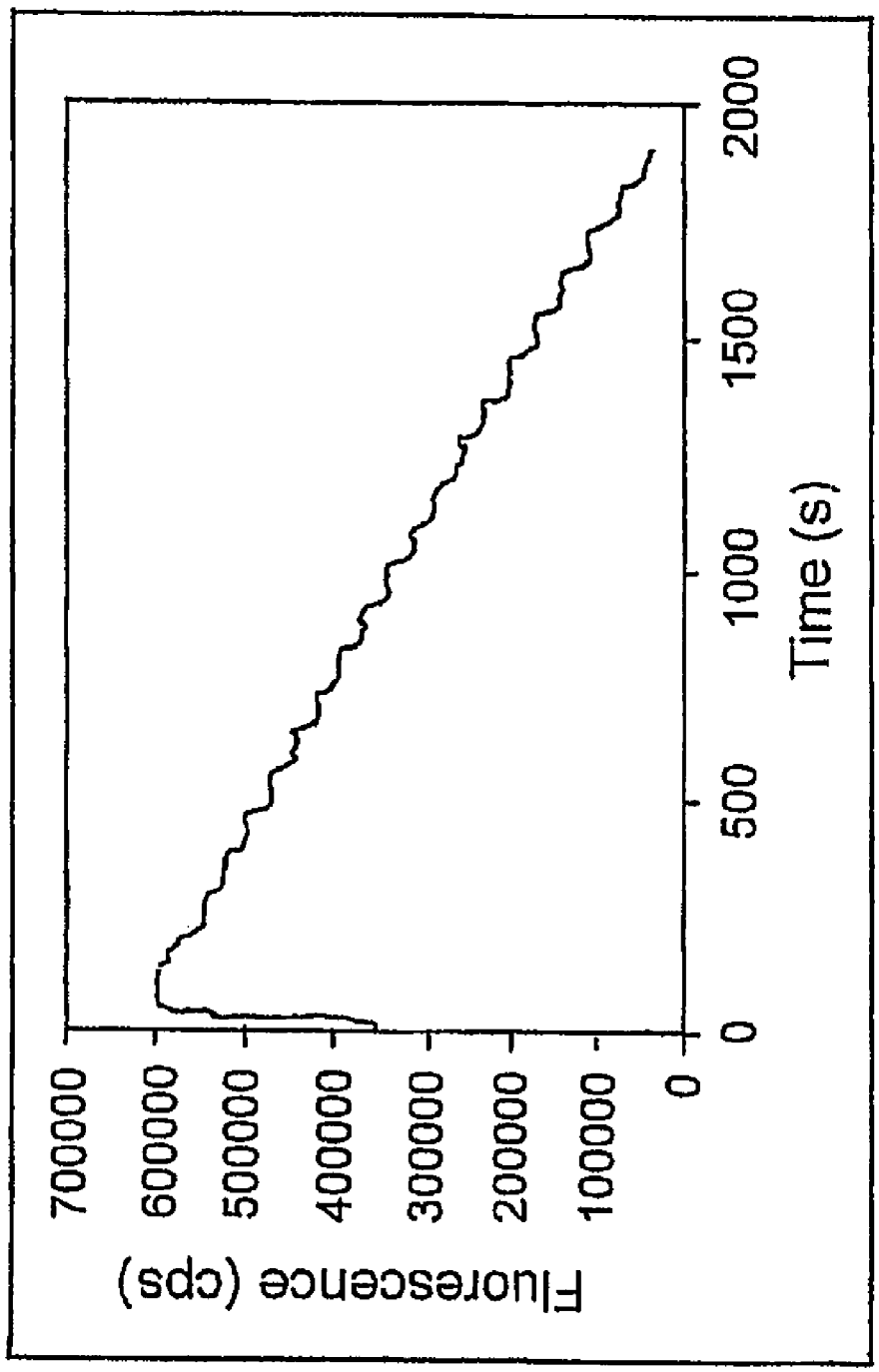
FIG. 28 illustrates a graph of representative data from the system shown in FIG. 27.

Microsyringe pump MP1 can contain an aqueous buffer containing a fluorescent dye (0.5 µM resorufin in 50 mM HEPES with 0.1% CHAPS). Microsyringe pump MP2 can contain an aqueous buffer. Flow of pumps MP1 and MP2 can be controlled with a computer (not shown) such that the combined volumetric flow is a constant 40 nL/min, and a 5% step gradient is generated in which ratio of the pump speeds is 100:0 then 95:5 then 90:10, etc. down to 0:100. Fluid can exit chip MC via an attached capillary CP3. Light from a laser LA (such as the Model CLF-532-50, lasing at 532 nm, available from StockerYale Inc., Salem, N.H.) can be focused with a 10× microscope objective MO (Nikon Instrument Inc., Waltham, N.Y.) into fiber optic FO1 for exciting the fluorescent dye in microcuvette C. Light emitted by the fluorescent dye in microcuvette C can collected by fiber optic FO2. When this light emits from fiber optic FO2, the light can pass through a barrier filter BF (such as the bandpass filter, 605 nm center with 75 nm bandpass, available from Chroma Technology Corp. of Brattleboro, Vt.). The light can then be directed onto the face of a photomultiplier tube PT (such as the Model 814, available from Photon Technologies, Inc. of London, Ontario, Canada). FIG. 28 illustrates a graph of representative data from system 2700 (shown in FIG. 27).

Figure 29:
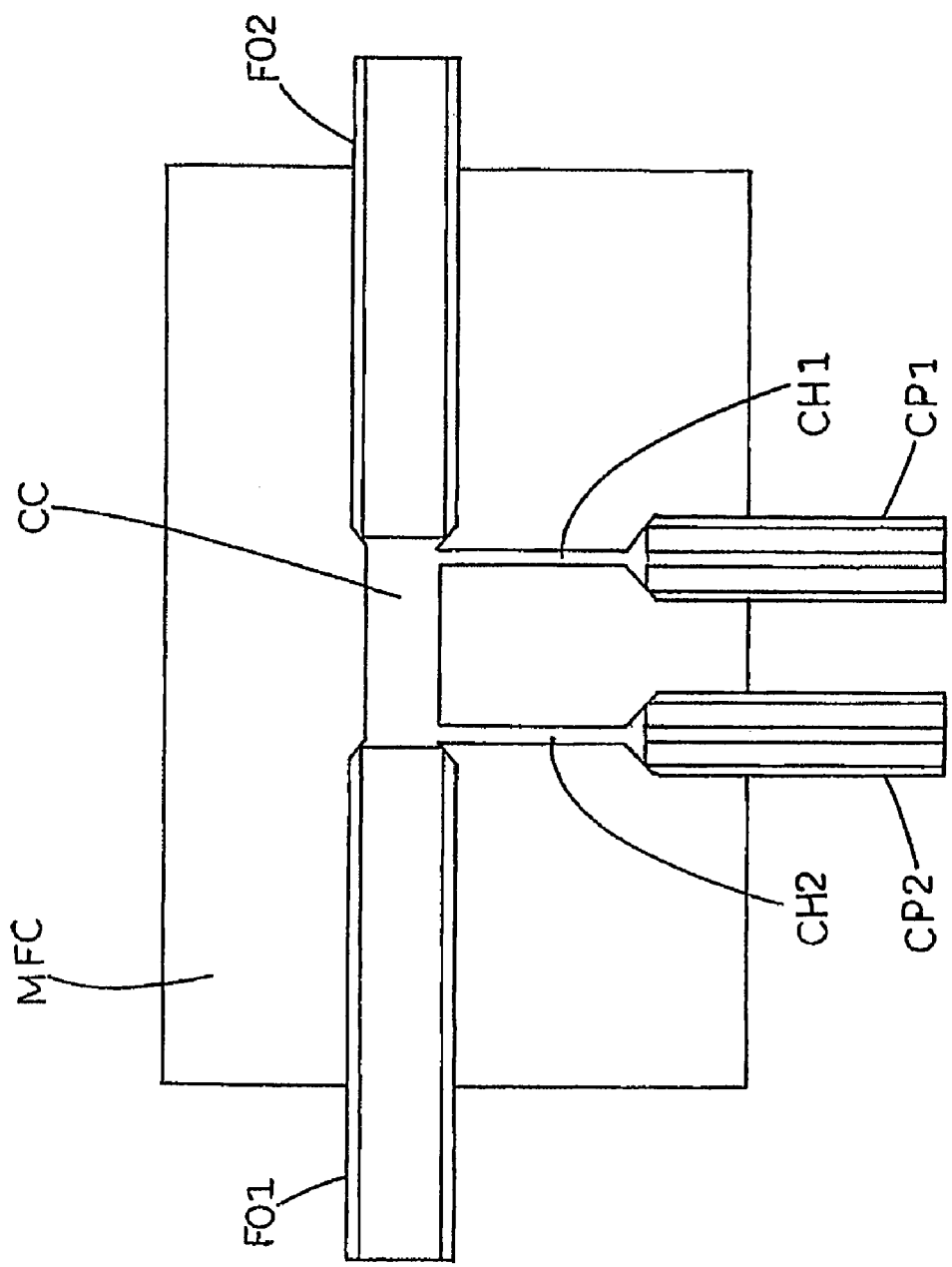
FIG. 29 is a top view of a microfluidic chip for introducing two beams of light into a fluid.

FIG. 29 illustrates a top view of a microfluidic chip MC for introducing two beams of light into a fluid. Alternatively, microfluidic chip MC can introduce one beam of light into a fluid and monitor light absorbed by the fluid. Microfluidic chip MC can include a cuvette chamber CC for receiving fluid from a capillary CP1. Fluid can enter chip MC via capillary CP1, flow through a microchannel CH1, and enter cuvette channel CC. Next, the fluid can exit cuvette channel CC through microchannel CH2 and capillary CP2.

Referring still to FIG. 29, one end of a fiber optic FO1 can connect to cuvette channel CC. An opposing end of fiber optic FO1 can connect to a remote light source (not shown). Another fiber optic FO2 can connect to cuvette channel CC and its opposing end can attach to a photodetector (not shown). Fluid can be pumped through cuvette chamber CC while light is introduced via fiber optic FO1. Light can be absorbed by the fluid and collected by fiber optic FO2 and detected at the off-chip photodetector.

Adsorption of a molecule to the wall of a microfluidic channel can sometimes present a problem in microfluidic and other miniaturized systems in which the ratio of surface area to volume is many orders of magnitude larger than is found in more conventional approaches, such as for example, dispensing and mixing of solutions in microtiter plates. Adsorption of molecules in microfluidic systems and other miniaturized devices can be a major obstacle to miniaturization as the adsorption can affect molecule concentrations within fluids, thereby negatively impacting data collected from the microfluidic systems or other miniaturized devices. Adsorption driven changes in concentration can be especially problematic for microfluidic systems used to generate concentration gradients.

In some embodiments, the presently disclosed subject matter provides apparatuses and methods for using the same that can decrease the interference of adsorption to concentration dependent measurements, such as in biochemistry reactions including $IC_{50}$ determinations, by altering the geometry of a microfluidic channel. Although adsorption may not be eliminated, the change in concentration caused by adsorption can be minimized. In general terms, the effects of adsorption on measurements can be minimized by reducing the ratio of channel surface area to fluid volume within the channel (S/V), which also increases diffusion distances. However, as a high surface area to volume ratio can be an unavoidable consequence of the miniaturization of microfluidics, the geometries provided by some embodiments of the presently disclosed subject matter to minimize adsorption consequences are most unexpected by persons in the field of microfluidics. The presently disclosed subject matter provides for, in some embodiments, using large channel diameters in regions of the microfluidic chip most affected by adsorption of reaction components, that is, in regions where a reaction proceeds and/or where measurements are taken. In some embodiments of the presently disclosed subject matter, and with reference to the microfluidic chip embodiment shown in FIG. 2, large channel diameters at a detection point of microchannel segment MS1 can be provided to reduce adsorption effects (also referred to as aging loop).

Figure 30:
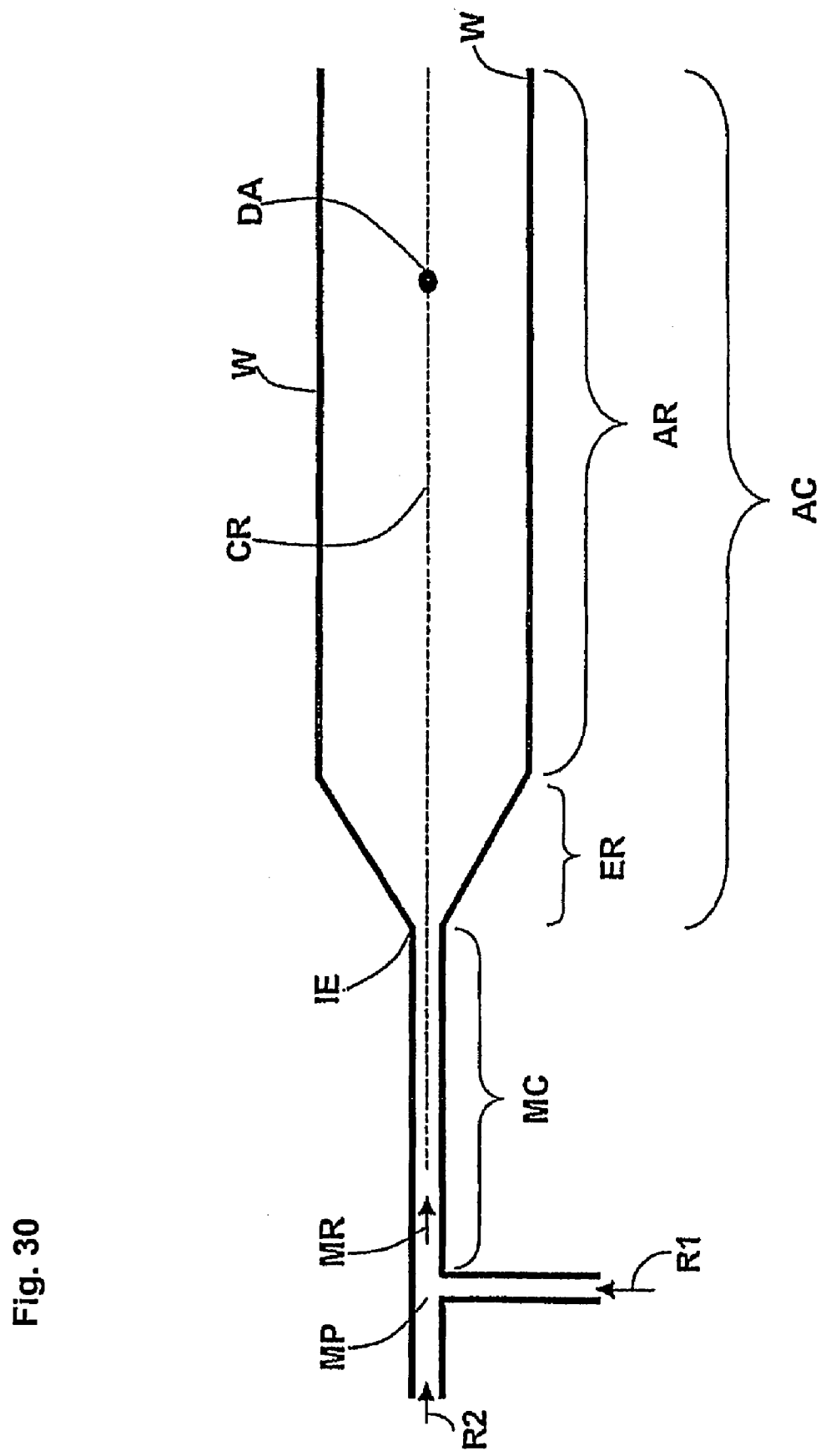
FIG. 30 is a schematic top view of an embodiment of an analysis channel disclosed herein and upstream fluidly communicating microscale channels.

Turning now to FIG. 30, an embodiment of a novel analysis channel of the presently disclosed subject matter is illustrated in a top view. FIG. 30 shows the direction of flow by arrows R1 and R2 of two fluid reagent streams, which can combine at a merge region or mixing point MP. After combining into a merged fluid stream, the reagents within the stream can flow in a direction indicated by arrow MR down a mixing channel MC that can be narrow to permit rapid diffusional mixing of the reagent streams, thereby creating a merged fluid reagent stream. The fluid stream of reagents can then pass into an analysis channel AC, at an inlet or inlet end IE that can have a channel diameter and a cross-sectional area equivalent to that of mixing channel MC. The merged fluid stream can then flow through an expansion region ER that can have a cross-sectional area that can gradually increase and where the surface area to volume ratio can thereby gradually decrease. The merged fluid stream can then continue into an analysis region AR of analysis channel AC with an enlarged cross-sectional area and a reduced surface area to volume ratio. A reaction can be initiated by mixing of the reagent streams at the mixing point MP. However, due to continuity of flow, the flow velocity slows dramatically in analysis region AR of analysis channel AC, and the majority of transit time between mixing point MP and a detection area DA is spent in the larger diameter analysis region AR. Measurements can be made inside this channel, such as with confocal optics, to achieve measurements at detection area DA, which can be located at a center axis CR of analysis region AR of analysis channel AC. Center analysis region CR can be a region equidistant from any channel wall W of analysis channel AC. Thus, the fluid at center analysis region CR of detection area DA can be effectively "insulated" from adsorption at channel walls W. That is, the amount of any reagents removed at channel wall W can be too small, due to the greatly decreased surface area, and the diffusion distance to channel wall W can be too long, due to the greatly increased diffusion distance from center analysis region CR to channel wall W, to greatly affect the concentration at centerline CL. The confocal optics, for example, can reject signal from nearer channel wall W of analysis region AR, permitting measurements to be made at center analysis region CR where the concentration is least affected by adsorption at channel wall W.

A consequence of increasing analysis channel AC cross-section by increasing channel diameter is that the ratio of channel surface area to fluid volume (S/V) within the channel is decreased, relative to a narrower channel. For example, to measure a reaction 3 minutes after mixing, with a volumetric flow rate of 30 nL/min, the reaction should be measured at a point in the channel such that a microfluidic channel section spanning from mixing point MP to detection area DA encloses 90 nL. For an analysis channel with a square cross-section and a diameter of 25 µm, this point is about 144 mm downstream from mix point MP. This channel has a surface area of $1.44 \times 10^{-5}$ square meters, yielding a surface to volume ratio S/V equal to $1.6 \times 10^5$ $m^{-1}$. For a channel with a diameter of 250 µm, the measurement is made 1.44 mm downstream from mix point MP. This wider channel has a surface area of $1.44 \times 10^{-6}$ square meters, yielding a S/V equal to $1.6 \times 10^4$ $m^{-1}$, which is $1/10^{th}$ the S/V of the narrower channel. This alone can decrease ten-fold the removal of compound per unit volume by adsorption.

This geometry change can also decrease the radial diffusive flux of compound. Flow in these small channels is at low Reynolds number, so diffusion from a point in the fluid is the only mechanism by which compound concentration changes radially in a microfluidic channel. Increasing the radius of the channel, thereby decreasing the radial diffusive flux, therefore, means that the concentration of compound at center analysis region CR of analysis region AR can be less affected by adsorption than in the smaller upstream channels.

Thus, increasing the cross-sectional area of analysis region AR of analysis channel AC can both decrease the amount of adsorption at the wall per unit volume and decrease the rate of flux of compound from center analysis region CR to any of channel walls W. Both together mean that the concentration at center analysis region CR can decrease more slowly due to adsorption of compound.

Further, in all embodiments, the surface area of all channels exposed to compounds, not just analysis channel AC, can preferably be kept minimal, especially those channels through which concentration gradients flow. This can be accomplished by making channels as short as practicable. Additionally, when the volume contained by a channel must be defined (e.g. where the channel must contain a volume of 50 nL), it is best to use larger diameters/shorter lengths wherever possible to reduce S/V.

Another benefit of increasing analysis channel AC cross-section by increasing channel diameter is that the length of the channel down which the fluid flows can be reduced. In the example given earlier, a channel with 25 µm diameter needed to be 144 mm long to enclose 90 nl whereas the channel with 250 µm diameter needed to be only 1.44 mm long. This shorter channel can be much easier to fabricate and has a much smaller footprint on a microfluidic chip.

Still another benefit of increasing analysis channel AC cross-section is that it will behave like an expansion channel, which filters noise out of chemical concentration gradients, as disclosed in co-pending, commonly assigned U.S. Provisional Application entitled MICROFLUIDIC SYSTEMS, DEVICES AND METHODS FOR REDUCING NOISE GENERATED BY MECHANICAL INSTABILITIES, U.S. Provisional Application No. 60/707,245, herein incorporated by reference in its entirety. The result is that signal to noise is larger in an analysis channel AC with larger cross-section.

Figure 31:
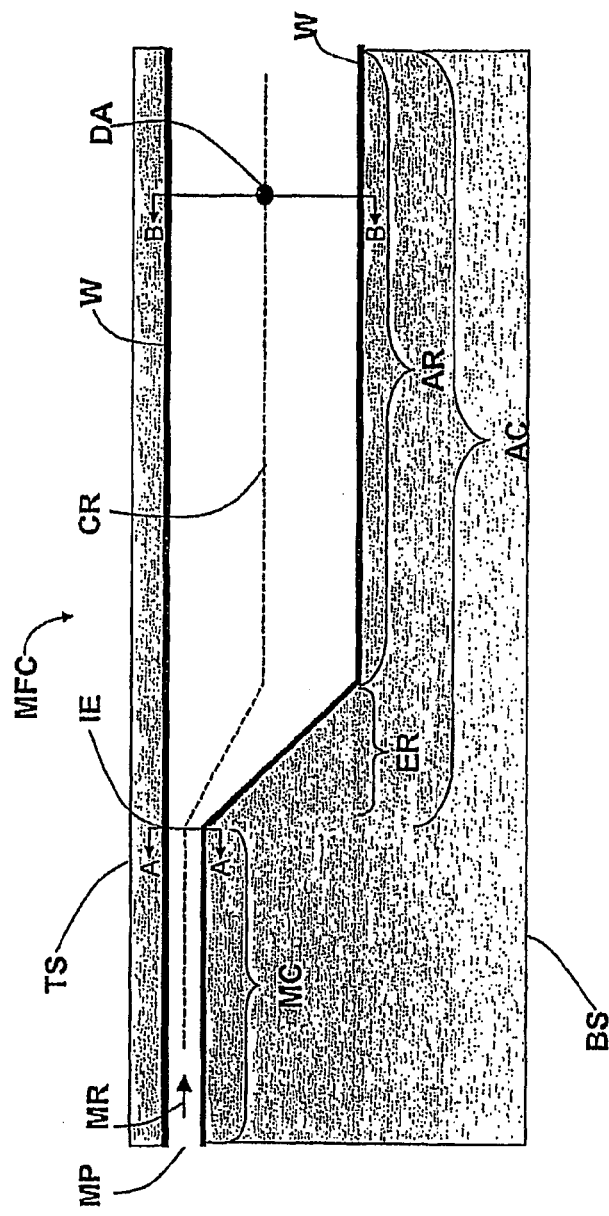
FIG. 31A is a schematic cross-sectional side view of an embodiment of analysis channel disclosed herein and upstream fluidly communicating microscale channel.
FIG. 31B shows schematic cross-sectional cuts at A-A and B-B of the analysis channel of FIG. 31A.
Figure 31:
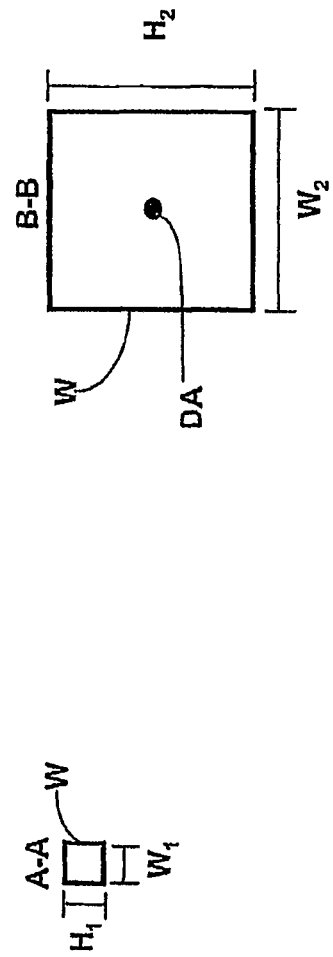

FIG. 31A presents a cross-sectional side view of a portion of a microfluidic chip MFC comprising mixing channel MC and analysis channel AC depicted in FIG. 30. Microfluidic chip MFC shown in FIG. 31A can be constructed by machining channels into a bottom substrate BS and enclosing channels by bonding a top substrate TS to bottom substrate BS or otherwise forming channels within microfluidic chip MC with bottom substrate BS and top substrate TS being integral. In FIG. 31A, only the flow of merged reagent fluid stream having a flow direction indicated by arrow MR after mixing point MP is shown. Flow in a microfluidic channel can be at low Reynolds number, so the streamline of fluid that flows along center analysis region CR of the narrower mixing channel MC can travel at the mid-depth along entire mixing channel MC, becoming center analysis region CR of analysis region AR of analysis channel AC. Detection area DA can reside along center analysis region CR at a point sufficiently far downstream of mixing channel MC to permit the reaction to proceed to a desired degree.

Analysis channel AC can approximate a circular cross-section as closely as possible to produce the smallest ratio of surface area to volume, and also to produce the largest diffusion distance from centerline center analysis region CR to a channel wall W. However, microfluidic channels may not be circular in cross-section due to preferred manufacturing techniques. Rather, they can be more likely square in cross-section, with the exact shape depending on the technique used to form the channels. For such channels, a cross-section of analysis channel AC, particularly within analysis region AR, can have an aspect ratio as close to one as possible or, more precisely stated, the distance from center analysis region CR to channel wall W can be as nearly constant in all radial directions as possible.

FIG. 31B shows two different cross-sectional views along analysis channel AC as viewed along cutlines A-A and B-B. Both cross-sectional views illustrate an aspect ratio approximating one. That is, for cross-section A-A, height $H_1$ of mixing channel MC is approximately equal to width $W_1$ of mixing channel MC, such that $H_1/W_1$ approximately equals one. Comparably, for cross-section B-B, height $H_2$ of mixing channel MC is approximately equal to width $W_2$ of mixing channel MC, such that $H_2/W_2$ approximately equals one.

FIG. 31B further shows that the cross-sectional area ($H_2 \times W_2$) of analysis region AR at cutline B-B, which is located at detection area DA of analysis region AR, is significantly larger than the cross-sectional area ($H_1 \times W_1$) of input end IE at cutline A-A. In some embodiments of the presently disclosed subject matter, the cross-sectional area at detection area DA can be at least twice the value of the cross-sectional area value at input end IE and further upstream, such as in mixing channel MC. Further, in some embodiments, the cross-sectional area at detection area DA can be between about two times and about ten times the value of the cross-sectional area value at input end IE. As shown in cutline B-B of FIG. 31B, detection area DA can be positioned along center analysis region CR approximately equidistant from each of walls W to provide maximal distance from walls W, and thereby minimize effects of molecule adsorption to walls W. It is clear from FIG. 31B that the larger cross-sectional area at cutline B-B can provide both greater distance from walls W and smaller S/V than the smaller cross-sectional area at cutline A-A, both of which can reduce adsorption effects on data analysis, as discussed herein. Although detection area DA is shown in the figures as a circle having a distinct diameter, the depiction in the drawings is not intended as a limitation to the size, shape, and/or location of detection area DA within the enlarged cross-sectional area of analysis region AR. Rather, detection area DA can be as large as necessary and shaped as necessary (e.g. circular, elongated oval or rectangle, etc.) to acquire the desired data, while minimizing size as much as possible to avoid deleterious adsorption effects on the data. Determination of the optimal balance of size, shape and location while minimizing adsorption effects is within the capabilities of one of ordinary skill in the art without requiring undue experimentation.

Additional details and features of analysis channel AC are disclosed in co-pending, commonly assigned U.S. Provisional Application entitled METHODS AND APPARATUSES FOR REDUCING EFFECTS OF MOLECULE ADSORPTION WITHIN MICROFLUIDIC CHANNELS, U.S. Provisional Application No. 60/707,366, herein incorporated by reference in its entirety.

In some embodiments, the presently disclosed subject matter provides apparatuses and methods for making and using the same that can decrease the interference of adsorption to concentration dependent measurements, such as in biochemistry reactions (including $IC_{50}$ determinations), by reducing adsorption of molecules to microfluidic channel walls. In some embodiments, the presently disclosed subject matter provides microfluidic chips comprising channels and chambers with treated surfaces exhibiting reduced adsorption of molecules to channel walls, such as for example hydrophilic surfaces, and methods of preparing and using the same. In some embodiments, methods of preparing hydrophilic surfaces by treating hydrocarbon-based plastics, such as for example polycarbonate, with fluorine gas mixtures are provided. In some exemplary embodiments, the methods comprise contacting a mixture of fluorine gas and an inert gas with the surface to be treated, then flushing the surface with air. This treatment results in plastic surfaces of increased hydrophilicity (increased surface energy). Hydrophobic solutes, in particular known and potential drug compounds, in solutions in contact with these treated hydrophilic plastic surfaces are less likely to be adsorbed onto the more hydrophilic surfaces. Plastics comprising the treated surfaces are useful in providing many improved drug discovery and biochemical research devices for handling, storing, and testing solutions containing low concentrations of hydrophobic solutes.

Additional details and features of hydrophilic surfaces in microfluidic systems and methods of making and using the same are disclosed in co-pending, commonly owned U.S. Provisional Application entitled PLASTIC SURFACES AND APPARATUSES FOR REDUCED ADSORPTION OF SOLUTES AND METHODS OF PREPARING THE SAME, U.S. Provisional Application No. 60/707,288.

Further, in some embodiments of the presently disclosed subject matter, microfluidic systems are provided comprising an analysis channel with an enlarged cross-sectional area and a reduced surface area to volume ratio and further comprising channels and chambers with hydrophilic surfaces.

It will be understood that various details of the subject matter disclosed herein can be changed without departing from the scope of the subject matter. Furthermore, the foregoing description is for the purpose of illustration only, and not for the purpose of limitation.

What is claimed is:

1. A method for connecting a light-guiding conduit to a microfluidic channel, the method comprising:
   (a) providing a first and second substrate comprising first surfaces, wherein the first surfaces of the first and second substrates form a microfluidic channel and a connection channel when the first surfaces are positioned together, and wherein the connection channel extends from an edge of the first surface of the first or second substrate to the microfluidic channel;
   (b) inserting a light-guiding conduit having an end into the connection channel such that the light-guiding conduit stops at a point where the end of the light-guiding conduit meets an edge of the connection channel;
   (c) inserting a light-curable adhesive into an area between the light-guiding conduit and the connection channel, wherein the light-curable adhesive flows toward the end of the connection channel with a leading edge;
   (d) delivering a light beam to light-curable adhesive through the end of the light-guiding conduit; and
   (e) curing the leading edge of the light-curable adhesive.

2. The method of claim 1, wherein the first substrate comprises a material selected from the group consisting of polymer, metal, silicon, silica, glass, quartz, sapphire, zinc oxide, alumina, Group III-V compounds, and combinations thereof.

3. The method of claim 1, wherein the first surface of the first substrate is at least substantially planar.

4. The method of claim 1, wherein the second substrate comprises a material selected from the group consisting of polymer, metal, silicon, silica, glass, quartz, sapphire, zinc oxide, alumina, Group III-V compounds, and combinations thereof.

5. The method of claim 1, wherein the first surface of the second substrate is at least substantially planar, and the first surface of the first substrate comprises the microfluidic channel and connection channel formed therein.

6. The method of claim 1, wherein the microfluidic channel and the connection channel are in fluid communication.

7. The method of claim 1, wherein the step of providing a first and second substrate comprises forming the connection channel in the first surface of one of the first and second substrates.

8. The method of claim 7, further comprising forming the microfluidic channel in the first surface of one of the first and second substrates.

9. The method of claim 1, wherein the length of the connection channel is approximately 3 to 10 millimeters.

10. The method of claim 1, wherein the connection channel is at least substantially cylindrical in shape.

11. The method of claim 1, wherein the connection channel is at least substantially semi-cylindrical in shape.

12. The method of claim 1, wherein the step of bonding comprises thermal bonding.

13. The method of claim 1, wherein the step of inserting the light-guiding conduit into the connection channel occurs prior to the step of bonding the first surfaces of the first and second substrates.

14. The method of claim 1, wherein insertion of the light-guiding conduit is limited by a decreased diameter of the connection channel.

15. The method of claim 14, wherein the decreased diameter of the light-guiding conduit is a taper that transitions to the microfluidic channel.

16. The method of claim 1, wherein insertion of the light-guiding conduit is facilitated by an opening of the connection channel that is greater than the diameter of the connection channel.

17. The method of claim 16, wherein the larger diameter opening is a taper that transitions to the microfluidic channel.

18. The method of claim 1, wherein the step of inserting the light-guiding conduit comprises positioning an end of the light-guiding conduit in the connection channel, wherein the end of the connection channel is approximately 0 to 200 micrometers from the microfluidic channel.

19. The method of claim 1, wherein the maximum diameter of the light-guiding conduit is smaller than the minimum diameter of the connection channel.

20. The method of claim 1, wherein the maximum diameter of the light-guiding conduit is approximately the same as the minimum diameter of the connection channel.

21. The method of claim 1, wherein the light-guiding conduit is a capillary tube.

22. The method of claim 1, wherein the light-guiding conduit is a light-guiding capillary tube.

23. The method of claim 1, wherein the light-guiding conduit is a fiber optic.

24. The method of claim 1, wherein the method further comprises applying a second light beam to cure adhesive not cured by the first light beam.

25. The method of claim 24, wherein the light-guiding conduit is a light-guiding capillary, and the cured adhesive completes a fluid path from a lumen of the light-guiding capillary to the microfluidic channel.

26. The method of claim 1, wherein the step of delivering comprises positioning the area between the light-guiding conduit and the connection channel at an adhesive dispenser for receiving the adhesive substance.

27. The method of claim 1, further comprising providing a computer for controlling the positioning of the area between the light-guiding conduit and the connection channel at an adhesive dispenser.

* * * * *